US011124818B2

(12) United States Patent
Enke et al.

(10) Patent No.: US 11,124,818 B2
(45) Date of Patent: Sep. 21, 2021

(54) METHOD FOR MODIFYING MICROCYSTINS AND NODULARINS

(71) Applicant: Cyano Biotech GmbH, Berlin (DE)

(72) Inventors: Heike Enke, Berlin (DE); Wolfram Lorenzen, Berlin (DE); Stefan Jahns, Berlin (DE); Dan Enke, Berlin (DE); Timo Niedermeyer, Halle Saale (DE); Julia Moschny, Sulzbach-Rosenberg (DE)

(73) Assignee: Cyano Biotech GmbH, Berlin (DE)

( * ) Notice: Subject to any disclaimer, the term of this patent is extended or adjusted under 35 U.S.C. 154(b) by 0 days.

(21) Appl. No.: 16/605,248

(22) PCT Filed: May 9, 2018

(86) PCT No.: PCT/EP2018/062156

§ 371 (c)(1),
(2) Date: Oct. 15, 2019

(87) PCT Pub. No.: WO2018/219619

PCT Pub. Date: Dec. 6, 2018

(65) Prior Publication Data

US 2020/0377922 A1 Dec. 3, 2020

(30) Foreign Application Priority Data

May 9, 2017 (EP) .................................... 17170284

(51) Int. Cl.

| | |
|---|---|
| ***A61K 47/64*** | (2017.01) |
| ***C07K 7/56*** | (2006.01) |
| ***C12N 1/20*** | (2006.01) |
| ***C12P 21/04*** | (2006.01) |
| ***C12P 21/02*** | (2006.01) |
| ***A61K 47/68*** | (2017.01) |
| ***C07K 7/58*** | (2006.01) |

(52) U.S. Cl.

CPC .............. *C12P 21/02* (2013.01); *A61K 47/64* (2017.08); *A61K 47/6829* (2017.08); *C07K 7/56* (2013.01); *C07K 7/58* (2013.01); *C12N 1/20* (2013.01); *C12N 2500/32* (2013.01); *C12N 2500/33* (2013.01)

(58) Field of Classification Search

CPC . A61K 47/64; C07K 2/00; C07K 7/56; C12N 1/20; C12N 2500/32; C12N 2500/33; C12P 21/00; C12P 21/005; C12P 21/02
See application file for complete search history.

(56) References Cited

U.S. PATENT DOCUMENTS

| | | | |
|---|---|---|---|
| 2004/0101899 A1 | 5/2004 | Dillon et al. | |
| 2007/0092940 A1 | 4/2007 | Eigenbrot et al. | |
| 2019/0263868 A1* | 8/2019 | Neilan | C07K 14/405 |

FOREIGN PATENT DOCUMENTS

| | | | |
|---|---|---|---|
| CN | 101125889 | 2/2008 | |
| EP | 1698638 A1 * | 9/2006 | A61P 31/00 |
| WO | 2002/24909 | 3/2002 | |
| WO | 2002/38766 | 5/2002 | |
| WO | 2002/094852 | 11/2002 | |
| WO | 2003/014294 | 2/2003 | |
| WO | 2003/035846 | 5/2003 | |
| WO | 2003/045422 | 6/2003 | |
| WO | 2004/011611 | 2/2004 | |
| WO | 2004/058309 | 7/2004 | |

OTHER PUBLICATIONS

H. Chen. Environmental Factors Regulating Cyanobacterial Dynamics and the Occurrence of Microcystin, with an Emphasis on Nitrogen. PhD Dissertation, University of Alberta, Spring 2009. (Year: 2000).*
Tonk et al. Amino acid availability determines the ratio of microcystin variants in the cyanobacterium Planktothris agardhii. FEMS Microbiology Ecology. 2008, vol. 65, pp. 383-390. (Year: 2008).*
Welker et al. Diversity of coexisting Planktothrix (Cyanobacteria) chemotypes deduced by mass spectral analysis of microcystins and other oligopeptides. Archives of Microbiology. 2004, vol. 182, pp. 288-298. (Year: 2004).*
Yan et al. Comparative effects of inorganic and organic nitrogen on the growth and microcystin production of Microcystis aeruginosa. World Journal of Microbiology and Biotechnology. 2015, vol. 31, pp. 763-772. (Year: 2015).*
International Search Report dated Oct. 24, 2018 in PCT/EP2018/062156.
Written Opinion dated Oct. 24, 2018 in PCT/EP2018/062156.
International Preliminary Report on Patentability dated Apr. 23, 2019 in PCT/EP2018/062156.
Barnett et al., Genomics 3, 59-66 (1988).
Coussens et al., Science 230, 1132-1139 (1985).
Kries et al., Angew. Chem. Int. Ed. 2014, 53, 10105-10108.
Moschny et al., GA 2017, 65th International Congress and Annual Meeting of the Society for Medicinal Plant and Natural Product Research, Sep. 3-9, 2017, Basel, Switzerland, Poster.
Niedermeyer et al., Nat. Prod. Bioprospect. (2014) 4:37-45.
Niedermeyer et al., PLoS One 9(3): e91476 (2014) (7 pages).
Spicer et al., Nat. Commun. 5:4740 (2014) (14 pages).
Thompson et al., Science 293 (5537), 2108-2111 (2001).
Tillich et al., BMC Microbiology 2014, 14:239 (13 pages).
Zemskov et al., J. Org. Chem. 2017, 82, 3680-3691.

(Continued)

*Primary Examiner* — Jeffrey E. Russel
(74) *Attorney, Agent, or Firm* — Grüneberg and Myers PLLC

(57) ABSTRACT

A method is used for producing a modified non-ribosomal peptide, e.g. a modified microcystin and/or modified nodularin (together CA), including the steps of: a) growing a modified non-ribosomal peptide producing cyanobacteria strain in a culture media, h) adding one or more modified substrates, preferably modified amino acids to said culture, and c) inoculating the non-ribosomal peptide, producing strain the presence of said modified substrates. The thus modified non-ribosomal peptide may be used for the therapy of various diseases.

22 Claims, 60 Drawing Sheets

Specification includes a Sequence Listing.

(56) References Cited

OTHER PUBLICATIONS

International Search Report dated Jan. 3, 2019 in PCT/EP2018/062129.
Written Opinion dated Jan. 3, 2019 in PCT/EP2018/062129.
International Preliminary Report on Patentability dated Jul. 1, 2019 in PCT/EP2018/062129.
Bouaïcha, et al., "*Structural Diversity, Characterization and Toxicology of Microcystins*," Toxins, 2019, 11, 714, 40 pages.
Bowie, et al., "*Deciphering the Message in Protein Sequences: Tolerance to Amino Acid Substitutions*," Science 247 (4948), 1306-1310, (Year: 1990).
Burgess, et al., "*Possible Dissociation of the Heparin-binding and Mitogenic Activities of Heparin-binding* (*Acidic Fibroblast*) *Growth Factor-1 from Its Receptor-binding Activities by Site-directed Mutagenesis of a Single Lysine Residue*," The Journal of Cell Biology, vol. 111, Nov. 1990, 2129-2138.
Lazar, et al., "*Transforming Growth Factor α: Mutation of Aspartic Acid 47 and Leucine 48 Results in Different Biological Activities*," Molecular and Cellular Biology, vol. 8, No. 3, Mar. 1988, pp. 1247-1252.
Mikhailov, et al., "*Production and specificity of mono and polyclonal antibodies against microcystins conjugated through N-methyldehydroalanine*," Toxicon 39 (2001) 477-483.
Namikoshi, et al., "*Identification of 12 Hepatotoxins from a Homer Lake Bloom of the Cyanobacteria Microcystis aeruginosa, Microcystis viridis, and Microcystis wesenbergii: Nine New Microsystins*," J. Org. Chem. 1992, 57, 866-872.
B. Nolting, "*Linker Technologies for Antibody-Drug Conjugates*," Antibody-Drug Conjugates, Methods in Molecular Biology, vol. 1045, Chapter 5, pp. 71-100 (Year: 2013).
Sadik, et al., "*Novel fluorescent biosensor for pathogenic toxins using cyclic polypeptide conjugates*," Chem. Commun., 2004, 1136-1137.
U.S. Appl. No. 16/605,264, filed Oct. 15, 2019, Enke et al.

* cited by examiner

NODULARINS

ANABAENOPEPTINS/ OSCILLAMIDES

Exemplary embodiment No. 2:

Growth curve of CBT 480 cultures with and without Prg-Tyr (Tyr=Tyrosine) added.

Exemplary embodiment No. 3:

Growth curve of CBT 275 cultures with and without Azido-Lys (Lys=Lysine) added.

Exemplary embodiment No. 4:

Growth curve of CBT 275 cultures with and without Prg-Tyr (Tyr=Tyrosine) added.

Exemplary embodiment No. 5:

Growth curve of CBT 1 cultures with and without Nitro-Arg (Arg=Arginine) added.

Exemplary embodiment No. 6:

Growth curve of CBT 275 cultures with and without Furyl-Ala (Ala = Alanine) added.

Exemplary embodiment No. 7:

Growth curve of CBT 480 cultures with and without Nitro-Arg (Arg=Arginine) and Prg-Tyr (Tyr=Tyrosine) added.

Exemplary embodiment No. 8:

Growth curve of CBT 329 cultures with and without Nitro-Arg (Arg=Arginine) added.

Exemplary embodiment No. 9:

Growth curve of CBT 1 cultures with and without Azido-Lys (Lys=Lysine) added.

Exemplary embodiment No. 10:

Growth curve of CBT 633 cultures with and without Azido-Norval (Norval=Norvaline) added.

Fig. 31

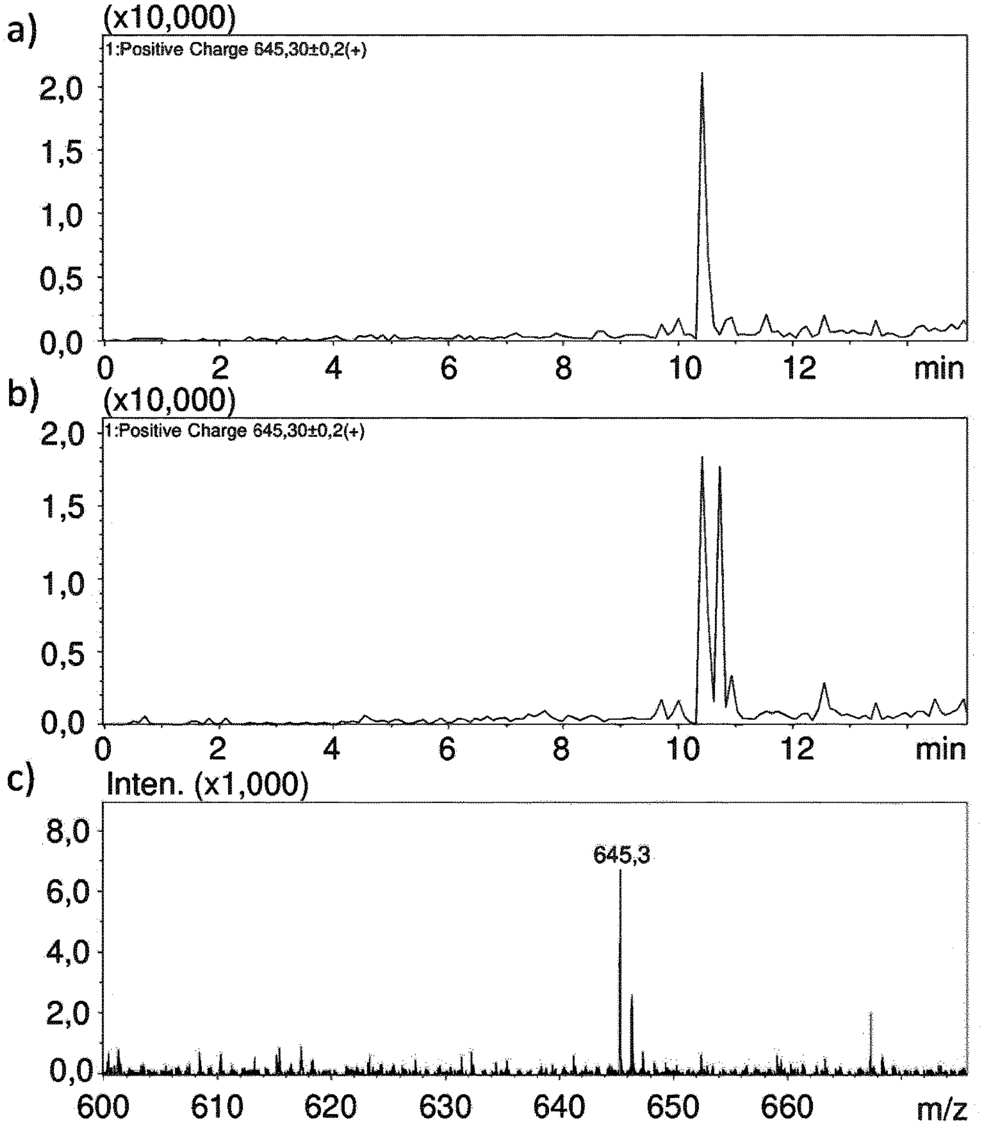

Exemplary embodiment No. 19 : Incorporation of the modified substrate Prg-Tyr (Tyr=Tyrosine) into Cryptophycin 1 produced by strain CBT 567.

Extracted ion chromatogram from HPLC-MS data of mass value of protonated molecular ion of novel Cryptophycin variant for sample of control cultivation (a) and sample of cultivation with added modified substrate (b) in the positive ionization mode. Finally, c) shows the averaged mass spectrum of the additional peak in chromatogram b). Detector signal intensities (y-Axis) are measured in counts (dimensionless quantity).

| Sample | Yield (%) | Monomers (%) | Aggregates (%) | Small Fragments (%) |
|---|---|---|---|---|
| Microcystin-ADC-1 | 70 | 98.9 | 0.8 | 0.2 |
| Microcystin-ADC-2 | 80 | 99.0 | 0.8 | 0.2 |

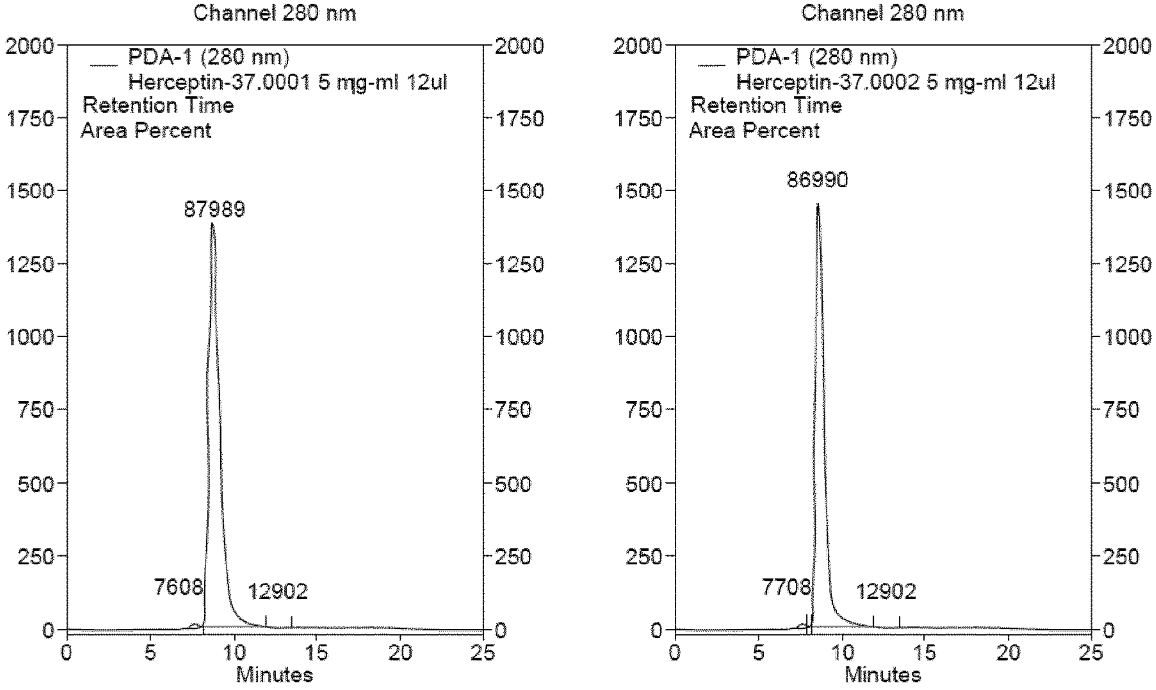

FIG. 32

Exemplary embodiment No. 20: Produced ADCs and results of analytical SEC-HPLC. In analytical SEC-HPLC the conjugates Microcystin-ADC1 and Microcystin-ADC2 showed a high level of purity with 98.9% and 99.0% monomers. In both cases, aggregates and small fragments were detected with rates of 0.8% and 0.2%.

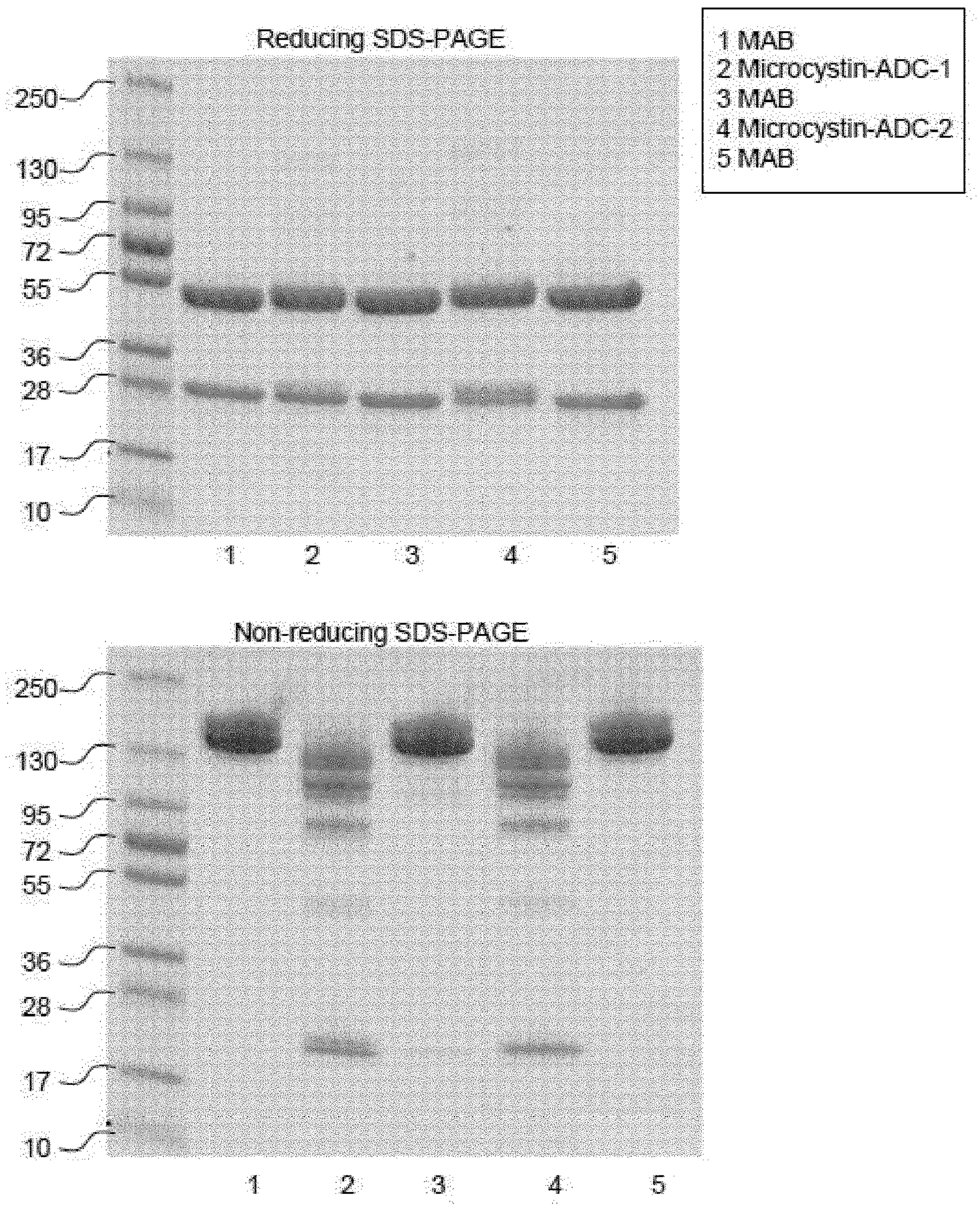

FIG. 33

Exemplary embodiment No. 21: Coomassie stained Gelelectrophoresis gels demonstrating the binding of Microcystin variants 1 and 2 as payloads on monoclonal antibodies. In Coomassie staining under reducing conditions all samples showed a signal for the heavy chain at app. 50 kDa and the light chain at app. 25 kDa. All conjugates showed an up-shift of the protein signal of the heavy and the light chain compared to the naked MAB indicating toxin conjugation to both antibody chains. For all ADCs a double-signal was detected for the light chain indicating both, conjugated and unconjugated species. In Coomassie staining under non-reducing conditions the naked antibody showed a double signal at app. 150 kDa for the intact antibody. The ADCs showed a variety of signals between 25 kDa and 150 kDa, since in both cases the toxin was conjugated to reduced interchain disulfides leading to instability of the antibody during incubation at 37°C.

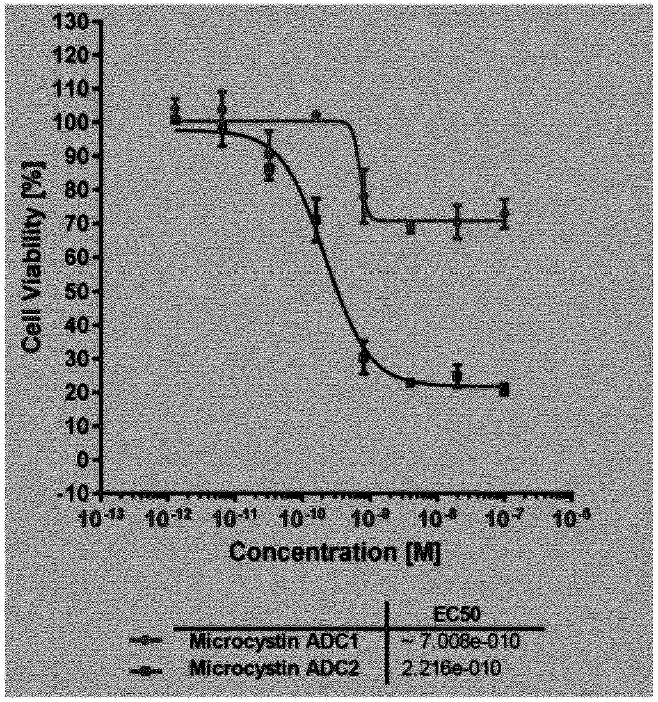

| Sample | $EC_{50}$ [M] |
|---|---|
| Microcystin-ADC-1 | nfb |
| Microcystin-ADC-2 | $2.2 \times 10^{-10}$ (20 %) |

Fig. 34

Exemplary embodiment No. 22: Successful in vitro proof of concept of Microcystin-based ADCs. The cell viability is monitored in an in-vitro-assay with a cancer cell line for the different concentrations of the Microcystin ADC for two Microcystin variants as payloads. The ADC carries a non-cleavable linker. For Microcystir ADC-2 an $EC_{50}$ values of 220 pM was determined. Differences between structural payload variants underline huge potential of further structural optimization:

METHOD FOR MODIFYING MICROCYSTINS AND NODULARINS

CROSS-REFERENCE TO RELATED APPLICATIONS

This application is a National Stage entry under § 371 of International Application No. PCT/EP2018/062156, filed on May 9, 2018, and which claims the benefit of European Application No. 17170284.8, filed on May 9, 2017.

REFERENCE TO A SEQUENCE LISTING

The present application is accompanied by an ASCII text file as a computer readable form containing the sequence listing, titled "000869US_SL.txt", created on Jun. 10, 2021, with the file size of 17,703 bytes, which is incorporated by reference in its entirety. Applicants hereby state that the information recorded in computer readable form is identical to the written (on paper or compact disc) sequence listing.

FIELD OF INVENTION

This invention is in the field of cancer treatment. It is in the field of toxins for use in cancer treatment. It is in the field of non-ribosomal peptides from cyanobacteria (with microcystins, nodularins but also anabaenopeptins, oscillamides as examples) and their use in the treatment of diseases such as cancer, thrombosis, metabolic diseases but also for other applications. The invention relates to the field of microbiology, molecular biology, pharmacy and biotechnology in general and more specifically to the synthesis of modified non-ribosomal peptides including microcystins and nodularins. This invention is also in the field of enzyme inhibiting tools including phosphatase, proteinase and peptidase inhibiting biochemical tools.

BACKGROUND

Microcystins are toxins produced naturally by cyanobacteria, also known as blue-green algae. When excess cyanobacteria grow in a lake or pond, they form an algal bloom, which often appears as a layer of green scum. However, not all green scum on a lake is an algal bloom, and not all algal blooms contain the kinds of cyanobacteria that produce microcystins. There are many microcystin congeners; microcystin-LR is one of the more toxic and well-studied congener. Microcystins are a group of cyclic heptapeptide hepatotoxins produced by a number of cyanobacterial genera. The most notable of which, and namesake, is the widespread genus *Microcystis*. Structurally, most microcystins consist of the generalized structure cyclo(-D-Ala1-X2-D-MeAsp3-Y4-Adda5-D-Glu6-Mdha7-). X and Y are variable L-amino acids, D-MeAsp is D-erythro-β-methylaspartic acid and Mdha is N-methyldehydroalanine. However, while X and Y are the most variable amino acids, variations can be found at all positions of the microcystin core structure (see FIG. 1). Adda is the cyanobacteria unique C20-β-amino acid 3-amino-9-methoxy-2,6,8-trimethyl-10-phenyl-deca-4,6-dienoic acid. Substitutions of the variable L-amino acids at positions 2 and 4 and less frequently found alterations in the other constituent amino acids result in more than 100 reported natural microcystins to date.

Microcystins are potent inhibitors of type 1 and type 2A protein phosphatases. The $IC_{50}$ of microcystin-LR for example are 0.03 nM and 0.0 nM for type 1 and type 2A protein phosphatases, respectively.

Protein phosphatases 1 and 2A are two of the major phosphatases in eukaryotic cells that dephosphorylate serine and threonine residues.

Protein phosphatase 2B is inhibited 1000-fold less potently, while six other tested phosphatases and eight tested protein kinases are unaffected.

Nodularins are compounds structurally related to the microcystins, as they are evolutionary derived from microcystin and also contain the amino acid Adda found in the microcystins. They are produced especially by Nodularia species, and in contrast to microcystins they are cyclic pentapeptides with the most commonly found congener cyclo[-D-erythro-methylAsp-L-Arg-Adda-D-Glu-Mdhb], where Mdhb is N-methyldehydrobutyrate (see FIG. 1).

Microcystins and nodularins could serve as cancer drugs. It was hypothesized that natural microcystin variants could be isolated that are transported preferentially by the active transporter type OATP1B3 relative to OATP1B1 to advance as anticancer agents with clinically tolerable hepatic toxicity (OATP1B3 transporters are primarily found in cancer tissues, e.g. in liver cancers). Microcystin variants have been isolated and tested for cytotoxicity in cancer cells stably transfected with OATP1B1 and OATP1B3 transporters. Microcystin variants with cytotoxic OATP1B1/OATP1B3 $IC_{50}$ ratios that ranged between 0.2 and 32 were found, representing a 150-fold range in transporter selectivity. As the microcystin structure has a significant impact on transporter selectivity, it is potentially possible to develop analogs with even more pronounced OATP1B3 selectivity and thus enable their development as anticancer drugs. However, a more specific method of delivery would be preferred. One such method involves the novel concept disclosed herein, of adding a targeting moiety. Ideally for a targeted and highly specific cancer therapy that avoids off-target toxicities, the structural variant of a microcystin and nodularin would carry a targeting moiety (e.g. a cancer-specific monoclonal antibody) and is either not or badly transported by all OATP transporter subtypes or it is exclusively or primarily transported by the cancer-specific OATP subtype 1B3. As an example for differences in transport efficiencies among different structural variants of microcystins we refer to the following table.

TABLE

Potency and selectivity of selected Microcystins in models of OATP-expressing HeLa and RKO cells MC toxicity depends on the activity against PP1 and 2A but also on the active and selective uptake mediated by OATP.

| MC-variant | OATP1B1 IC50[nM] | OATP1B3 IC50[nM] | Ratio 1B1 to 1B3 |
|---|---|---|---|
| LA | 0.5 | 2.5 | 0.2 |
| LW | 0.2 | 0.2 | .1 |
| LF | 0.4 | 0.9 | 0.4 |
| LR | 1 | 5.1 | 0.2 |
| RR | 3800 | 580 | 6.6 |
| YR | 90 | 45 | 2 |
| NOD | 8.40 | >100 | <0.1 |
| RY | 77 | 2.5 | 30.8 |
| HilR | 57 | 3.8 | 15 |
| RF | 58 | 3.4 | 17 |

Microcystins are difficult to synthesize chemically. One more convenient way of obtaining microcystins involves the in vivo production of microcystins by cyanobacteria.

Previous experiments of academic groups intended to increase product yields of naturally produced non-ribosomal peptides (here microcystins) by feeding of amino acids, which are incorporated in at least one structural variant of the respective microcystin synthesized by the fed strain. More specific, feeding of the amino acids leucine (L, Leu) or arginine (R, Arg) to a cyanobacterial strain that produces the microcystin (MC) variants MC-LR and MC-RR (L for leucine; R for arginine) influences the yield of both variants in dependence of the fed amino acid. Furthermore, feeding of amino acids which are incorporated in at least one structural variant of the respective microcystin synthesized by the fed strain might also influence biomass production.

In addition, it also has been shown that feeding of amino acids that represent slightly modified versions of the amino acids which are naturally incorporated into the respective non-ribosomal peptide produced by the fed strain might be also incorporated into the respective non-ribosomal peptide. This approach is generally known as mutasynthesis. For cyanobacterial non-ribosomal peptides, however, this approach has to date been restricted to simple analogs of natural amino acids such as homo-tyrosine instead of tyrosine (differing by only one methylene group) or halogenated amino acids (differing by only one halogen atom) such as chloro-tyrosine instead of tyrosine. Feeding of more extensively modified amino acids or of amino acids and their analogs that are different from the amino acids that are naturally incorporated into the non-ribosomal peptide have not been reported to date. Moreover, it has been described in the literature that feeding of modified amino acids to be incorporated into microcystins is not possible.

There is a need for modified non-ribosomal peptides from cyanobacteria including modified cytotoxins from cyanobacteria like for instance modified microcystins (e.g. in connection with the optimization of microcystin-based cancer lead compounds). There is a need for methods of producing non-ribosomal peptides like microcystins as well as coupling microcystins to targeting units (e.g. in connection with the construction of antibody-drug conjugates for targeted therapy of cancers, infection diseases, thrombosis and other kinds of targeted therapies).

SUMMARY OF INVENTION

The problem was solved by producing modified non-ribosomal peptides (e.g. microcystins, nodularins, anabaenopeptins, oscillamides, etc.) by means of incorporating one or more modified substrates into those non-ribosomal peptides.

The invention relates to a method of producing a modified non-ribosomal peptide from cyanobacteria, e.g. a modified microcystin and/or modified nodularin (together cytotoxic agents, CA), comprising the steps of:

a) growing a non-ribosomal peptide producing cyanobacteria strain in a culture media,
b) adding one or more modified substrates, preferably modified amino acids, to said culture, and
c) cultivating the strain in the presence of said modified substrates.

The invention relates to a modified non-ribosomal peptide comprising at least one modified amino acid, wherein the at least one modified amino acid comprises an anchor group directly accessible or chemically transformable for use in conjugation chemistry (incl. click chemistry), for the attachment of a targeting moiety and/or a label and/or for additional structural modifications.

Definitions

Herein, non-ribosomal peptides are a class of peptide secondary metabolites synthesized by non-ribosomal peptide synthetases, which, unlike the ribosomes, are independent of messenger RNA. Each non-ribosomal peptide synthetase can synthesize only one type of peptide. Non-ribosomal peptides often have cyclic and/or branched structures, can contain non-proteinogenic amino acids including D-amino acids, carry modifications like N-methyl and N-formyl groups, or are glycosylated, acylated, halogenated, or hydroxylated. Cyclization of amino acids against the peptide "backbone" is often performed, resulting in oxazolines and thiazolines; these can be further oxidized or reduced. On occasion, dehydration is performed on serines, resulting in dehydroalanine. This is just a sampling of the various manipulations and variations that non-ribosomal peptides can perform. Non-ribosomal peptides are often dimers or trimers of identical sequences chained together or cyclized, or even branched. Non-ribosomal peptides are a very diverse family of natural products with an extremely broad range of biological activities and pharmacological properties. They are often toxins, siderophores, or pigments. Non-ribosomal peptide antibiotics, cytostatics, and immunosuppressants are in commercial use.

In contrast to non-ribosomal peptides from other microbial producers cyanobacterial non-ribosomal peptides possess an extraordinary high number of structural variants within one class of non-ribosomal peptides (see table). Furthermore, many cyanobacteria produce hybrid structures of non-ribosomal peptides and polyketides. Consequently, the multienzyme complexes for those hybrid structures of non-ribosomal peptides and polyketides are also built up by a non-ribosomal peptide synthetase part and a polyketide synthase part. Herein, a non-ribosomal peptide can be also a hybrid of a non-ribosomal peptide and a polyketide (e.g. the compound class of microcystins).

TABLE

Selected classes of cyanobacterial non-ribosomal peptides (synonyms refer to names in original publications): The number of variants reflects the structural variability of known congeners in early 2005 (number for cryptophycins from 2017). In general the today's number of natural occurring variants of cyanobacterial non-ribosomal peptides is significantly higher.

| Class | Synonyms | Origin | No. of natural variants |
|---|---|---|---|
| microcystins | | *Anabaena*, *Hapalosiphon*, *Microcystis*, *Nostoc*, *Planktothrix* | 89 |
| nodularin | | *Nodularia* | 3 |
| aeruginosins | microcin, spumigin | *Microcystis*, *Planktothrix*, *Nodularia* | 27 |
| microginins | cyanostatin, oscillaginin, nostoginin | *Microcystis*, *Planktothrix*, *Nostoc* | 38 |
| anabaenopeptins | oscillamide, ferintoic acid, nodulapeptin, | *Anabaena*, *Aphanizomenon*, *Microcystis*, *planktothrix*, *Plectonema*, | 32 |

TABLE-continued

Selected classes of cyanobacterial non-ribosomal peptides (synonyms refer to names in original publications): The number of variants reflects the structural variability of known congeners in early 2005 (number for cryptophycins from 2017). In general the today's number of natural occurring variants of cyanobacterial non-ribosomal peptides is significantly higher.

| Class | Synonyms | Origin | No. of natural variants |
|---|---|---|---|
| | plectamide, schizopeptin | *Noduiaria*, *Schizothrix* | |
| cyanopeptolins | aeruginopeptin, anabaenopeptilide, dolastatin, hofmannolin, microcystilide, micropeptin, nostocyclin, planktopeptin, scyptolin, somamide, symplostatin, tasipeptin | *Anabaena*, *Lyngbya*, *Microcystis*, *Planktothrix*, *Scytonema*, *Symploca* | 82 |
| cyclamides | aanyascyclamide, dendroamide, microcyclamide, nostocyclamide, raocyclamide, tenuecyclamide, ulongamide, westiellamide | *Lyngbya*, *Microcystis*, *Nostoc*, *Oscillatoria*, *Stigonema*, *Westelliopsis* | 21 |
| cryptophycine | | *Nostoc* | >25 (2017) |

TABLE

Natural occurring cryptophycins

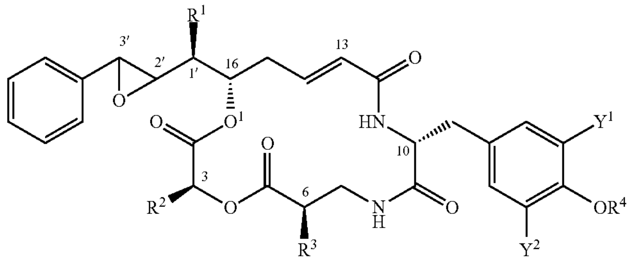

epoxides

| Compound | Epoxide | $R^1$ | $R^2$ | $R^3$ | $R^4$ | $Y^1$ | $Y^2$ | C13═C14 |
|---|---|---|---|---|---|---|---|---|
| C-1 | β | Me | i-Bu | Me | Me | Cl | H | trans |
| C-2 | β | Me | i-Bu | Me | Me | H | H | trans |
| C-16 | β | Me | i-Bu | Me | H | Cl | H | trans |
| C-21 | β | Me | i-Bu | H | Me | Cl | H | trans |
| C-23 | β | Me | i-Bu | Me | H | Cl | Cl | trans |
| C-24 | β | Me | i-Bu | H | Me | H | H | trans |
| C-28 | β | H | i-Bu | Me | Me | Cl | H | trans |
| C-31 | β | Me | i-Bu | Me | Me | Cl | Cl | trans |
| C-38 | α | Me | i-Bu | Me | Me | Cl | H | trans |
| C-50 | β | Me | n-Pr | Me | Me | Cl | H | trans |
| C-54 | β | Me | s-Bu | Me | Me | Cl | H | trans |
| C-176 | β | Me | i-Bu | H | H | Cl | H | trans |
| C-326 | β | Me | i-Bu | H | Me | Cl | Cl | trans |
| C-327 | β | Me | i-Bu | Me | Me | Cl | H | cis |

TABLE-continued

Natural occurring cryptophycins

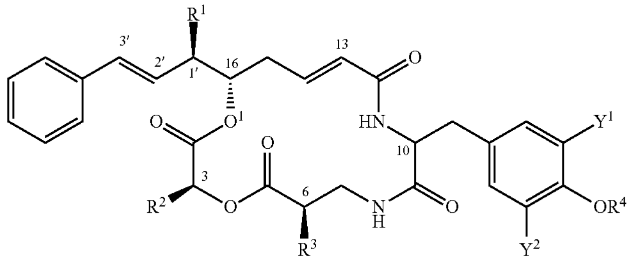

olefins

| Compound | $R^1$ | $R^2$ | $R^3$ | Config. at C10 | $R^4$ | $Y^1$ | $Y^2$ |
|---|---|---|---|---|---|---|---|
| C-3 | Me | i-Bu | Me | R | Me | Cl | H |
| C-4 | Me | i-Bu | Me | R | Me | H | H |
| C-17 | Me | i-Bu | Me | R | H | Cl | H |
| C-18 | Me | s-Bu | Me | R | Me | Cl | H |
| C-19 | Me | i-Pr | Me | R | Me | Cl | H |
| C-29 | Me | i-Bu | H | R | Me | Cl | H |
| C-40 | H | i-Bu | Me | R | Me | Cl | H |
| C-43 | Me | i-Bu | Me | R | H | H | H |
| C-45 | Me | i-Bu | Me | R | H | Cl | Cl |
| C-46 | Me | i-Bu | Me | S | Me | Cl | H |
| C-49 | Me | n-Pr | Me | R | Me | Cl | H |
| C-175 | Me | i-Bu | Me | R | Me | Cl | Cl |

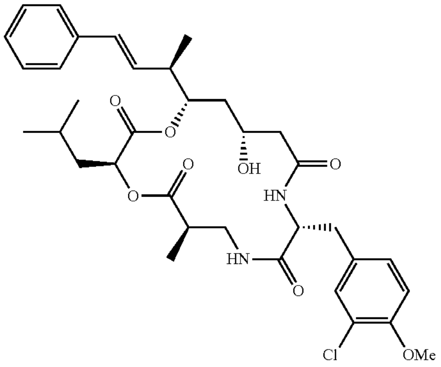

C-30

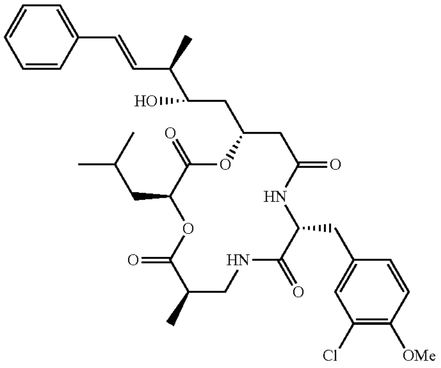

C-26

Herein, a microcystin according to the invention has the general structure of D-$Ala_1$-$X_2$-D-$MeAsp_3$-$Z_4$-$Adda_5$-D-$Glu_6$-$Mdha_7$, where structural variations may in principle occur at all positions but most frequently at X and Z (see FIG. 1). These are the variable L-amino acids. D-MeAsp is D-erythro-b-methyl aspartic acid, Mdha is N-methyldehydroalanine, and Adda is 3-amino-9-methoxy-2,6,8-trimethyl-10-phenyldeca-4,6-dienoic acid. Demethylation at position 3 and/or 7 and methylation at position 6 is also within the scope of the invention as well as further modifications at the position 1, 5 and 7 as indicated in FIG. 1.

Herein we demonstrate multiple combinations of the variable L-amino acids (X and Z) in positions 2 and 4 and modifications in the other D-amino acids.

Herein, a nodularin is a monocyclic pentapeptide consisting of cyclo[-D-erythro-methylAsp (iso-linkage)-L-Arg-Adda-D-Glu(iso-linkage)-Mdhb], where Mdhb stands for N-methyldehydrobutyrate and Adda is the particular C20-amino acid: 3-amino-9-methoxy-2,6,8-trimethyl-10-phenyl-deca-4,6-dienoic acid whereas all positions can naturally be slightly modified as indicated in FIG. 1. Nodularin closely resembles microcystins with respect to structure and biological activity.

Modifications of microcystins and nodularins shall not occur at the position for Adda and D-Glu as these two positions are essential for the inhibiting activity against PP1 and PP2A.

Herein, microcystin and nodularin as well as further cytotoxic non-ribosomal peptides from cyanobacteria in all their modified variations are referred to as cytotoxic agents, or CA (see table with selected cytotoxic non-ribosomal peptides from cyanobacteria).

TABLE

Selected cytotoxic non-ribosomal peptides from cyanobacteria with often a new mode of action.

| compound | source | cytotoxic potency | mode of action | biological target | clinical effect |
|---|---|---|---|---|---|
| Monomethyl auristatin E | synthetic analogue of Dolastatin 10 from *Symploca hydnoides* | 3.9-10.3 nM (human tumor cell lines) | inhibition of beta-Tubulin polymerization | spindle apparatus | antiproliferative/ cytotoxic |
| Largarzole | *Symploca* sp. | 7.7 nM pM for derivate | New: modulation of DNA - Histone interaction; alteration of gene expression | class I histone deacetylases (selective) | antiproliferative/ osteogenic |
| Apratoxin | *Lyngbya majuscula* | 360 pM | New: Inhibition of co-translational translocation of cancer-associated receptors and growth factors | secretory pathways | antiproliferative |
| Hectochlorin | *Lyngbya majuscula* | 20 nM | hyperpolymerization of actin | actin | antiproliferative |
| Aurilides | *Lyngbya* sp. | >10 nM | New: enhanced proteolytic processing of optic atrophy 1 (OPA1) protein | Prohibitin 1 (PHB1) inhibtion | antiproliferative |
| Bisebromoamide | *Lyngbya* sp. | 40 nM | New: inhibition of PDGF-initiated signaling | kinase signaling pathway (attenuated phosphorylation of ERK) | antiproliferative |
| Grassypeptolide | *Lyngbya confervoide* | pM-µM | Likely new MoA | dipeptidyl peptidase 8 (DPP8) + other | antiproliferative |
| Carmaphycine | *Symploca* sp. | nM range | New: intracellular accumulation of misfolded proteins | Inhibition of b5 Subunit activity of 20S proteasom | antiproliferative |
| Symplocamide | *Symploca* sp. | <40 nM | TBD | TBD | antiproliferative |
| Lagunamide | *Lyngbya majuscula* | 2 nM | New: enhanced proteolytic processing of optic atrophy 1 (OPA1) protein | prohibitin 1 (PHB1) inhibition | antiproliferative |
| Cryptophycin | *Nostoc* sp. | <10 pM | microtubule disrupting agent; tubulin polymerization | vinca domain of tubulin | antiproliferative |
| Coibamide | *Leptolyngbya* sp. | <10 nM | New: Likely the same as for Apratoxin | secretory pathways | antiproliferative |
| Curacin A | *Lyngbya majuscula* | <9 nM | G2/M cell cycle arrest | microtubuli | antiproliferative |
| Desmethoxymajusculamide | *Lyngbya majuscula* | 20 nM | actin depolymer-isation | actin | antiproliferative |

Herein, a CA producing cyanobacterial strain is referred to as a CA-STRAIN.

Herein, anabaenopeptin and oscillamide are cyclic peptides that are characterized by a lysine in position 5 and the formation of the ring by an N-6-peptide bond between Lys and the carboxy group of the amino acid in position 6. A side chain of one amino acid unit is attached to the ring by an ureido bond formed between the a-N of Lys and the a-N of the side chain amino acid. All other positions in the ring and side chain are variable.

Herein targeting moieties are proteins (mainly antibodies and their fragments), peptides, nucleic acids (aptamers), small molecules, or others (vitamins or carbohydrates) as well as nano particles. Monoclonal antibodies (mAbs) are preferred as escort molecules for the targeted delivery of the altered and modified non-ribosomal peptides incl. altered and modified microcystins or nodularins. However, small molecules can also act as targeting moieties as they might influence the physicochemical properties of said peptides. One example for this is the coupling with hydrophilic moieties such as sugars, e.g. to increase the solubility of said peptide in water. Furthermore, the attached small molecule can have the purpose of altering the peptides in vivo pharmacokinetic properties, e.g. attachment of a functional group prone to in vivo metabolism can increase hepatic clearance and reduce hepatic toxicity, or can influence transporter selectivity and therefore the (active) uptake of the modified non-ribosomal peptide by cells.

Herein an ADC (ADC for antibody-drug conjugate) is a CA linked to a targeting moiety (TM) directly or via a linker (L) whereas by definition of an ADC the targeting moiety is an antibody The term antibody (AB) herein is used in the broadest sense and specifically covers monoclonal antibodies, polyclonal antibodies, dimers, multimers, multispecific antibodies (e.g., bispecific antibodies), and antibody fragments, so long as they exhibit the desired biological activity. Antibodies may be murine, human, humanized, chimeric, or derived from other species. An antibody is a protein generated by the immune system that is capable of recognizing and binding to a specific antigen. A target antigen generally has numerous binding sites, also called epitopes, recognized by complementarity-determining regions (CDRs) on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immuno-specifically binds an antigen of a target of interest or part thereof, such targets including but not limited to, cancer cells, microbial cells or cells that produce autoimmune antibodies associated with an autoimmune disease. The immuno globulin can be of any type (e.g., IgG, IgE, IgM, IgD, and IgA), class (e.g., IgGI, IgG2, IgG3, IgG4, IgA1 and IgA2) or subclass of immunoglobulin molecule. The immunoglobulins can be derived from any species, including human, murine, or rabbit origin.

Antibody fragments (AB fragments) comprise a portion of a full length antibody, generally the antigen binding or variable region thereof. Examples of antibody fragments include Fab, Fab', F(ab')2, and Fv fragments; diabodies; linear antibodies; fragments produced by a Fab expression library, anti-idiotypic (anti-Id) antibodies, CDR (complementary determining region), and epitope-binding fragments of any of the above which immuno-specifically bind to cancer cell antigens, viral antigens or microbial antigens, single-chain antibody molecules; multi-specific antibodies formed from antibody fragments.

The linker, attaches the antibody or AB fragment or targeting moiety or label to the CA through covalent bond(s). The linker is a bifunctional or multifunctional moiety which can be used to link one or more drug moiety (D whereas D=CA) and an antibody unit (Ab) to form antibody-drug conjugates (ADC). The linker (L) may be stable outside a cell, i.e. extracellular, or it may be cleavable by enzymatic activity, hydrolysis, or other metabolic conditions. Antibody-drug conjugates (ADC) can be conveniently prepared using a linker having reactive functionality for binding to the drug moiety (here the CA) and to the antibody. Herein, the ADC is a CA linked to a targeting moiety. A linker can also include a spacer that might be of advantage to obtain favorable spacial distances between the linker, drug and targeting moieties.

A cysteine thiol, an amine, e.g. N-terminus or amino acid side chain such as lysine, or any other modification of the antibody (AB), as described below, can form a bond with a functional group of a linker reagent, drug moiety (D) or drug-linker reagent (D-L). The linkers are preferably stable extracellularly. Before transport or delivery into a cell, the antibody-drug conjugate (ADC) is preferably stable and remains intact, i.e. the antibody remains linked to the drug moiety. The linkers are stable outside the target cell and may be cleaved at some rate inside the cell. An effective linker will: (i) maintain the specific binding properties of the antibody; (ii) allow intracellular delivery of the conjugate or drug moiety; (iii) remain stable and intact, i.e. not cleaved, until the conjugate has been delivered or transported to its targeted site; and (iv) maintain a cytotoxic, cell-killing effect or a cytostatic effect of the CA. Stability of the ADC may be measured by standard analytical techniques such as mass spectroscopy, HPLC, and the separation/analysis technique LC/MS. Covalent attachment of the antibody and the CA requires the linker to have two reactive functional groups, i.e. bivalency in a reactive sense. Bivalent linker reagents which are useful to attach two or more functional or biologically active moieties, such as peptides, nucleic acids, drugs, toxins, antibodies, haptens, and reporter groups are known.

In another embodiment, the linker may be substituted with a sulfonate substituent or other substituents which may increase water solubility of the reagent and facilitate the coupling reaction of the linker reagent with the antibody or the CA, or facilitate the coupling reaction of AB-L with D, or D-L with AB, depending on the synthetic route employed to prepare the ADC. Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties, linker reagents and CA (=D) including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non native cysteine amino acid residues). US 2007/0092940 engineering antibodies by introduction of reactive cysteine amino acids.

Modified substrate means any amino acid and any related compound carrying at least one amino group and one carboxyl group that enable peptide bound formation of the modified substrate in a respective non-ribosomal peptide and which is naturally not incorporated into the non-ribosomal peptides synthesized by a specific cyanobacterial strain.

A modified amino acid or modified substrate may comprise an amino acid linker component including those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, cathepsin B, C and D, or a plasmin protease. Amino acid side chains include those occurring naturally, as well as minor amino acids and non-naturally occurring amino acid analogs, such as citrulline.

BRIEF DESCRIPTION OF DRAWINGS

FIG. 31: Exemplary embodiment No. 19: Incorporation of the modified substrate Prg-Tyr (Tyr=Tyrosine) into Cryptophycin 1 produced by strain CBT 567. Extracted ion chromatogram from HPLC-MS data of mass value of protonated molecular ion of novel Cryptophycin variant for sample of control cultivation (a) and sample of cultivation with added modified substrate (b) in the positive ionization mode. Finally, c) shows the averaged mass spectrum of the additional peak in chromatogram b). Detector signal intensities (y-Axis) are measured in counts (dimensionless quantity).

FIG. 32: Exemplary embodiment No. 20: Produced ADCs and results of analytical SEC-HPLC. In analytical SEC-HPLC the conjugates Microcystin-ADC1 and Microcystin-ADC2 showed a high level of purity with 98.9% and 99.0% monomers. In both cases, aggregates and small fragments were detected with rates of 0.8% and 0.2%.

FIG. 33: Exemplary embodiment No. 21: Coomassie stained Gelelectrophoresis gels demonstrating the binding of Microcystin variants 1 and 2 as payloads on monoclonal antibodies. In Coomassie staining under reducing conditions all samples showed a signal for the heavy chain at app. 50 kDa and the light chain at app. 25 kDa. All conjugates showed an up-shift of the protein signal of the heavy and the light chain compared to the naked MAB indicating toxin conjugation to both antibody chains. For all ADCs a double-signal was detected for the light chain indicating both, conjugated and unconjugated species. In Coomassie staining under non-reducing conditions the naked antibody showed a double signal at app. 150 kDa for the intact antibody. The ADCs showed a variety of signals between 25 kDa and 150 kDa, since in both cases the toxin was conjugated to reduced interchain disulfides leading to instability of the antibody during incubation at 37° C.

FIG. 34: Exemplary embodiment No. 22: Successful in vitro proof of concept of Microcystin-based ADCs. The cell viability is monitored in an in-vitro-assay with a cancer cell line for the different concentrations of the Microcystin ADC for two Microcystin variants as payloads. The ADC carries a non-cleavable linker. For Microcystin-ADC-2 an $EC_{50}$ values of 220 pM was determined. Differences between structural payload variants underline huge potential of further structural optimizations.

DETAILED DESCRIPTION OF THE INVENTION

The invention relates to a method of producing a modified non-ribosomal peptide, especially cytotoxic non-ribosomal peptides such as modified microcystin and/or modified nodularin (both CA), comprising the steps of:

a) growing a microcystin and/or nodularin producing cyanobacteria strain (CA-STRAIN) in a culture media,
b) adding one or more modified substrates preferably modified amino acids to said culture, and
c) cultivation the strain in the presence of said modified substrates.

The invention relates to a method of producing a modified non-ribosomal peptide from cyanobacteria, comprising the steps of:

a) growing a non-ribosomal peptide producing cyanobacteria strain in culture media,
b) adding one or more modified substrates to said culture, and
c) growing the strain in the presence of said modified substrates,
d) wherein the modified substrate, is either
    i) a modified amino acid, which comprises an anchor group directly accessible or transformable for use in conjugation chemistry incl. click chemistry, for the attachment of a targeting moiety or a label, or a linker or for any other structural modification
    ii) or, the modified substrate in the non-ribosomal peptide is a modified substrate which is not directly derived from the naturally incorporated substrate, such as preferably an amino acid or a modified amino acid which is, in nature, not incorporated at the specific position in said non-ribosomal peptide and which is also not a substitution of the naturally incorporated substrate with functional groups which are not directly accessible or transformable for use in conjugation chemistry incl. click chemistry, for the attachment of a targeting moiety or a label.

In the first option the modified substrate carries an anchor group directly accessible or transformable for use in conjugation chemistry incl. click chemistry, for the attachment of a targeting moiety or a label or a linker or for any other structural modification of the non-ribosomal peptide. This will allow for example connecting antibodies to the CA.

In the second option the modified substrate allows for the generation of new CAs wherein the CA carries an amino acid in the CA at a position where, in nature such an amino acid does not exist and which is also not a substitution of the naturally incorporated substrate with functional groups which are not directly accessible or transformable for use in conjugation chemistry. The amino acid may be modified. This allows for the creation of great compound libraries with CAs with novel structures.

Figure 35:
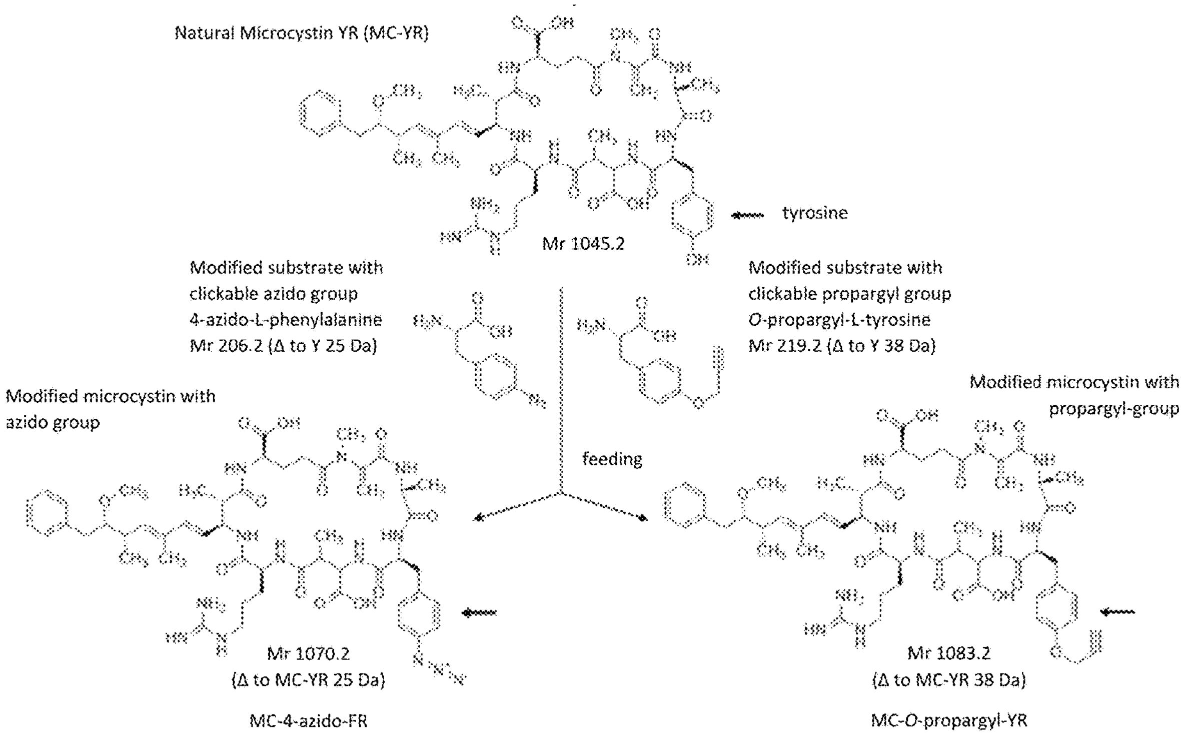
FIG. 35: General principle of feeding modified substrates which comprise an anchor group directly accessible or transformable for use in conjugation chemistry incl. click chemistry, for the attachment of a targeting moiety or a label, or a small organic molecule or a linker or any other structural modification.

FIG. 35 illustrates the general principle of the invention using the example of producing a modified microcystin YR (MC-YR) by feeding either the modified substrate 4-azido-L-phenylalanine carrying a clickable azido group as anchor group (left side of the figure) or by feeding the modified substrate 0-propargyl-L-tyrosine carrying the clickable propargyl group (also known as alkyne group) as anchor group (left side of the figure). Both substrates with their respective clickable anchor groups lead to replacement of the tyrosine at position 2 (see arrow in the upper chemical structure). In case of feeding of 4-azido-L-phenylalanine the resulting modified microcystin is MC-4-azido-FR (F L-phenylalanine; R for arginine). In case of feeding of O-propargyl-L-tyrosine the resulting modified microcystin is MC-O-propargyl-YR (Y for tyrosine; R for arginine). The generation of both modified microcystins can be detected on the basis of their molecular mass by using mass spectrometry (MS).

Figure 36:
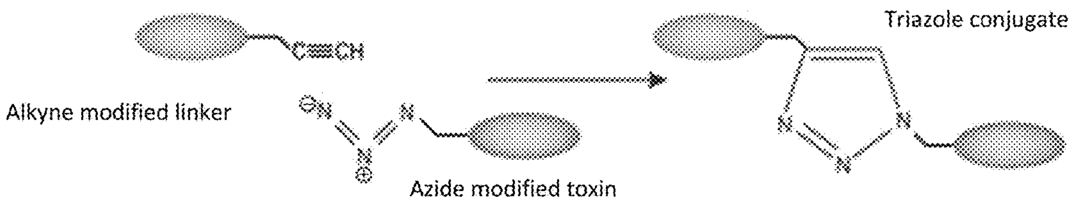
FIG. 36: Illustration of click chemistry reaction between an alkyne modified linker and an azide modified toxin forming a triazole conjugate. Both groups represent potential anchor groups.

The two anchor groups (the azido group and the propargyl group, also known as alkyne group) of the two modified microcystins described above can be directly used for conjugation chemistry, more specific for click chemistry. Hereby the respective click reaction is based on the reaction between these two groups with each other. That means an azido group reacts with a propargyl group (alkyne group) forming a triazole conjugate as shown in FIG. 36. Therefore both groups the azido group and the propargyl (alkyne) group can be used as anchor groups of modified substrates.

The selection of a suitable strain for the feeding of modified substrates needs to be identified by screening (feeding experiments with a high number of diverse modified substrates incl. the use and variation of strain-specific cultivation conditions for a high number of strains). Such screening is preferably done in small scale cultures (e.g. in 1.6 ml to 10 ml scale) in order to assure throughput and efficiency. In addition the detection of modified non-ribosomal peptides is preferably done by mass spectrometry (MS) whereas the MS method is preferably suited for analyses of small scale cultures without the need of extensive extractions and sample preparations, e.g. MALDI-ToF-MS (see FIG. 2).

In the context of the establishment of a screening for strains that can be fed with modified substrates for the generation of novel non-ribosomal peptides the inventors found that feeding of O-methyl-tyrosine and homo-arginine at the same time to a strain producing MC-YR and MC-LR (Y—for tyrosine; R—for arginine; L for leucine) resulted in the incorporation of O-methyl-tyrosine instead of tyrosine and the incorporation of homo-arginine instead of arginine. Consequently, by feeding of these two modified amino acids the fed strain additionally produced MC-Y-homo-R, MC-O-methyl-YR, MC-O-methyl-Y-homo-R, and MC-L-homo-R (see FIG. 2).

Furthermore the selection of suitable substrates for feedings is ideally done based on non-ribosomal peptides naturally produced by a specific strain, e.g. naturally produced microcystins and nodularins. Hereby not only substrates which are directly derived from the native substrates can be selected.

The fact that strains might produce several structural variants with different amino acids at a specific position of the non-ribosomal peptide significantly increases the number of suitable substrates. This counts even more if a strain naturally produces variants with structurally distant amino acids at a specific position, e.g. the *Microcystis* strain CBT 480 primarily produces MC-LR and MC-YR as major microcystins in comparable amounts (besides further structural variants produced in minor amounts), although the hydrophobic aliphatic amino acid leucine (L) is structurally rather distant from the aromatic amino acid tyrosine (Y).

Interestingly, by genome sequencing of said strain *Microcystis* CBT 480 the inventors found that despite the fact that the two major microcystin variants MC-LR and MC-YR are synthesized by this strain, there is only one microcystin synthetase gene cluster encoded in the genome of said *Microcystis* strain CBT480. Subsequent DNA sequence comparison with another microcystin synthetase gene cluster from *Microcystis* strain CBT265 (also PCC7806) which primarily produces MC-LR did not reveal significant sequence differences which might explain the differences in the abundance of microcystin variants produced by both strains (see FIG. 3). This leads the inventors to the conclusion that the feature of being a suited strain for the generation of modified non-ribosomal peptides by feeding of modified substrates is not solely connected to the multienzyme complex of the non-ribosomal peptide synthetase encoded by the respective gene cluster. It is rather a strain-specific feature which needs to be screened for in an approach of cultivation of a high number of strains using strain-specific conditions, feeding of a high number of modified substrates to the strains and analyzing of the resulting secondary metabolite spectra of fed strains (see FIG. 2) by mass spectrometry (MS).

Therefore the inventors conclude, that preferably, the strain is selected by cultivation/feeding/chemical analysis screening and the chemical structures of the produced non-ribosomal peptides are known such that the suited modified substrates can be selected and the incorporation of the modified substrate into the non-ribosomal peptide during cultivation occurs at a defined position.

Preferable cyanobacterial strains can be of a variety of suitable genera, including but not limited to genera of the group comprising *Microcystis, Planktothrix, Oscillatoria, Nostoc, Anabaena, Aphanizomenon, Hapalosiphon, Nodularia, Lyngbya, Phormidium, Spirulina, Halospirulina, Arthrospira, Trichodesmium, Leptolyngbya, Plectonema, Myxosarcina, Pleurocapsa, Pseudanabaena, Geitlerinema, Euhalothece, Calothrix, Tolypothrix, Scytonema, Fischerella, Mastigocladus, Westiellopsis, Stigonema, Chlorogloeopsis, Cyanospira, Cylindrospermopsis, Cylindrospermum, Microchaete, Rivularia, Autosira, Trichonema, Trichodesmium, Symploca, Starria, Prochlorothrix, Microcoleus, Limnothrix, Crinalium, Borzia, Chroococcidiopsis, Cyanocystis, Dermocarpella, Staniera, Xenococcus, Chamaesiphon, Chroococcus, Cyanobacterium, Cyanobium, Cyanothece, Dactylococcopsis, Gloeobacter, Gloeocapsa, Gloeothece*. The only pre-requisite for strains to be used by the here described method is the synthesis of a least one non-ribosomal peptide by the respective strain.

Preferably the non-ribosomal peptide(s) produced by the cyanobacterial strain can be a variety of CA, including but not limited to cytotoxic non-ribosomal peptides of the group comprising microcystins, nodularins, cryptophycins, largarzoles, apratoxins, hectochlorines, aurilides, bisebromoamides, grassypeptolides, carmaphycins, symplocamides, lagunamides, coibamides, desmethoxy-majusculamides, curacins or it can be a non-ribosomal peptide with another bioactivity including but not limited to bioactive non-ribosomal peptides of the group comprising aeruginosins (synonyms: microcin, spumigin), microginins (synonyms: cyanostatin, oscillaginin, nostoginin), anabaenopeptins (oscillamide, ferintoic acid, nodulapeptin, plectamide, schizopeptin), cyanopaptolins (synonyms: aeruginopeptin, anabaenopeptilide, dolostatin, hofmannoline, microcystillide, micropeptin, nostocyclin, nostopeptin, oscillapeptilide, oscillapeptin, planctopeptin, scyptolin, somamide, symplostatin, tasipeptin), cyclamides (synonyms: aanyascyclamide, dendroamide, microcyclamide, nostocyclamide, raocyclamide, tenuecycyclamide, ulongamide, westiellamide. The term in this list refers to names in original publications.

Preferably, the modified substrate is a modified amino acid. Preferably, the modified substrate allows for conjugation chemistry (incl. click chemistry).

The modified substrate allows for a broad diversity of functional groups being placed into the non-ribosomal peptide, e.g. the CA for coupling to the label or targeting moiety, etc.

Preferably, it allows for conjugation chemistry including click chemistry whereas conjugation chemistry is characterized as all chemical reactions that are able to join together two molecules with functional groups that can react with each other and whereas click chemistry is characterized as chemical reactions with a high thermodynamic driving force that drives it quickly and irreversibly to high yield of a single reaction product, with high reaction specificity (in some cases, with both regio- and stereo-specificity) generating minimal and inoffensive byproducts. Click reactions are not disturbed by water. These qualities make click reactions (beside other, e.g. diagnostic applications) particularly suitable to the problem of an efficient and site-specific coupling of drug-like molecules at different positions of the drug and with different click chemistry to different positions of monoclonal antibodies via suited linker peptides or without linkers in order to create the ADC for the targeted treatment of diseases such as cancer, infection diseases, thrombosis and other diseases and disorders.

Figure 25:
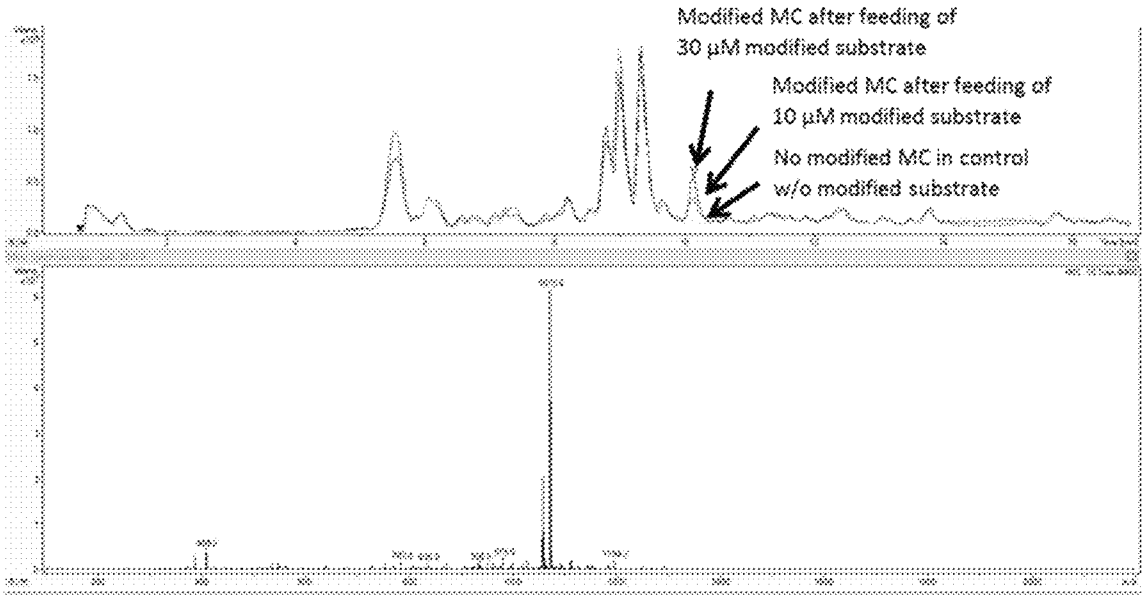
FIG. 25: Exemplary embodiment No. 13: Feeding of *Microcystis aeruginosa* strain CBT 480 with different amounts of modified substrate 4-azido-L-phenylalanine (0 μM, 10 μM, 30 μM) results an increasing amount of produced modified microcystin with increasing amount of fed modified substrate 4-azido-L-phenylalanine. This result allows for optimization of feeding protocols for respective productions of modified non-ribosomal peptides (here modified microcystins). The upper part of the figure shoes overlaid HPLC-PDA Chromatograms at 238 nm for sample of control cultivation, sample of cultivation with added substrate 4-azido-L-phenylalanine of 10 μM in culture medium and sample of cultivation with added substrate 4-azido-L-phenylalanine of 30 μM in culture medium. The lower figure shows the averaged mass spectrum of the newly formed peak visible at about 10 min in the HPLC chromatogram. Detector signal intensities (y-Axis) are measured in milli-absorption units (mAU) and counts (dimensionless quantity) for PDA and mass spectrometry data, respectively.
Figure 26A:
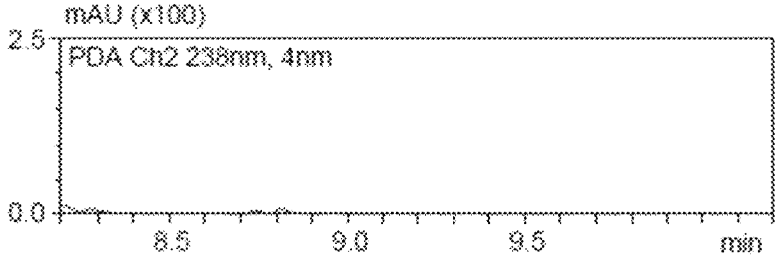
FIG. 26*a*: Exemplary embodiment No. 14: Incorporation of the modified substrate Prg-Tyr (Tyr=Tyrosine) into (D-$Asp^3$, E-$Dhb^7$) Microcystin-RR in position 2 produced by strain CBT 280. HPLC-PDA Chromatogram at 238 nm for sample of control cultivation. Detector signal intensities (y-Axis) are measured in milli-absorption units (mAU) and counts (dimensionless quantity) for PDA and mass spectrometry data respectively.
Figure 26B:
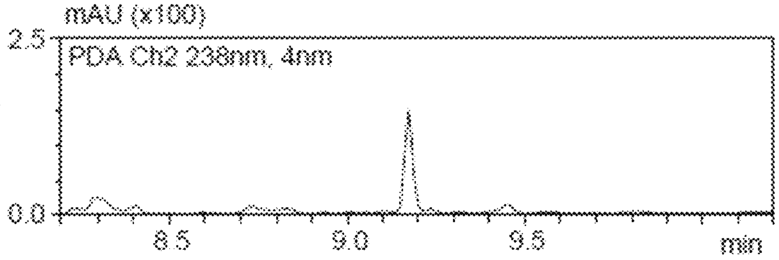
FIG. 26*b*: Exemplary embodiment No. 14: Incorporation of the modified substrate Prg-Tyr (Tyr=Tyrosine) into (D-$Asp^3$, E-$Dhb^7$) Microcystin-RR in position 2 produced by strain CBT 280. HPLC-PDA Chromatogram at 238 nm for sample of cultivation with added modified substrate. Detector signal intensities (y-Axis) are measured in milli-absorption units (mAU) and counts (dimensionless quantity) for PDA and mass spectrometry data respectively.
Figure 26C:
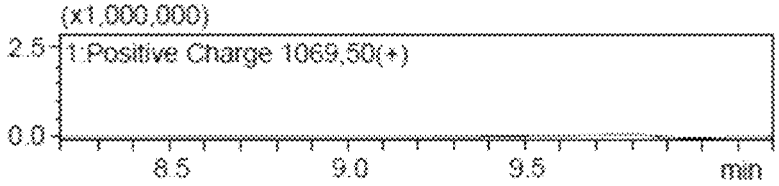
FIG. 26*c*: Exemplary embodiment No. 14: Incorporation of the modified substrate Prg-Tyr (Tyr=Tyrosine) into (D-$Asp^3$, E-$Dhb^7$) Microcystin-RR in position 2 produced by strain CBT 280. Extracted ion chromatogram from HPLC-MS data of mass value of protonated molecular ion of novel Microcystin variant for sample of control cultivation in the positive ionization mode. Detector signal intensities (y-Axis) are measured in milli-absorption units (mAU) and counts (dimensionless quantity) for PDA and mass spectrometry data respectively.
Figure 26D:
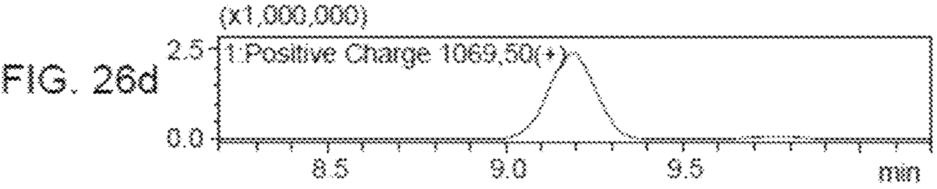
FIG. 26*d*: Exemplary embodiment No. 14: Incorporation of the modified substrate Prg-Tyr (Tyr=Tyrosine) into (D-$Asp^3$, E-$Dhb^7$) Microcystin-RR in position 2 produced by strain CBT 280. Extracted ion chromatogram from HPLC-MS data of mass value of protonated molecular ion of novel Microcystin variant for sample of cultivation with added modified substrate in the positive ionization mode. Detector signal intensities (y-Axis) are measured in milli-absorption units (mAU) and counts (dimensionless quantity) for PDA and mass spectrometry data respectively.
Figure 26E:
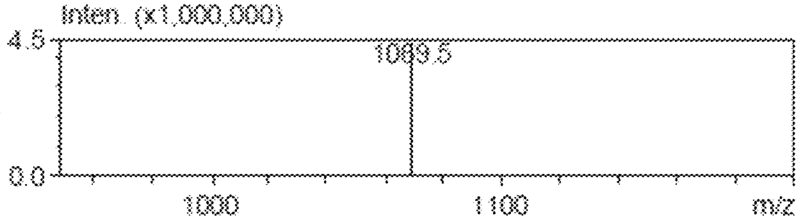
FIG. 26*e*: Exemplary embodiment No. 14: Incorporation of the modified substrate Prg-Tyr (Tyr=Tyrosine) into (D-$Asp^3$, E-$Dhb^7$) Microcystin-RR in position 2 produced by strain CBT 280. (e) shows the averaged mass spectrum of the peak visible in chromatogram (d).
Figure 27A:
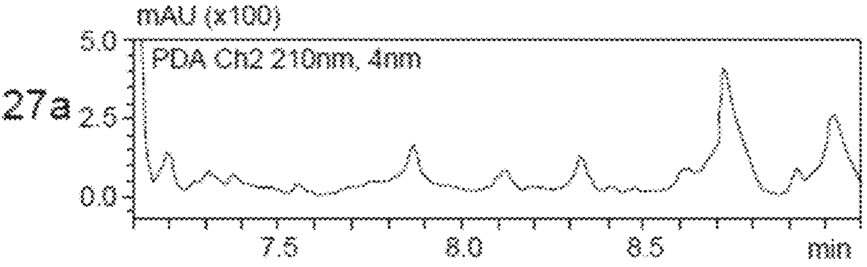
FIG. 27*a*: Exemplary embodiment No. 15: Incorporation of the modified substrate Prg-Tyr (Tyr=Tyrosine) into Anabaenopeptin A in position 2 produced by strain CBT 280. HPLC-PDA Chromatogram at 210 nm for sample of control cultivation. Detector signal intensities (y-Axis) are measured in milli-absorption units (mAU) and counts (dimensionless quantity) for PDA and mass spectrometry data respectively.
Figure 27B:
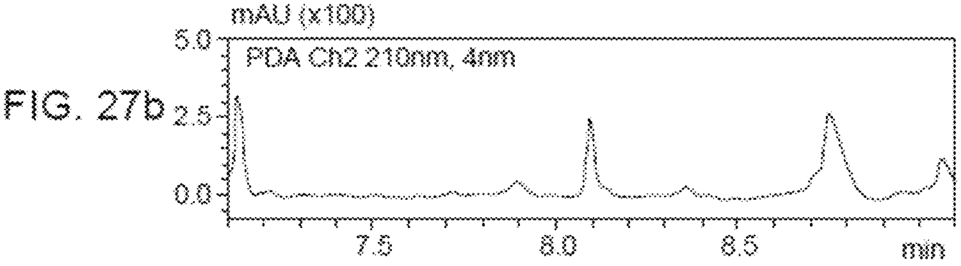
FIG. 27*b*: Exemplary embodiment No. 15: Incorporation of the modified substrate Prg-Tyr (Tyr=Tyrosine) into Anabaenopeptin A in position 2 produced by strain CBT 280. HPLC-PDA Chromatogram at 210 nm for sample of cultivation with added modified substrate. Detector signal intensities (y-Axis) are measured in milli-absorption units (mAU) and counts (dimensionless quantity) for PDA and mass spectrometry data respectively.
Figure 27C:
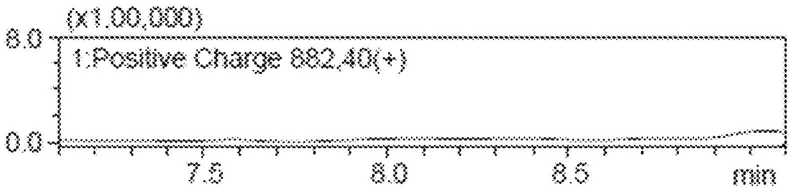
FIG. 27*c*: Exemplary embodiment No. 15: Incorporation of the modified substrate Prg-Tyr (Tyr=Tyrosine) into Anabaenopeptin A in position 2 produced by strain CBT 280. Extracted ion chromatogram from HPLC-MS data of mass value of protonated molecular ion of novel Anabaenopeptin variant for sample of control cultivation in the positive ionization mode. Detector signal intensities (y-Axis) are measured in milli-absorption units (mAU) and counts (dimensionless quantity) for PDA and mass spectrometry data respectively.
Figure 27D:
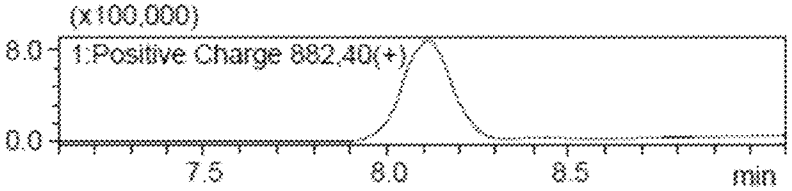
FIG. 27*d*: Exemplary embodiment No. 15: Incorporation of the modified substrate Prg-Tyr (Tyr=Tyrosine) into Anabaenopeptin A in position 2 produced by strain CBT 280. Extracted ion chromatogram from HPLC-MS data of mass value of protonated molecular ion of novel Anabaenopeptin variant sample of cultivation with added modified substrate in the positive ionization mode. Detector signal intensities (y-Axis) are measured in milli-absorption units (mAU) and counts (dimensionless quantity) for PDA and mass spectrometry data respectively.
Figure 27E:
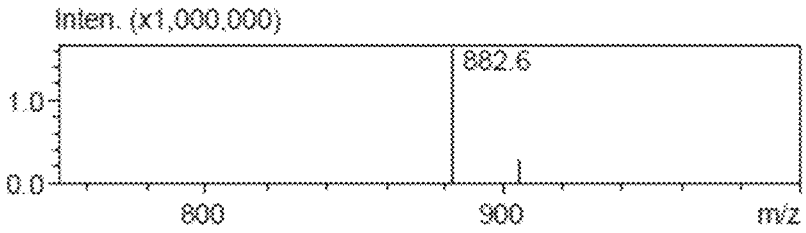
FIG. 27*e*: Exemplary embodiment No. 15: Incorporation of the modified substrate Prg-Tyr (Tyr=Tyrosine) into Anabaenopeptin A in position 2 produced by strain CBT 280. (e) shows the averaged mass spectrum of the peak visible in chromatogram (d).
Figure 28A:
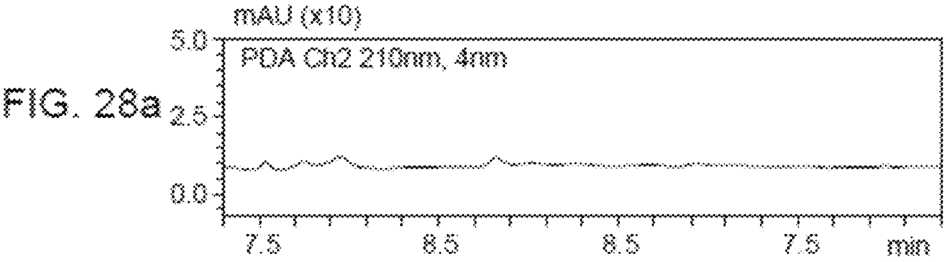
FIG. 28*a*: Exemplary embodiment No. 16: Incorporation of the modified substrate Azido-Phe (Phe=Phenylalanine) into Anabaenopeptin NZ857 produced by strain CBT 332. HPLC-PDA Chromatogram at 210 nm for sample of control cultivation. Detector signal intensities (y-Axis) are measured in milli-absorption units (mAU) and counts (dimensionless quantity) for PDA and mass spectrometry data respectively.
Figure 28B:
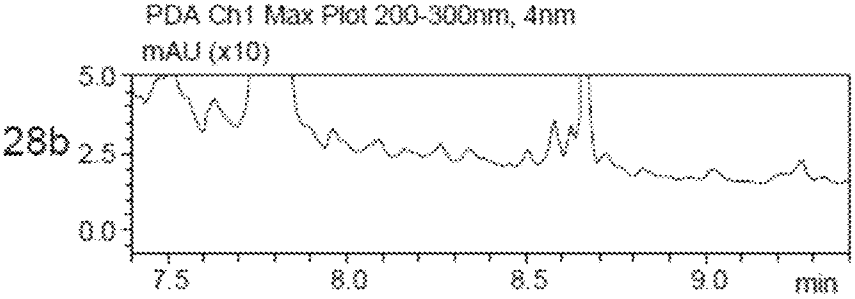
FIG. 28*b*: Exemplary embodiment No. 16: Incorporation of the modified substrate Azido-Phe (Phe=Phenylalanine) into Anabaenopeptin NZ857 produced by strain CBT 332. HPLC-PDA Chromatogram at 210 nm for sample of cultivation with added modified substrate. Detector signal intensities (y-Axis) are measured in milli-absorption units (mAU) and counts (dimensionless quantity) for PDA and mass spectrometry data respectively.
Figure 28C:
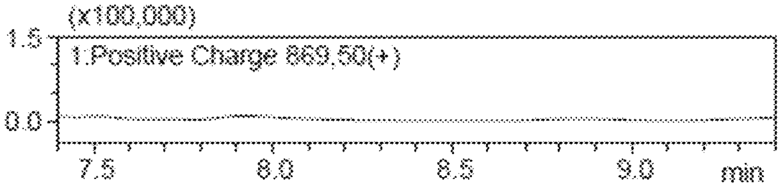
FIG. 28*c*: Exemplary embodiment No. 16: Incorporation of the modified substrate Azido-Phe (Phe=Phenylalanine) into Anabaenopeptin NZ857 produced by strain CBT 332. Extracted ion chromatogram from HPLC-MS data of mass value of protonated molecular ion of novel Anabaenopeptin variant for sample of control cultivation in the positive ionization mode. Detector signal intensities (y-Axis) are measured in milli-absorption units (mAU) and counts (dimensionless quantity) for PDA and mass spectrometry data respectively.
Figure 28D:
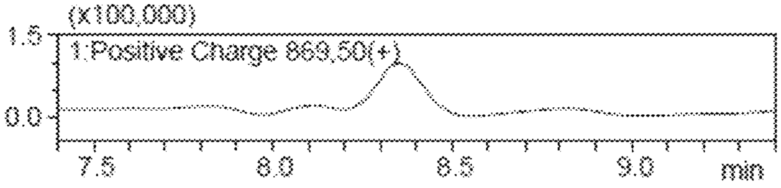
FIG. 28*d*: Exemplary embodiment No. 16: Incorporation of the modified substrate Azido-Phe (Phe=Phenylalanine) into Anabaenopeptin NZ857 produced by strain CBT 332. Extracted ion chromatogram from HPLC-MS data of mass value of protonated molecular ion of novel Anabaenopeptin variant for sample of cultivation with added modified substrate in the positive ionization mode. Detector signal intensities (y-Axis) are measured in milli-absorption units (mAU) and counts (dimensionless quantity) for PDA and mass spectrometry data respectively.
Figure 28E:
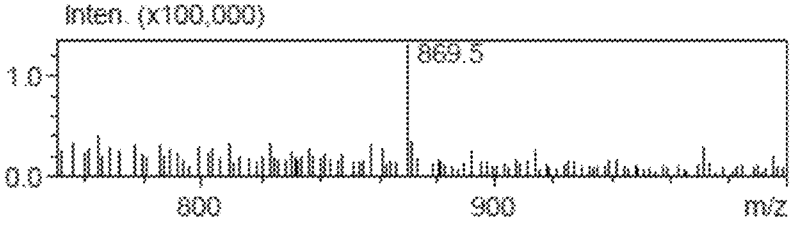
FIG. 28*e*: Exemplary embodiment No. 16: Incorporation of the modified substrate Azido-Phe (Phe=Phenylalanine) into Anabaenopeptin NZ857 produced by strain CBT 332. (e) shows the averaged mass spectrum of the peak visible in chromatogram (d).
Figure 29A:
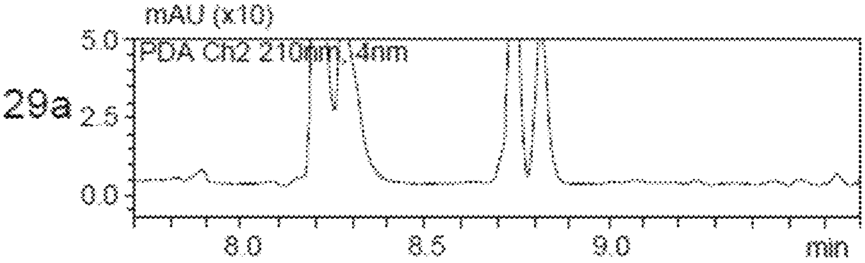
FIG. 29*a*: Exemplary embodiment No. 17: Incorporation of the modified substrate Azido-Phe (Phe=Phenylalanine) into Oscillamide Y produced by strain CBT 1161. HPLC-PDA Chromatogram at 210 nm for sample of control cultivation. Detector signal intensities (y-Axis) are measured in milli-absorption units (mAU) and counts (dimensionless quantity) for PDA and mass spectrometry data respectively.
Figure 29B:
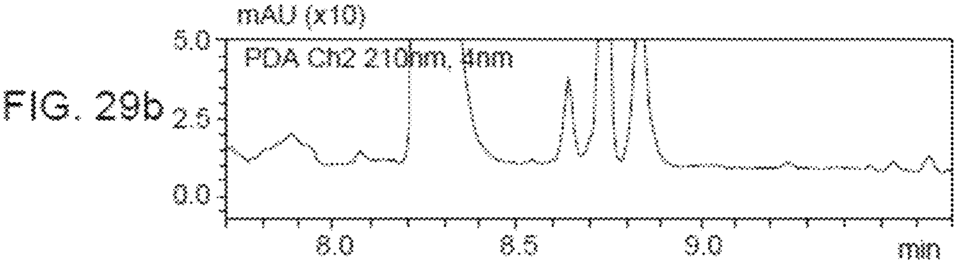
FIG. 29*b*: Exemplary embodiment No. 17: Incorporation of the modified substrate Azido-Phe (Phe=Phenylalanine) into Oscillamide Y produced by strain CBT 1161. HPLC-PDA Chromatogram at 210 nm for sample of cultivation with added modified substrate. Detector signal intensities (y-Axis) are measured in milli-absorption units (mAU) and counts (dimensionless quantity) for PDA and mass spectrometry data respectively.
Figure 29C:
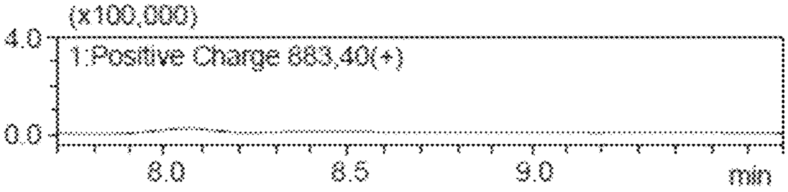
FIG. 29*c*: Exemplary embodiment No. 17: Incorporation of the modified substrate Azido-Phe (Phe=Phenylalanine) into Oscillamide Y produced by strain CBT 1161. Extracted ion chromatogram from HPLC-MS data of mass value of protonated molecular ion of novel Oscillamide variant for sample of control cultivation in the positive ionization mode. Detector signal intensities (y-Axis) are measured in milli-absorption units (mAU) and counts (dimensionless quantity) for PDA and mass spectrometry data respectively.
Figure 29D:
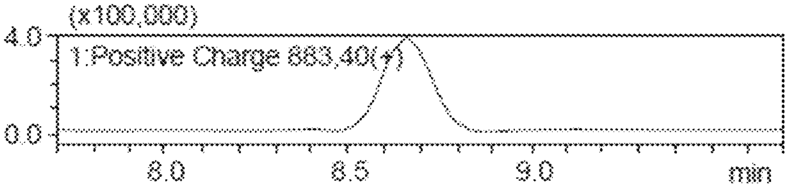
FIG. 29*d*: Exemplary embodiment No. 17: Incorporation of the modified substrate Azido-Phe (Phe=Phenylalanine) into Oscillamide Y produced by strain CBT 1161. Extracted ion chromatogram from HPLC-MS data of mass value of protonated molecular ion of novel Oscillamide variant for sample of cultivation with added modified substrate in the positive ionization mode. Detector signal intensities (y-Axis) are measured in milli-absorption units (mAU) and counts (dimensionless quantity) for PDA and mass spectrometry data respectively.
Figure 29E:
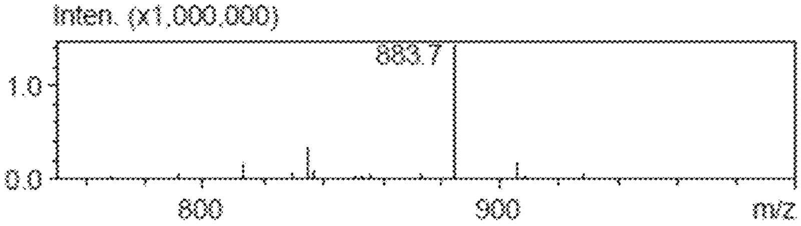
FIG. 29*e*: Exemplary embodiment No. 17: Incorporation of the modified substrate Azido-Phe (Phe=Phenylalanine) into Oscillamide Y produced by strain CBT 1161. (e) shows the averaged mass spectrum of the peak visible in chromatogram (d).
Figure 30A:
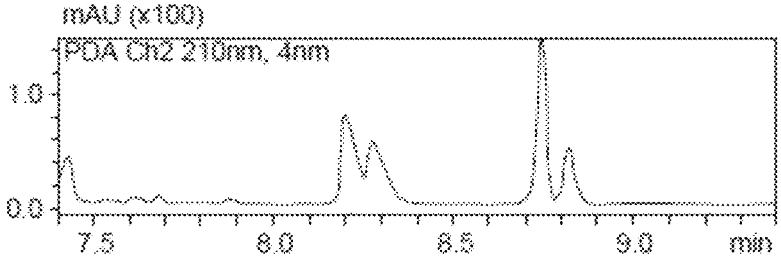
FIG. 30*a*: Exemplary embodiment No. 18: Incorporation of the modified substrate Prg-Tyr (Tyr=Tyrosine) into Oscillamide Y produced by strain CBT 1161. HPLC-PDA Chromatogram at 210 nm for sample of control cultivation. Detector signal intensities (y-Axis) are measured in milli-absorption units (mAU) and counts (dimensionless quantity) for PDA and mass spectrometry data respectively.
Figure 30B:
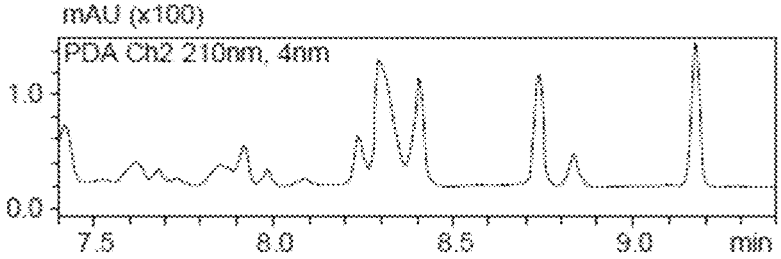
FIG. 30*b*: Exemplary embodiment No. 18: Incorporation of the modified substrate Prg-Tyr (Tyr=Tyrosine) into Oscillamide Y produced by strain CBT 1161. HPLC-PDA Chromatogram at 210 nm for sample of cultivation with added modified substrate. Detector signal intensities (y-Axis) are measured in milli-absorption units (mAU) and counts (dimensionless quantity) for PDA and mass spectrometry data respectively.
Figure 30C:
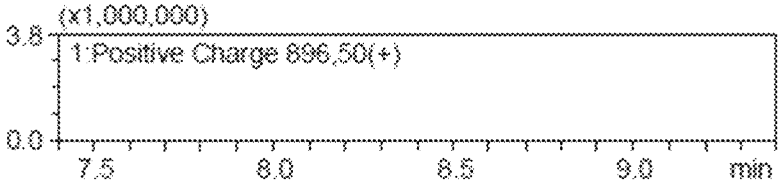
FIG. 30*c*: Exemplary embodiment No. 18: Incorporation of the modified substrate Prg-Tyr (Tyr=Tyrosine) into Oscillamide Y produced by strain CBT 1161. Extracted ion chromatogram from HPLC-MS data of mass value of protonated molecular ion of novel Oscillamide variant for sample of control cultivation in the positive ionization mode. Detector signal intensities (y-Axis) are measured in milli-absorption units (mAU) and counts (dimensionless quantity) for PDA and mass spectrometry data respectively.
Figure 30D:
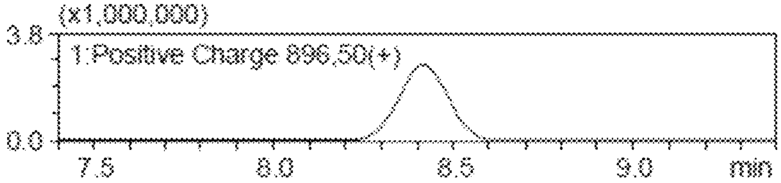
FIG. 30*d*: Exemplary embodiment No. 18: Incorporation of the modified substrate Prg-Tyr (Tyr=Tyrosine) into Oscillamide Y produced by strain CBT 1161. Extracted ion chromatogram from HPLC-MS data of mass value of protonated molecular ion of novel Oscillamide variant for sample of cultivation with added modified substrate in the positive ionization mode. Detector signal intensities (y-Axis) are measured in milli-absorption units (mAU) and counts (dimensionless quantity) for PDA and mass spectrometry data respectively.
Figure 30E:
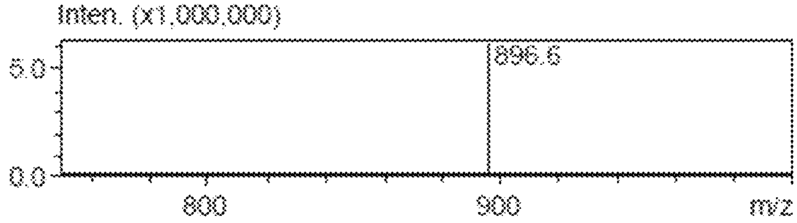
FIG. 30*e*: Exemplary embodiment No. 18: Incorporation of the modified substrate Prg-Tyr (Tyr=Tyrosine) into Oscillamide Y produced by strain CBT 1161. (e) shows the averaged mass spectrum of the peak visible in chromatogram (d).

The main difference of the here described method of introduction of conjugation chemistry incl. click chemistry into the drug-like molecules compared to conventional methods is based on the way of introduction (via feeding of pre-selected cyanobacteria strains with pre-selected substrates and their site-specific introduction into the non-ribosomal peptides), the access to a broad diversity of suited modified substrates with structural features and different kind of conjugation and click chemistry, resp., and the resulting structural diversity of clickable drug-like molecules (see FIG. 4-30). In this connection the here described method of introduction of conjugation chemistry incl. click chemistry into the drug-like molecules also differs from conventional methods by the possibility of the structurally optimization of drug-like molecules which is further enhanced by the parallel use of modified substrates w/o conjugation chemistry incl. click chemistry (see FIG. 2 A-D, 23). Finally the here described method of introduction of conjugation chemistry incl. click chemistry, into the drug-like molecules allows for the microbiological production of structurally optimized clickable non-ribosomal peptides in larger scales for industrial production (see FIGS. 24 and 25).

The cyanobacteria strain may be selected from the group comprising *Microcystis*, Planktothrix, Oscillatoria, Nostoc, Anabaena, Aphanizomenon, Hapalosiphon, Nodularia, Lyngbya, Phormidium, Spirulina, Halospirulina, Arthrospira, Trichodesmium, Leptolyngbya, Plectonema, Myxosarcina, Pleurocapsa, Pseudanabaena, Geitlerinema, Euhalothece, Calothrix, Tolypothrix, Scytonema, Fischerella, Mastigocladus, Westiellopsis, Stigonema, Chlorogloeopsis, Cyanospira, Cylindrospermopsis, Cylindospermum, Microchaete, Rivularia, Autosira, Trichonema, Trichodesmium, Symploca, Starria, Prochlorothrix, Microcoleus, Limnothrix, Crinalium, Borzia, Chroococcidiopsis, Cyanocystis, Dermocarpella, Staniera, Xenococcus, Chamaesiphon, Chroococcus, Cyanobacterium, Cyanobium, Cyanothece, Dactylococcopsis, Gloeobacter, Gloeocapsa, Gloeothece.

The inventors for the first time have incorporated modified amino acids into non-ribosomal peptides from cyanobacteria which carry so called clickable anchor groups which allow for the fast and easy binding of the entire molecule to e.g. linkers or other functional units like e.g. antibodies (see FIG. 4-10, 15/16 or whereas the fed substrates carry functional groups that are easily accessible to additional modification towards clickable anchor groups see FIGS. 11-18).

It is shown that feeding of any combination of a clickable substrate with e.g. amino acids naturally occurring in the respective non-ribosomal peptide, modified versions of these amino acids or any other modified substrates might potentially lead to an incorporation of the fed substrate combinations into the non-ribosomal peptide (see FIG. 15-18).

The inventors show for the first time that a successfully fed substrate (e.g. the modified amino acid) is structurally not necessarily directly related to the substrate that is naturally incorporated into the respective non-ribosomal peptide (e.g. the respective non-modified amino acid) (see FIG. 7/8, 13/14, 19-22, 26). That means in the past successful feedings were only regarded to structural variants directly derived from the naturally (native) incorporated amino acid (e.g. o-methyl-tyrosine or chloro-tyrosine instead of tyrosine or homo-arginine instead of arginine). Considering the new results of the inventors it is obvious that the structural and functional diversity of non-ribosomal peptides generated by feeding significantly increases if also substrates can be used that are structurally not directly derived from the substrate which is naturally incorporated into the respective non-ribosomal peptide.

The invention relates to a method of producing a modified non-ribosomal peptide, preferably a modified CA, wherein the strain and the modified substrates are selected and the chemical structure(s) of the produced non-ribosomal peptide(s) is/are known such that the incorporation of the modified substrates during cultivation into the non-ribosomal peptide occurs at a defined position.

Preferably, if the non-ribosomal peptide is a CA which is microcystin and the one or more modified substrates are incorporated at any position other than $Adda_5$ and $DGlu_6$, which has the following general structure:

$$D\text{-}Ala_1\text{-}X_2\text{-}D\text{-}MeAsp_3\text{-}Z_4\text{-}Adda_5\text{-}DGlu_6\text{-}Mdha_7,$$

and wherein X2 and Z4 are positions of preferred incorporation of said modified amino acid. If the CA is nodularin the one or more modified substrates are incorporated at any position other than $Adda_3$ and $DGlu_4$, which has the following general structure:

$$D\text{-}MeAsp_1\text{-}Arg_2\text{-}Adda_3\text{-}DGlu_4\text{-}Mdhb_5.$$

Preferably, if the non-ribosomal peptide is a CA which is microcystin, the modified position is X2 or Z4 and the modified substrate is a modified amino acid (see FIGS. 4-14).

Also, preferably if the non-ribosomal peptide is a CA which is microcystin, the modified position is X2 and Z4 and the modified substrate is a modified amino acid (see FIGS. 15-18).

The modified substrate, preferably modified amino acid, preferably contains an anchor group directly accessible or transformable for use in conjugation chemistry (incl. click chemistry), for the attachment of a targeting moiety or a label or for additional structural modifications (see FIGS. 4-30).

In the method according to the invention, the conjugation chemistry reaction (incl. click chemistry reaction) of the clickable substrate is selected from reactions comprising copper(I)-catalyzed azide-alkyne cycloaddition, strain promoted azide-alkyne cycloaddition, alkyne-azide cycloaddition, or alkyne-tetrazine inverse-demand Diels-Alder reaction. Additional conjugation chemistry can be selected from reactions exploiting the specific reactivities of primary amines, thiols, aldehydes, carboxyls, and oximes. Therefore, the anchor group of at least one modified substrate which is directly accessible for use in conjugation chemistry (incl. click chemistry), for the attachment of a targeting moiety can be selected from the group of:

- Azido groups that can subsequently be modified e.g. by reaction with alkynes, activated alkenes, or phosphines, whereas the azido group of the cytotoxin reacts with the respective functional group of a linker, antibody, or other functional molecule such as a fluorescent dye or polymer matrix.
- Alkyne (e.g. propargy or diaryl-strained cyclooctyne) groups that can subsequently be modified e.g. by reaction with azides, whereas the alkyne group of the cytotoxin reacts with the respective functional group of a linker, antibody, or other functional molecule such as a fluorescent dye or polymer matrix.
- Tetrazines that can subsequently be modified e.g. by reaction with alkynes or alkenes, whereas the tetrazine group of the cytotoxin reacts with the respective functional group of a linker, antibody, or other functional molecule such as a fluorescent dye or polymer matrix.
- Primary amines that can subsequently be modified e.g. by reaction with isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, phosphines, or fluorophenyl esters, whereas the amino group of the cytotoxin reacts with the respective functional group of a linker, antibody, or other functional molecule such as a fluorescent dye or polymer matrix.
- Thiols that can subsequently be modified e.g. by reaction with maleimides, haloacetyls, pyridyldisulfides, thiosulfonares, cyanobenzothiazoles, or vinylsulfones, whereas the thiol group of the cytotoxin reacts with the respective functional group of a linker, antibody, or other functional molecule such as a fluorescent dye or polymer matrix.
- Aldehydes that can subsequently be modified e.g. by reaction with amines, aminothiols, Ellman's Reagent, alkoxyamines, hydrazides or thiols, whereas the aldehyde group of the cytotoxin reacts with the respective functional group of a linker, antibody, or other functional molecule such as a fluorescent dye or polymer matrix.
- Carboxyls that can subsequently be modified e.g. by reaction with carbodiimides, whereas the cyrboxy group of the cytotoxin reacts with the respective functional group of a linker, antibody, or other functional molecule such as a fluorescent dye or polymer matrix.
- Oximes that can subsequently be modified e.g. by reaction with acetophenones such as p-acetylphenylalanine, whereas the oxime group of the cytotoxin reacts with the respective functional group of a linker, antibody, or other functional molecule such as a fluorescent dye or polymer matrix.

Also claimed is the introduction of at least one modified substrate with a functional group that is directly transformable for use in conjugation chemistry (incl. click chemistry) for the attachment of a targeting moiety. One examples for this is the introduction of a substrate containing a nitro group that can be reduced to yield a primary amino group, which, as described above, can be used for conjugation chemistry (incl. click chemistry). Another example is the introduction of a substrate containing a furanyl that can subsequently be modified e.g. by photoreaction with nucleophiles such as hydrazines, whereas the furanyl group reacts after activation to an unsaturated dicarbonyl residue with the respective nucleophilic functional group of a targeting moiety like a linker, antibody, or other functional molecule such as a fluorescent dye or a polymer matrix (see FIGS. 11-18).

Tyrosine containing microcystins can also be functionalized using 4-phenyl-3H-1,2,4-triazoline-3,5(4H)-diones (PTADs) to introduce additional conjugation chemistry (incl. click chemistry) amenable functional groups as described above.

Ideally, modified amino acids which are directly accessible or transformable for use in conjugation chemistry (incl. click chemistry), are selected from the group of the following table (see FIGS. 4-30 and tables 1 to 4 for respective execution examples):

| Systematic name | CAS Number | Short name | Supplier | Order number |
|---|---|---|---|---|
| (2S)-2-amino-3-azidopropanoic acid hydrochloride | 105661-40-3 | Azido-L-Ala | Iris Biotech GmbH | HAA1880 |
| (2S)-2-amino-6-azidohexanoic acid hydrochloride | 159610-92-1 | Azido-Lys | Iris Biotech GmbH | HAA1625 |
| (S)-2-Amino-5-azidopentanoic acid hydrochloride | 156463-09-1 | Azido-Norval | Iris Biotech GmbH | HAA1620 |
| (2S)-2-amino-3-(4-prop-2-ynoxyphenyl)propanoic acid hydrochloride | 610794-20-2 | Prg-Tyr | Iris Biotech GmbH | HAA1971 |
| (2S)-2-amino-5-(N'-nitrocarbamimidamido)pentanoic acid | 2149-70-4 | Nitro-Arg | Sigma-Aldrich Chemie GmbH | 2149-70-4 |
| (2S)-2-amino-3-(furan-2-yl)propanoic acid | 127682-08-0 | Furyl-Ala | Iris Biotech GmbH | HAA2930 |
| (S)-Amino-6-((prop-2-ynyloxy)carbonylamino)hexanoic acid hydrochloride | 1428330-91-9 | Lys(Poc) | Iris Biotech GmbH | HAA2090 |
| N-Propargyl-Lysine | 1428330-91-9 | Prg-Lys | SiChem | SC-8002 |
| (2S)-2-Amino-3-(4-azidophenyl)propanoic acid | 33173-53-4 | Azido-L-Phe | Iris Biotech GmbH | HAA1850 |
| L-α-Amino-ε-guanidinohexanoic acid | 156-86-5 | H-homo-Arg-OH | Bachem | 4016423 |

The invention relates to a method, wherein one of the following microcystins is produced, $$D\text{-}Ala_1\text{-}X_2\text{-}D\text{-}MeAsp_3\text{-}Z_4\text{-}Adda_5\text{-}DGlu_6\text{-}Mdha_7,$$

| Position | 1 | 2 | 3 | 4 | 5 | 6 | 7 |
|---|---|---|---|---|---|---|---|
| Possible amino acids | $Ala_1$ | $X_2$ | D-$MeAsp_3$ | $Z_4$ | $Adda_5$ | $DGlu_6$ | $Mdha_7$ |
| | D-Ala<br>D-Ser<br>D-Leu | variable | D-MeAsp<br>D-Asp | variable | Adda<br>DM-Adda<br>(6Z)Adda<br>ADM-Adda | D-Glu<br>D-Glu($OCH_3$) | Mdha<br>Dha<br>L-Ser<br>L-MeSer<br>Dhb<br>MeLan |

wherein

| $Ala_1$ | $X_2$ | D-$MeAsp_3$ | $Z_4$ | $Mdha_7$ |
|---|---|---|---|---|

comprise the position of the incorporation of at least one modified substrate wherein preferably the modified substrate which are directly accessible or transformable for use in conjugation (click) chemistry is an amino acid selected from the group of:

| Systematic name | CAS Number | Short name | Supplier | Order number |
|---|---|---|---|---|
| (2S)-2-amino-3-azidopropanoic acid hydrochloride | 105661-40-3 | Azido-L-Ala | Iris Biotech GmbH | HAA1880 |

-continued

| Systematic name | CAS Number | Short name | Supplier | Order number |
|---|---|---|---|---|
| (2S)-2-amino-6-azidohexanoic acid hydrochloride | 159610-92-1 | Azido-Lys | Iris Biotech GmbH | HAA1625 |
| (S)-2-Amino-5-azidopentanoic acid hydrochloride | 156463-09-1 | Azido-Norval | Iris Biotech GmbH | HAA1620 |
| (2S)-2-amino-3-(4-prop-2-ynoxyphenyl)propanoic acid hydrochloride | 610794-20-2 | Prg-Tyr | Iris Biotech GmbH | HAA1971 |
| (2S)-2-amino-5-(N'-nitrocarbamimidamido)pentanoic acid | 2149-70-4 | Nitro-Arg | Sigma-Aldrich Chemie GmbH | 2149-70-4 |
| (2S)-2-amino-3-(furan-2-yl)propanoic acid | 127682-08-0 | Furyl-Ala | Iris Biotech GmbH | HAA2930 |
| (S)-Amino-6-((prop-2-ynyloxy)carbonylamino)hexanoic acid hydrochloride | 1428330-91-9 | Lys(Poc) | Iris Biotech GmbH | HAA2090 |
| N-Propargyl-Lysine | 1428330-91-9 | Prg-Lys | SiChem | SC-8002 |
| (2S)-2-Amino-3-(4-azidophenyl)propanoic acid | 33173-53-4 | Azido-L-Phe | Iris Biotech GmbH | HAA1850 |
| L-α-Amino-ε-guanidinohexanoic acid | 156-86-5 | H-homo-Arg-OH | Bachem | 4016423 |

(e.g., SEQ ID NO: 1, SEQ ID NO: 6).

The invention also relates to a method, wherein one of the following nodularins is produced,

| | Position | | | | |
|---|---|---|---|---|---|
| | 1 | 2 | 3 | 4 | 5 |
| Possible amino acid | $MeAsp_1$ | $Arg_2$ | $Adda_3$ | $DGlu_4$ | $Mdhb_5$ |
| | D-MeAsp | Homo-Arg | Adda | D-Glu | Mdhb |

-continued

| Position | | | | |
|---|---|---|---|---|
| 1 | 2 | 3 | 4 | 5 |
| D-Asp | | DM-Adda<br>(6Z)Adda<br>Me-Adda | D-Glu($OCH_3$) | Dhb |

wherein

| $MeAsp_1$ | $Arg_2$ | $Mdhb_5$ |
|---|---|---|

comprise the position for the at least one modified substrate, wherein preferably the modified substrate is an amino acid selected from the group of:

| Systematic name | CAS Number | Short name | Supplier | Order number |
|---|---|---|---|---|
| (2S)-2-amino-3-azidopropanoic acid hydrochloride | 105661-40-3 | Azido-L-Ala | Iris Biotech GmbH | HAA1880 |
| (2S)-2-amino-6-azidohexanoic acid hydrochloride | 159610-92-1 | Azido-Lys | Iris Biotech GmbH | HAA1625 |
| (S)-2-Amino-5-azidopentanoic acid hydrochloride | 156463-09-1 | Azido-Norval | Iris Biotech GmbH | HAA1620 |
| (2S)-2-amino-3-(4-prop-2-ynoxyphenyl)propanoic acid hydrochloride | 610794-20-2 | Prg-Tyr | Iris Biotech GmbH | HAA1971 |
| (2S)-2-amino-5-(N'-nitrocarbamimidamido)pentanoic acid | 2149-70-4 | Nitro-Arg | Sigma-Aldrich Chemie 3mbH | 2149-70-4 |
| (2S)-2-amino-3-(furan-2-yl)propanoic acid | 127682-08-0 | Furyl-Ala | Iris Biotech GmbH | HAA2930 |
| (S)-Amino-6-((prop-2-ynyloxy)carbonylamino)hexanoic acid hydrochloride | 1428330-91-9 | Lys(Poc) | Iris Biotech GmbH | HAA2090 |

-continued

| Systematic name | CAS Number | Short name | Supplier | Order number |
|---|---|---|---|---|
| N-Propargyl-Lysine | 1428330-91-9 | Prg-Lys | SiChem | SC-8002 |
| (2S)-2-Amino-3-(4-azidophenyl)propanoic acid | 33173-53-4 | Azido-L-Phe | Iris Biotech GmbH | HAA1850 |
| L-α-Amino-ε-guanidinohexanoic acid | 156-86-5 | H-homo-Arg-OH | Bachem | 4016423 |

(e.g., SEQ ID NO: 2). Ideally, the nodularin is modified at the $Arg_2$ position.

The invention also relates to a method, wherein one of the following anabaenopeptins is produced,

| | Position | | | | |
|---|---|---|---|---|---|
| | 1 | 3 | 4 | 5 | 6 |
| Possible amino acid | Tyr | Val | HTyr | MeAla | Phe |
| | Arg | Ile | MeHTyr | MeLeu | Tyr |
| | Lys | | HPhe | MeHTyr | Ile |
| | Phe | | | MeTyr | Leu |
| | Ile | | | | |
| | HArg | | | | |

wherein

| | |
|---|---|
| Tyr | Phe |

comprise the position for the at least one modified substrate, wherein preferably the modified substrate is an amino acid selected from the group of:

| Systematic name | CAS Number | Short name | Supplier | Order number |
|---|---|---|---|---|
| (2S)-2-amino-3-azidopropanoic acid hydrochloride | 105661-40-3 | Azido-L-Ala | Iris Biotech GmbH | HAA1880 |
| (2S)-2-amino-6-azidohexanoic acid hydrochloride | 159610-92-1 | Azido-Lys | Iris Biotech GmbH | HAA1625 |
| (S)-2-Amino-5-azidopentanoic acid hydrochloride | 156463-09-1 | Azido-Norval | Iris Biotech GmbH | HAA1620 |
| (2S)-2-amino-3-(4-prop-2-ynoxyphenyl)propanoic acid hydrochloride | 610794-20-2 | Prg-Tyr | Iris Biotech GmbH | HAA1971 |
| (2S)-2-amino-5-(N'-nitrocarbamimidamido)pentanoic acid | 2149-70-4 | Nitro-Arg | Sigma-Aldrich Chemie GmbH | 2149-70-4 |
| (2S)-2-amino-3-(furan-2-yl)propanoic acid | 127682-08-0 | Furyl-Ala | Iris Biotech GmbH | HAA2930 |
| (S)-Amino-6-((prop-2-ynyloxy)carbonylamino)hexanoic acid hydrochloride | 1428330-91-9 | Lys(Poc) | Iris Biotech GmbH | HAA2090 |
| N-Propargyl-Lysine | 1428330-91-9 | Prg-Lys | SiChem | SC-8002 |
| (2S)-2-Amino-3-(4-azidophenyl)propanoic acid | 33173-53-4 | Azido-L-Phe | Iris Biotech GmbH | HAA1850 |
| L-α-Amino-ε-guanidinohexanoic acid | 156-86-5 | H-homo-Arg-OH | Bachem | 4016423 |

(e.g., SEQ ID NO: 3, SEQ ID NO: 7, SEQ ID NO: 8).

The invention also relates to a method, wherein one of the following oscillamides is produced,

| | Position | | | | |
|---|---|---|---|---|---|
| | 1 | 3 | 4 | 5 | 6 |
| Possible amino acid | Tyr | Met | HTyr | MeAla | Phe |
| | Arg | Ile | | MeHTyr | |

wherein

| | |
|---|---|
| Tyr | HTyr |

comprise the position for the at least one modified substrate, wherein preferably the modified substrate is an amino acid selected from the group of:

| Systematic name | CAS Number | Short name | Supplier | Order number |
|---|---|---|---|---|
| (2S)-2-amino-3-azidopropanoic acid hydrochloride | 105661-40-3 | Azido-L-Ala | Iris Biotech GmbH | HAA1880 |
| (2S)-2-amino-6-azidohexanoic acid hydrochloride | 159610-92-1 | Azido-Lys | Iris Biotech GmbH | HAA1625 |
| (S)-2-Amino-5-azidopentanoic acid hydrochloride | 156463-09-1 | Azido-Norval | Iris Biotech GmbH | HAA1620 |
| (2S)-2-amino-3-(4-prop-2-ynoxyphenyl)propanoic acid hydrochloride | 610794-20-2 | Prg-Tyr | Iris Biotech GmbH | HAA1971 |
| (2S)-2-amino-5-(N'-nitrocarbamimidamido)pentanoic acid | 2149-70-4 | Nitro-Arg | Sigma-Aldrich Chemie GmbH | 2149-70-4 |
| (2S)-2-amino-3-(furan-2-yl)propanoic acid | 127682-08-0 | Furyl-Ala | Iris Biotech GmbH | HAA2930 |
| (S)-Amino-6-((prop-2-ynyloxy)carbonylamino)hexanoic acid hydrochloride | 1428330-91-9 | Lys(Poc) | Iris Biotech GmbH | HAA2090 |
| N-Propargyl-Lysine | 1428330-91-9 | Prg-Lys | SiChem | SC-8002 |
| (2S)-2-Amino-3-(4-azidophenyl)propanoic acid | 33173-53-4 | Azido-L-Phe | Iris Biotech GmbH | HAA1850 |
| L-α-Amino-ε-guanidinohexanoic acid | 156-86-5 | H-homo-Arg-OH | Bachem | 4016423 |

(e.g., SEQ ID NO: 4, SEQ ID NO: 9, SEQ ID NO: 10).

The invention also relates to a method, wherein modified cryptophycins are produced, wherein the O-methyl-chloro-Tyrosine in cryptophycin 1 comprise the position for the at least one modified substrate, wherein preferably the modified substrate is an amino acid selected from the group of:

| Systematic name | CAS Number | Short name | Supplier | Order number |
|---|---|---|---|---|
| (2S)-2-amino-3-azidopropanoic acid hydrochloride | 105661-40-3 | Azido-L-Ala | Iris Biotech GmbH | HAA1880 |
| (2S)-2-amino-6-azidohexanoic acid hydrochloride | 159610-92-1 | Azido-Lys | Iris Biotech GmbH | HAA1625 |
| (S)-2-Amino-5-azidopentanoic acid hydrochloride | 156463-09-1 | Azido-Norval | Iris Biotech GmbH | HAA1620 |
| (2S)-2-amino-3-(4-prop-2-ynoxyphenyl)propanoic acid hydrochloride | 610794-20-2 | Prg-Tyr | Iris Biotech GmbH | HAA1971 |
| (2S)-2-amino-5-(N'-nitrocarbamimidamido)pentanoic acid | 2149-70-4 | Nitro-Arg | Sigma-Aldrich Chemie GmbH | 2149-70-4 |
| (2S)-2-amino-3-(furan-2-yl)propanoic acid | 127682-08-0 | Furyl-Ala | Iris Biotech GmbH | HAA2930 |
| (S)-Amino-6-((prop-2-ynyloxy)carbonylamino)hexanoic acid hydrochloride | 1428330-91-9 | Lys(Poc) | Iris Biotech GmbH | HAA2090 |
| N-Propargyl-Lysine | 1428330-91-9 | Prg-Lys | SiChem | SC-8002 |
| (2S)-2-Amino-3-(4-azidophenyl)propanoic acid | 33173-53-4 | Azido-L-Phe | Iris Biotech GmbH | HAA1850 |
| L-α-Amino-ε-guanidinohexanoic acid | 156-86-5 | H-homo-Arg-OH | Bachem | 4016423 |

(e.g., SEQ ID NO: 5).

In the method according to the invention, the at least one modified amino acid comprises an anchor group directly accessible or transformable for use in conjugation chemistry (incl. click chemistry), for the attachment of a targeting moiety and/or a label via a linker or w/o a linker between the modified amino acid and the targeting moiety and/or a label. Such anchor groups are described above for the modified substrates.

In the method according to the invention, the conjugation chemistry reaction (incl. click chemistry reaction) of the clickable substrate is selected from the group comprising copper(I)-catalyzed azide-alkyne cycloaddition, strain-promoted azide-alkyne cycloaddition, alkyne-azide cycloaddition, or alkyne-tetrazine inverse-demand Diels-Alder reaction. Additional conjugation chemistry can be selected from reactions exploiting the specific reactivities of primary amines, thiols, aldehydes, carboxyls, and oximes.

However, regarding the modification of the CA of microcystins and nodularins by the introduction of modified substrates most preferred are the genera *Microcystis, Planktothrix, Oscillatoria, Nostoc, Anabaena, Aphanizomenon, Hapalosiphon, Nodularia.*

The invention relates to a modified non-ribosomal peptide, including a modified CA compound comprising at least one modified amino acid, wherein the at least one modified amino acid comprises an anchor group directly accessible or transformable for use in conjugation chemistry (incl. click chemistry), for the attachment of a targeting moiety and/or a label via a linker or w/o a linker between the modified amino acid and the targeting moiety and/or a label.

Ideally, the at least one modified CA compound is a microcystin, a nodularin or a cryptophycin or one of the CA listed in the above table with cyanobacterial CA.

Preferably, the modified amino acid in the CA is linked to a targeting moiety or a label.

Concerning the targeting moiety (TM), in one embodiment, the ADC specifically binds to a receptor encoded by an ErbB gene. The TM may bind specifically to an ErbB receptor selected from EGFR, HER2, HER3 and HER4. The ADC may specifically bind to the extracellular domain (ECD) of the HER2 receptor and inhibit the growth of tumor cells which overexpress HER2 receptor (see FIG. 34). The antibody of the ADC may be a monoclonal antibody, e.g. a murine monoclonal antibody, a chimeric antibody, or a humanized antibody. A humanized antibody may be huMAb4D5-1, huMAb4D5-2, huMAb4D5-3, huMAb4D5-4, huMAb4D5-5, huMAb4D5-6, huMAb4D5-7 or huMAb4D5-8 (trastuzumab). The antibody may be an antibody fragment, e.g. a Fab fragment.

The ADC of the invention may be useful in the treatment of cancer including, but are not limited to, antibodies against cell surface receptors and tumor-associated antigens (TAA). Such tumor-associated antigens are known in the art, and can prepared for use in generating antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via targeted antibody-based therapies.

Examples of TAA include, but are not limited to, Tumor-Associated Antigens listed below. Tumor-associated antigens targeted by antibodies include all amino acid sequence variants and isoforms possessing at least about 70%, 80%, 85%, 90%, or 95% sequence identity relative to the sequences identified in the cited references, or which exhibit substantially the same biological properties or characteristics as a TAA having a sequence found in the cited references. For example, a TAA having a variant sequence generally is able to bind specifically to an antibody that binds specifically to the TAA with the corresponding sequence listed. The sequences and disclosure in the reference specifically recited herein are expressly incorporated by reference.

Figure 1A:
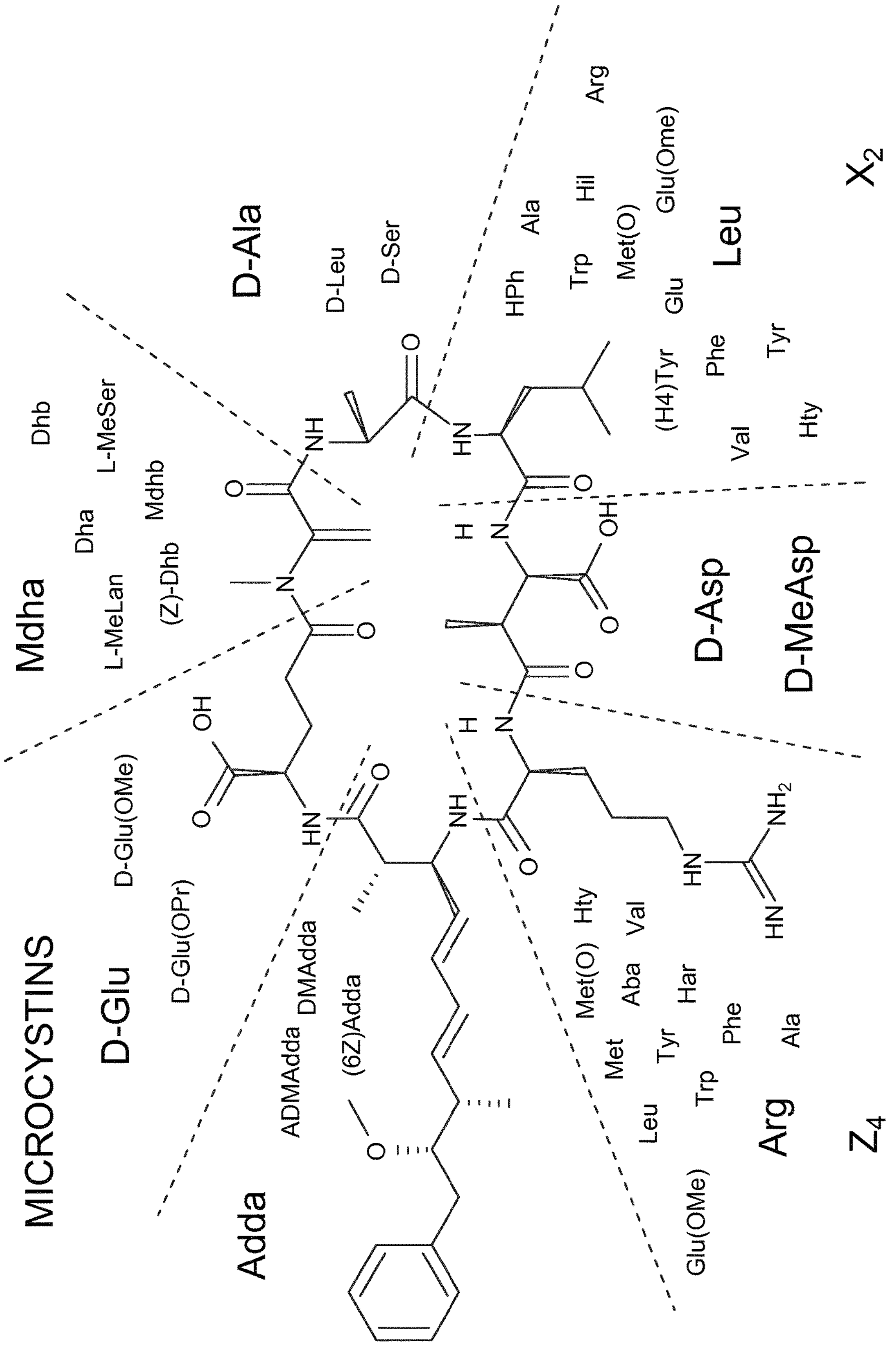
FIG. 1A: General structure of Microcystins. X2 and Z4 indicate variable L-amino acids. D-Ala=D-Alanine, D-Me-Asp=D-methyl aspartic acid, Arg=Arginine, Adda=3-amino-9-methoxy-2,6,8-trimethyl-10-phenyldeca-4,6-dienoic acid, D-Glu=D-glutamic acid, Mdha=N-methyldehydroalanine.
Figure 1B:
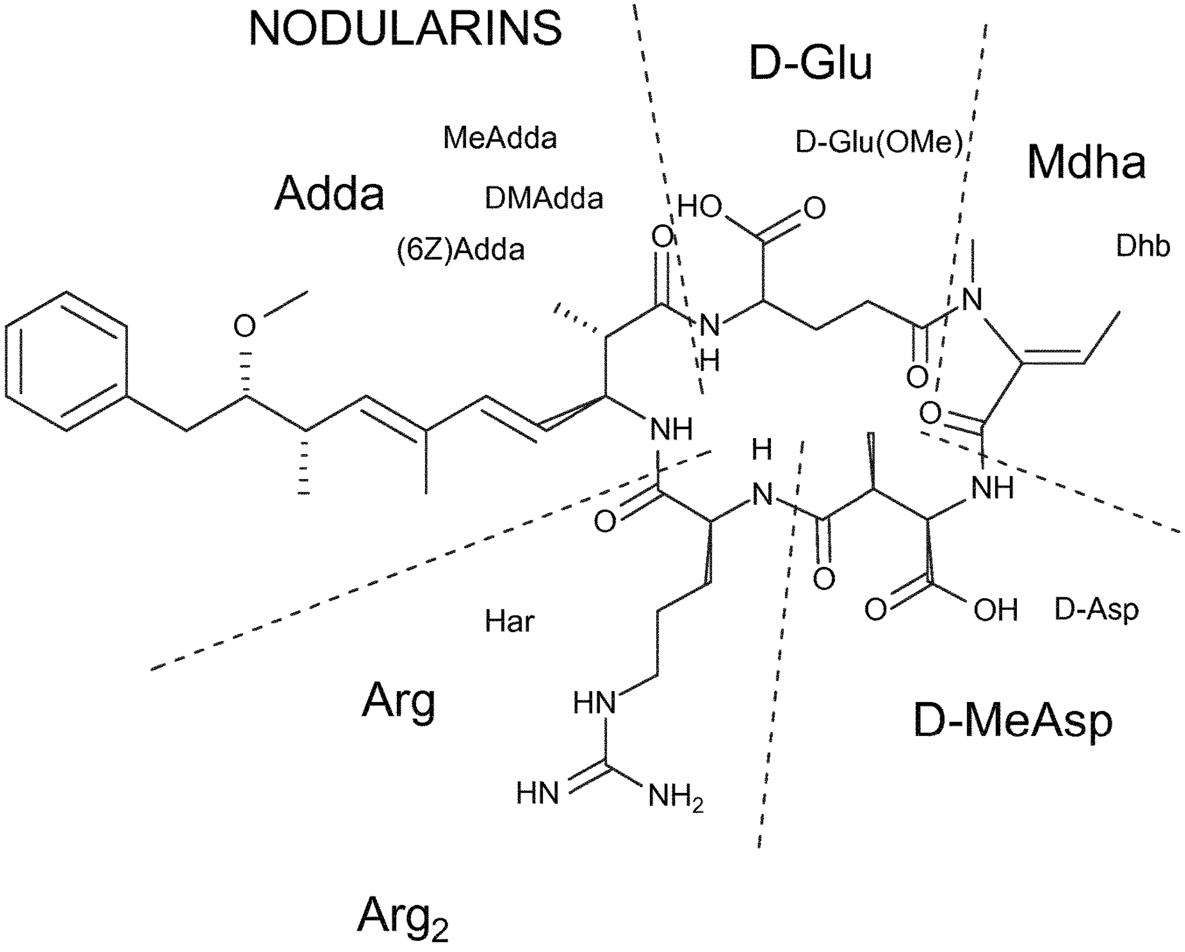
FIG. 1B: General structure of Nodularins. $Arg_2$ indicates the variable L-amino acid corresponding to Z4 in the microcystin molecule. D-Me-Asp=D-methyl aspartic acid, Arg=Arginine, Adda=3-amino-9-methoxy-2,6,8-trimethyl-10-phenyldeca-4,6-dienoic acid, D-Glu=D-glutamic acid, Mdhb=N-methyldehydrobutyrate.
Figure 1C:
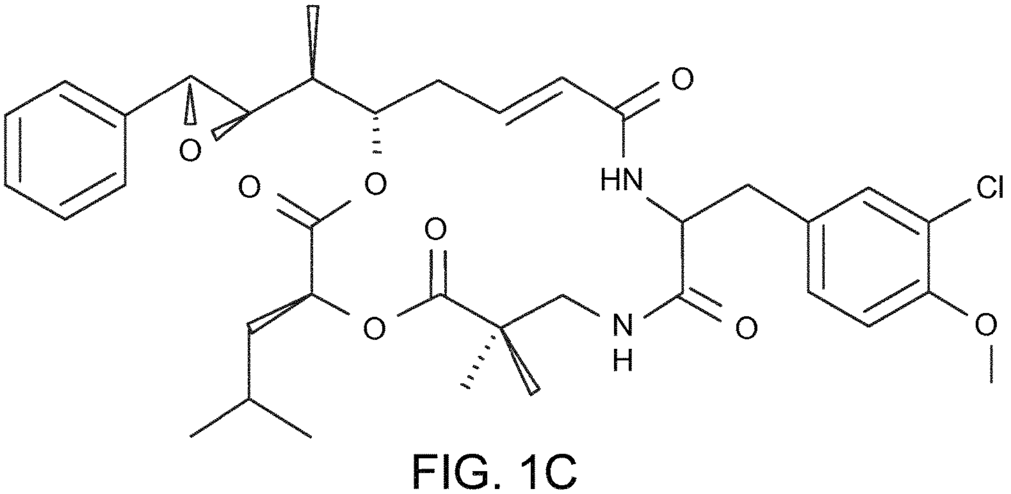
FIG. 1C: General structure of anabaenopeptin A and schematic general structure of anabaenopeptin type peptides (incl. oscillamides): Anabaenopeptins (and oscillamides) are cyclic peptides that are characterized by a lysine in position 5 and the formation of the ring by an N-6-peptide bond between Lys and the carboxy group of the amino acid in position 6 A side chain of one amino acid unit is attached to the ring by an ureido bond formed between the a-N of Lys and the a-N of the side chain amino acid. All other positions in the ring and side chain are variable.
Figure 2A:
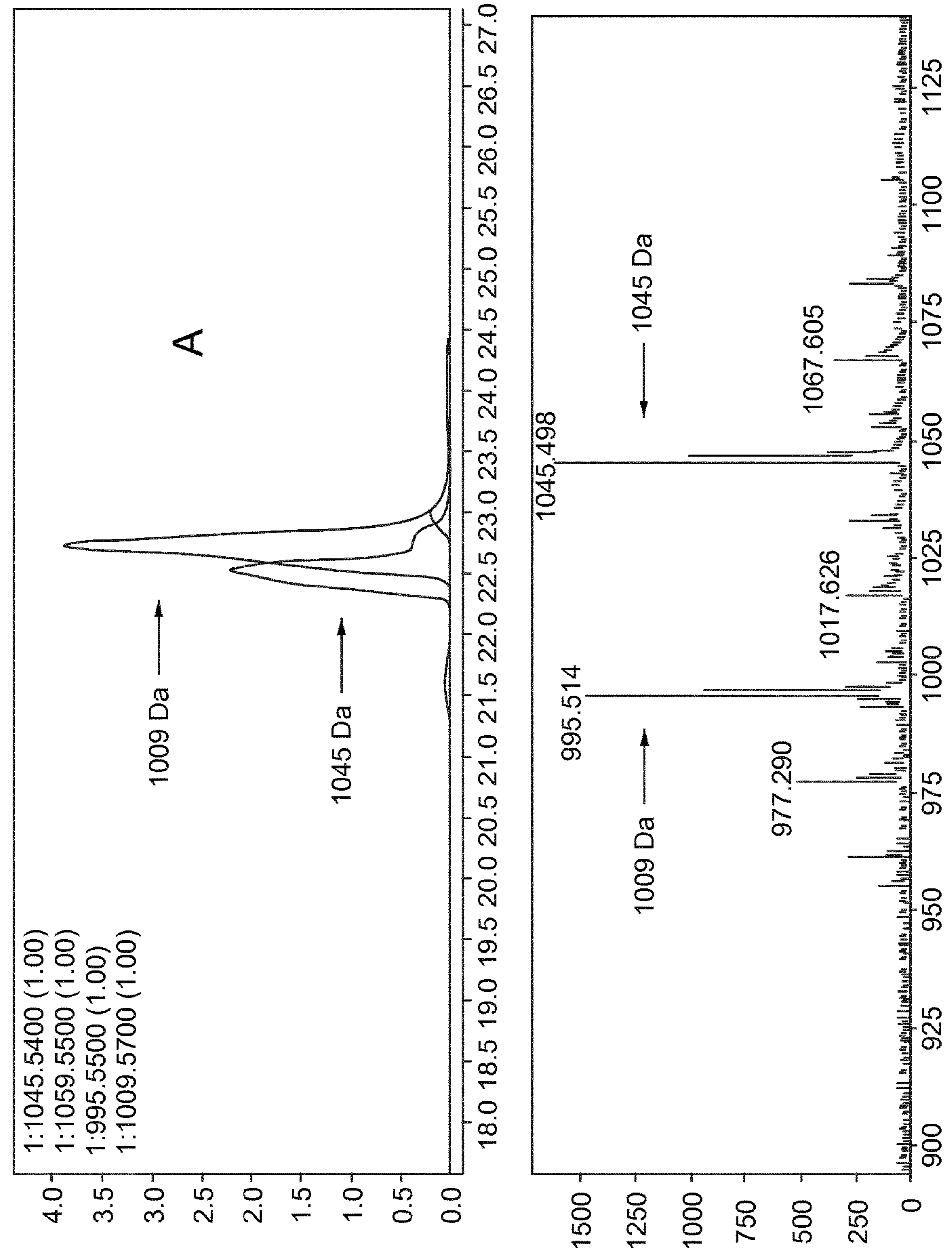
FIG. 2A: Detection of modified microcystins by two different mass spectrometry methods after feeding of modified substrates to a *Microcystis aeruginosa* strain CBT 480 in a 50 ml scale (above of each of the four figures A, B, C, D detection with ESI-IT-ToF-MS; below of each of the four figures A, B, C, D detection with MALDI-ToF-MS). A: Control (no feeding with O-methyltyrosine); B: Control (no feeding with homoarginine); C: Feeding with O-methyltyrosine; D: Feeding with homoarginine; Molecule masses of naturally produced microcystins: 995 Da=MC-LR, 1045 Da=MC-YR; Molecule masses of modified microcystins generated by feeding with O-methyltyrosine (OMetY) and homoarginine (hR): 1059 Da=MC-OMetYR or MC-YhR; 1009 Da=MC-LhR.
Figure 2A:
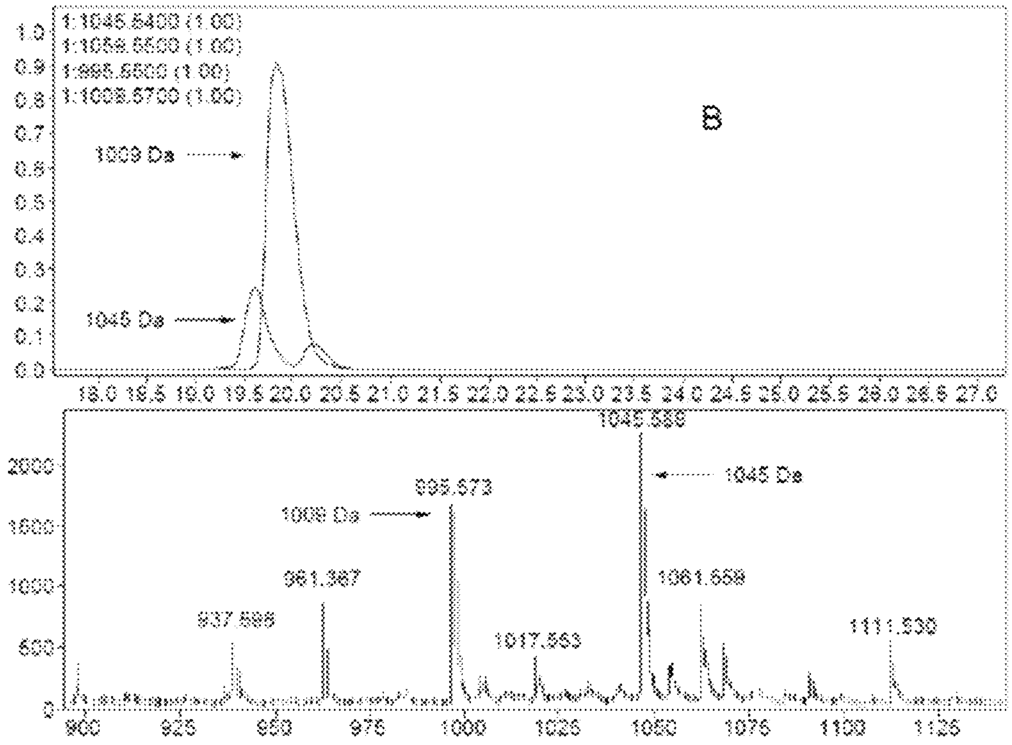
Figure 2A:
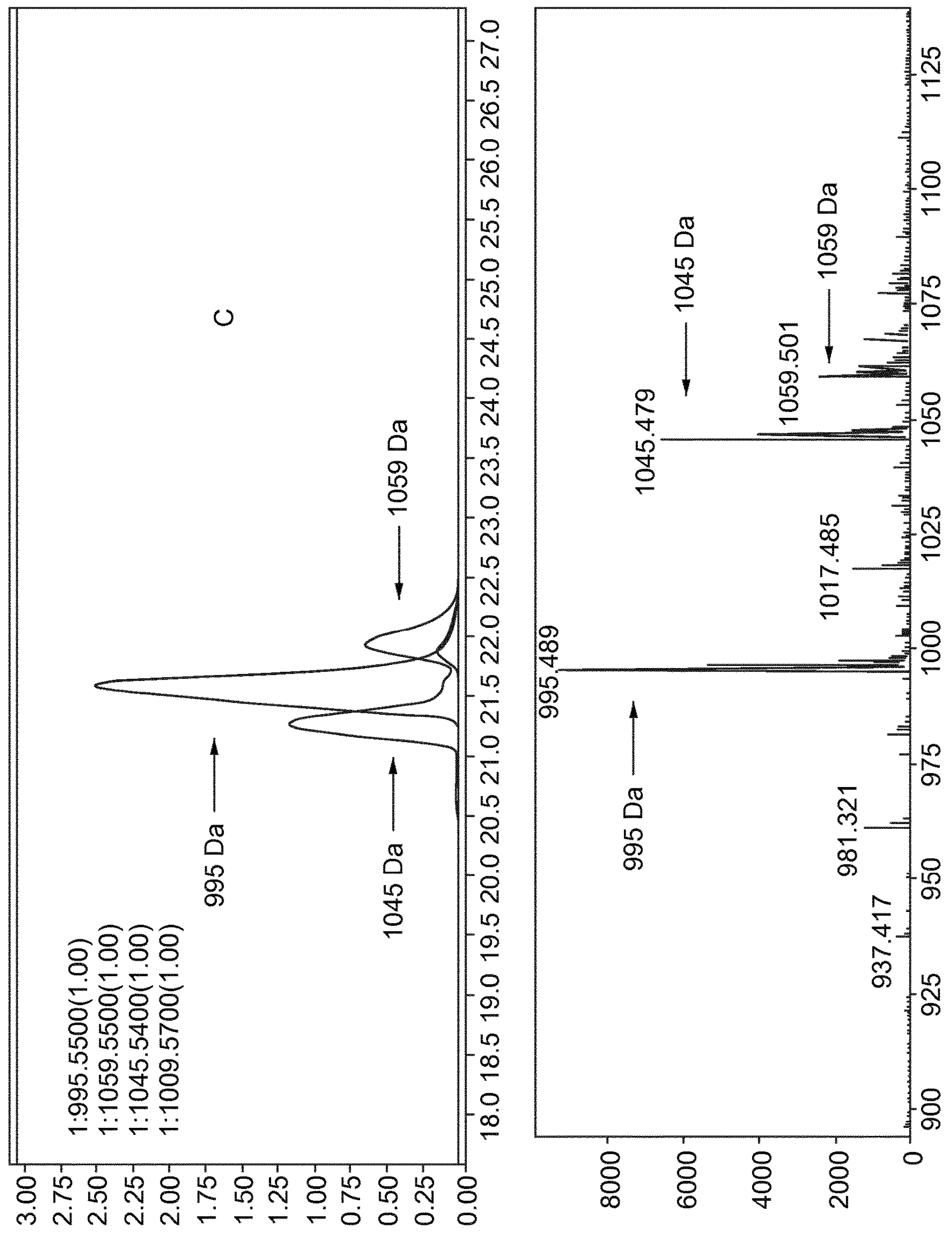
Figure 2A:
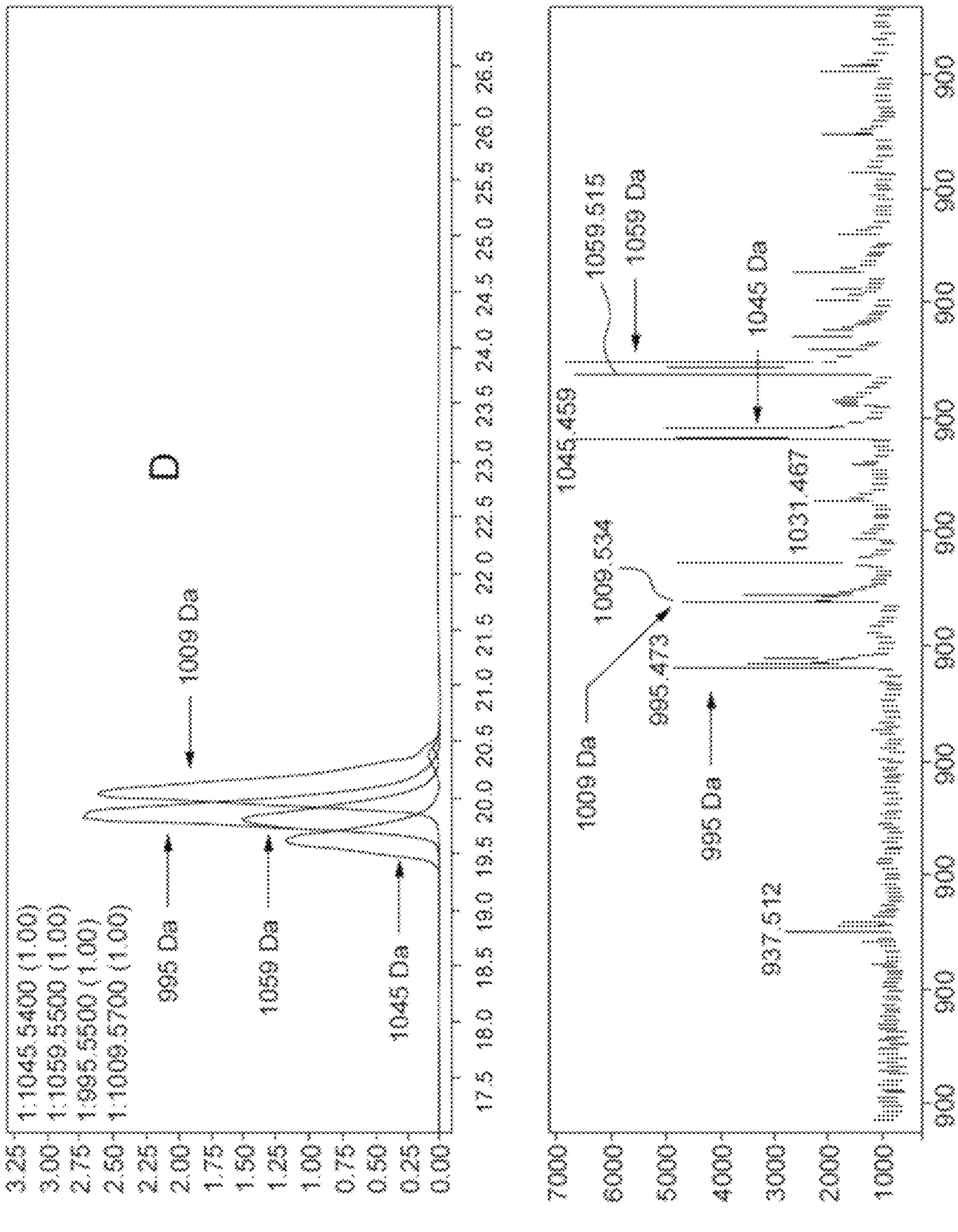
Figure 2B:
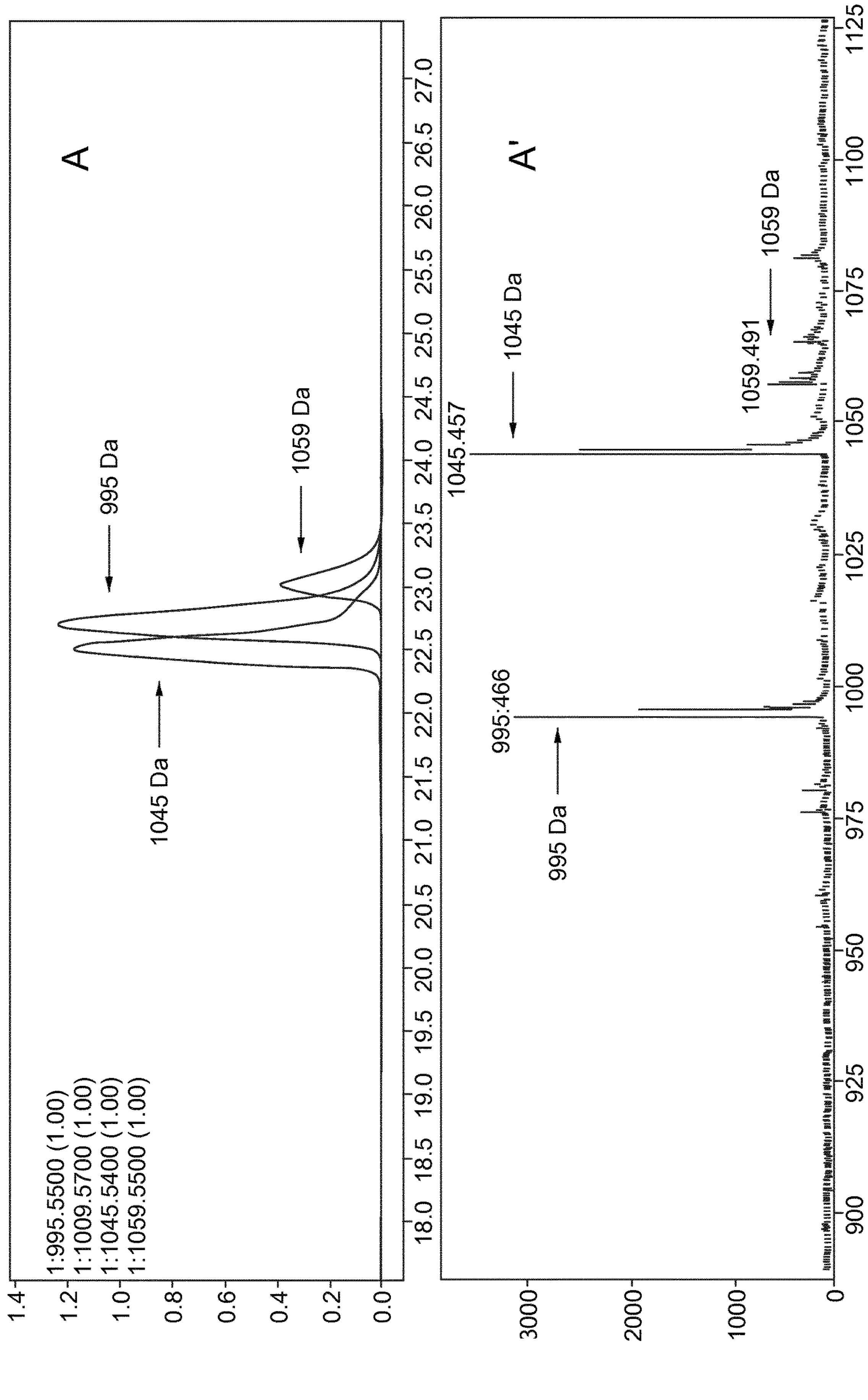
FIG. 2B: Detection of modified microcystins by two different mass spectrometry methods after feeding of modified substrates to a *Microcystis aeruginosa* strain CBT 480 in a 6 ml scale (above of each of the two figures A/A' and B/B' detection with ESI-IT-ToF-MS; below of each of the two figures A/A' and B/B' detection with MALDI-ToF-MS). A, A': CBT 480 culture fed with O-methyltyrosine; B, B': CBT 480 culture fed with homoarginine; Molecule masses of naturally produced microcystins: 995 Da=MC-LR, 1045 Da=MC-YR; Molecule masses of modified microcystins generated by feeding with O-methyltyrosine (OMetY) and homoarginine (hR): 1059 Da=MC-OMetYR or MC-YhR; 1009 Da=MC-Lh R.
Figure 2B:
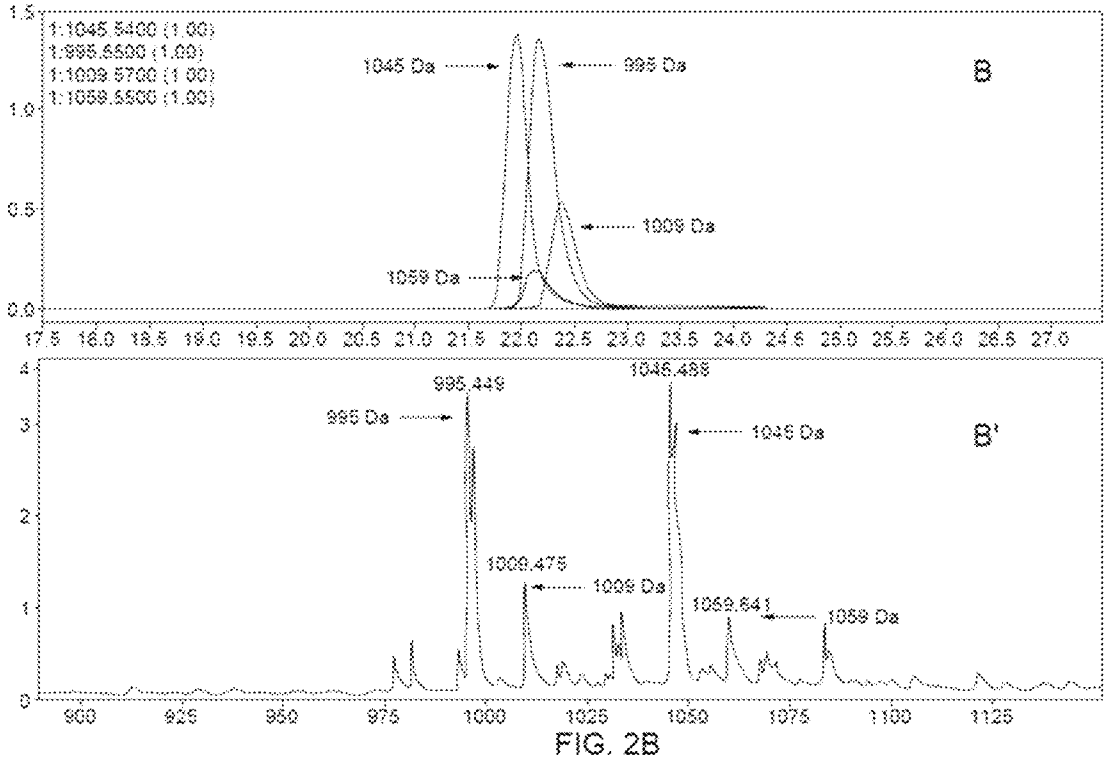
Figure 2C:
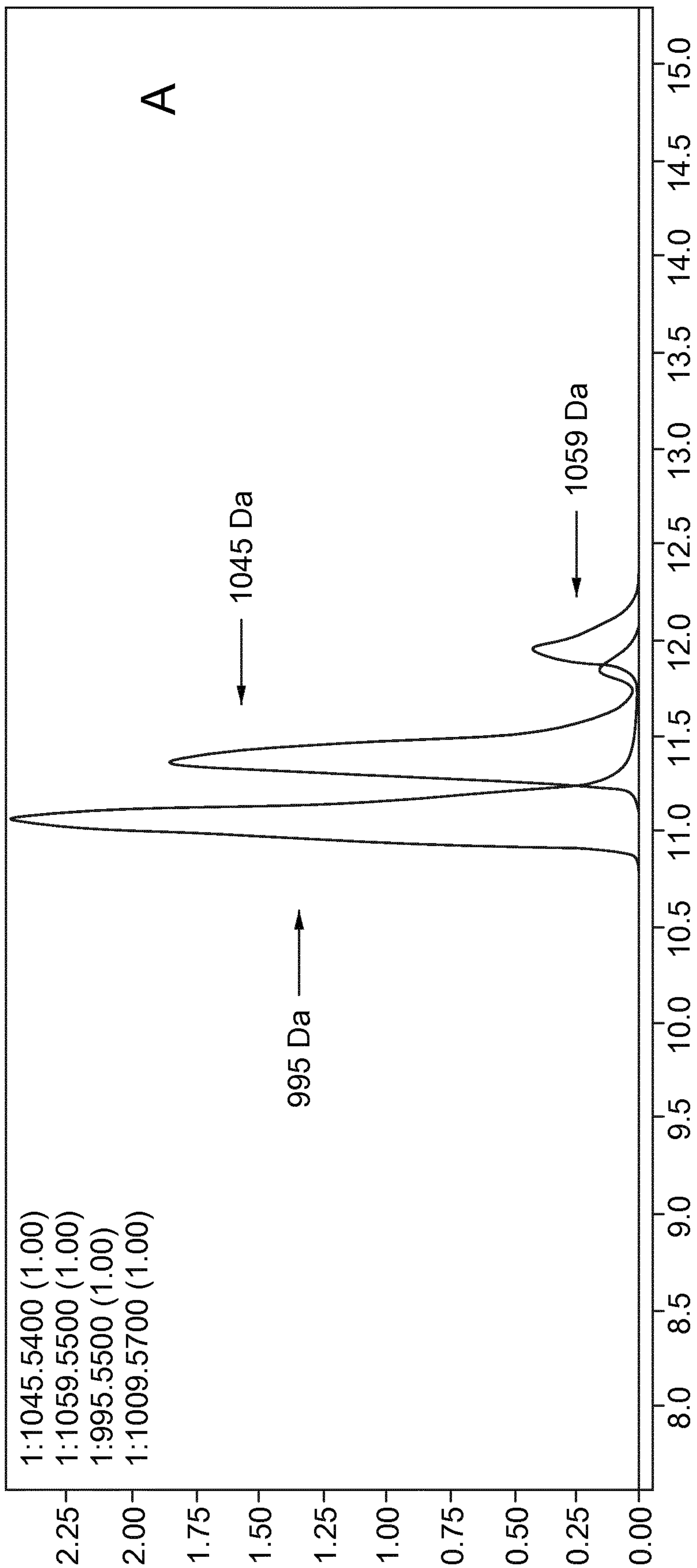
FIG. 2C: Detection of modified microcystins by two different mass spectrometry methods after feeding of modified substrates to a *Microcystis aeruginosa* strain CBT 480 with O-methyltyrosine in a 1.6 ml (dw-MTP) scale (ESI-IT-ToF-MS on the left; MALDI-ToF-MS on the right) A, A': feeding of 300 μM O-methyltyrosine (OMetY), w/o DMSO; B, B': feeding of 30 μM O-methyltyrosine (0-MetY), w/o DMSO; C, C': feeding of 300 μM O-methyltyrosine (OMetY), w/1% DMSO; D, D': feeding of 30 μM O-methyltyrosine (OMetY), w/1% DMSO; E, E': control (no feeding); Molecule masses of naturally produced microcystins: 995 Da=MC-LR, 1045 Da=MC-YR; Molecule masses of modified microcystin generated by feeding with O-methyltyrosine: 1059 Da=MC-OmetYR.
Figure 2C:
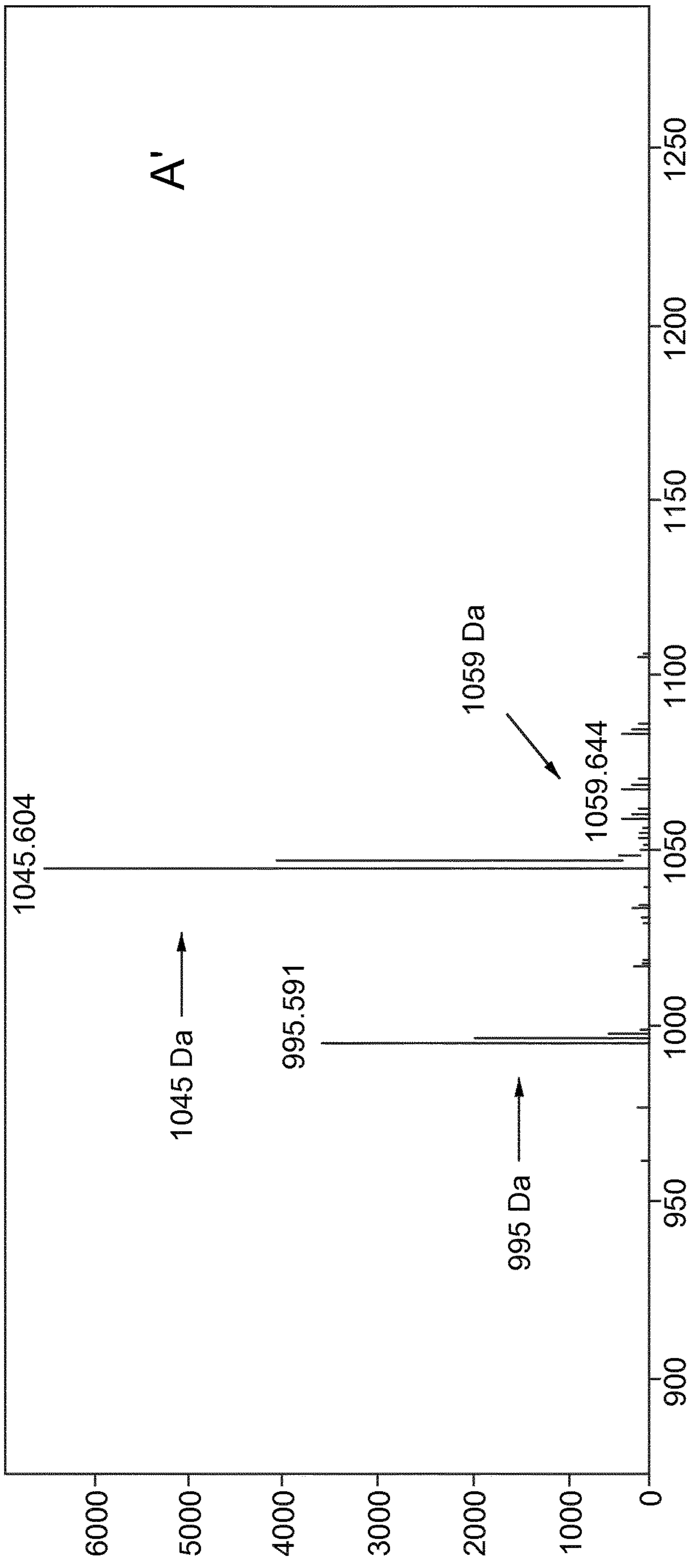
Figure 2C:
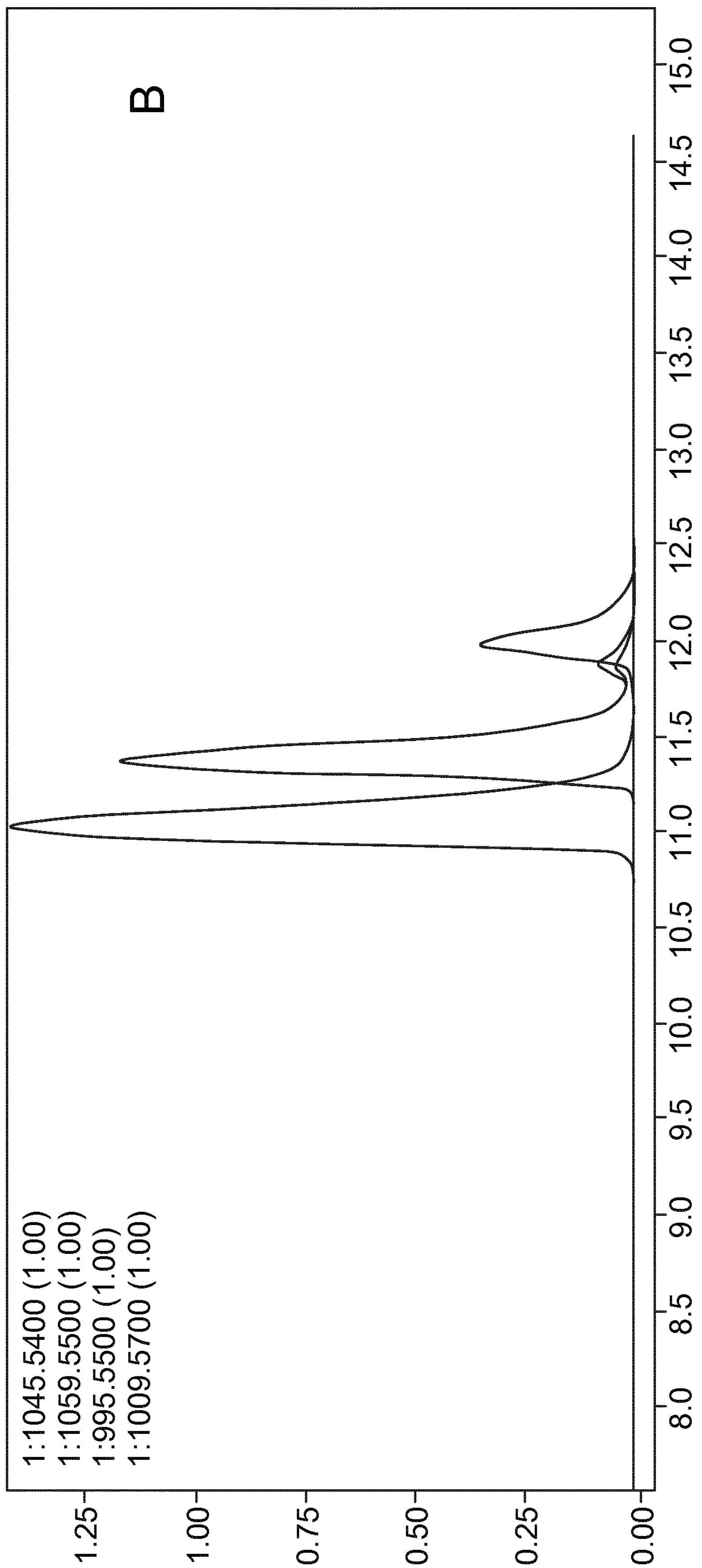
Figure 2C:
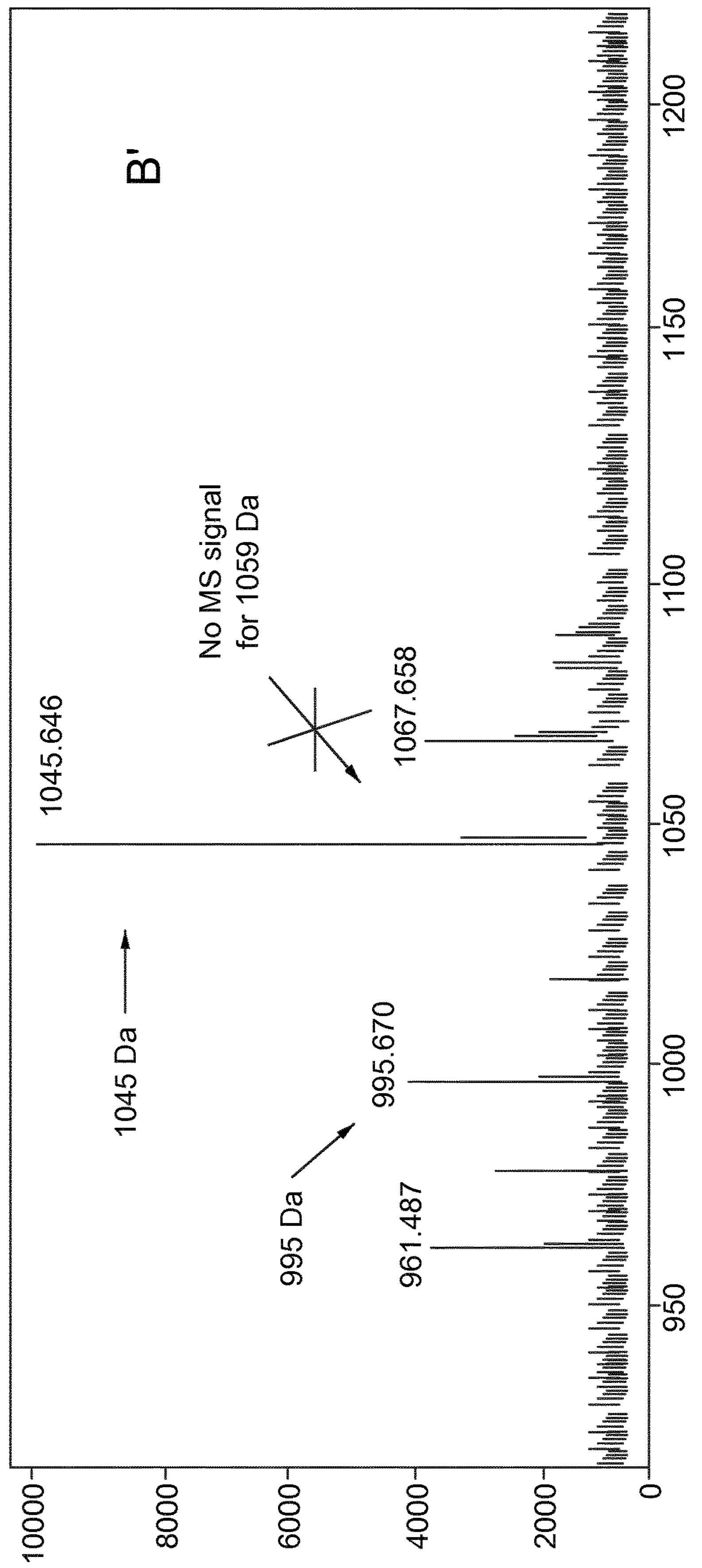
Figure 2C:
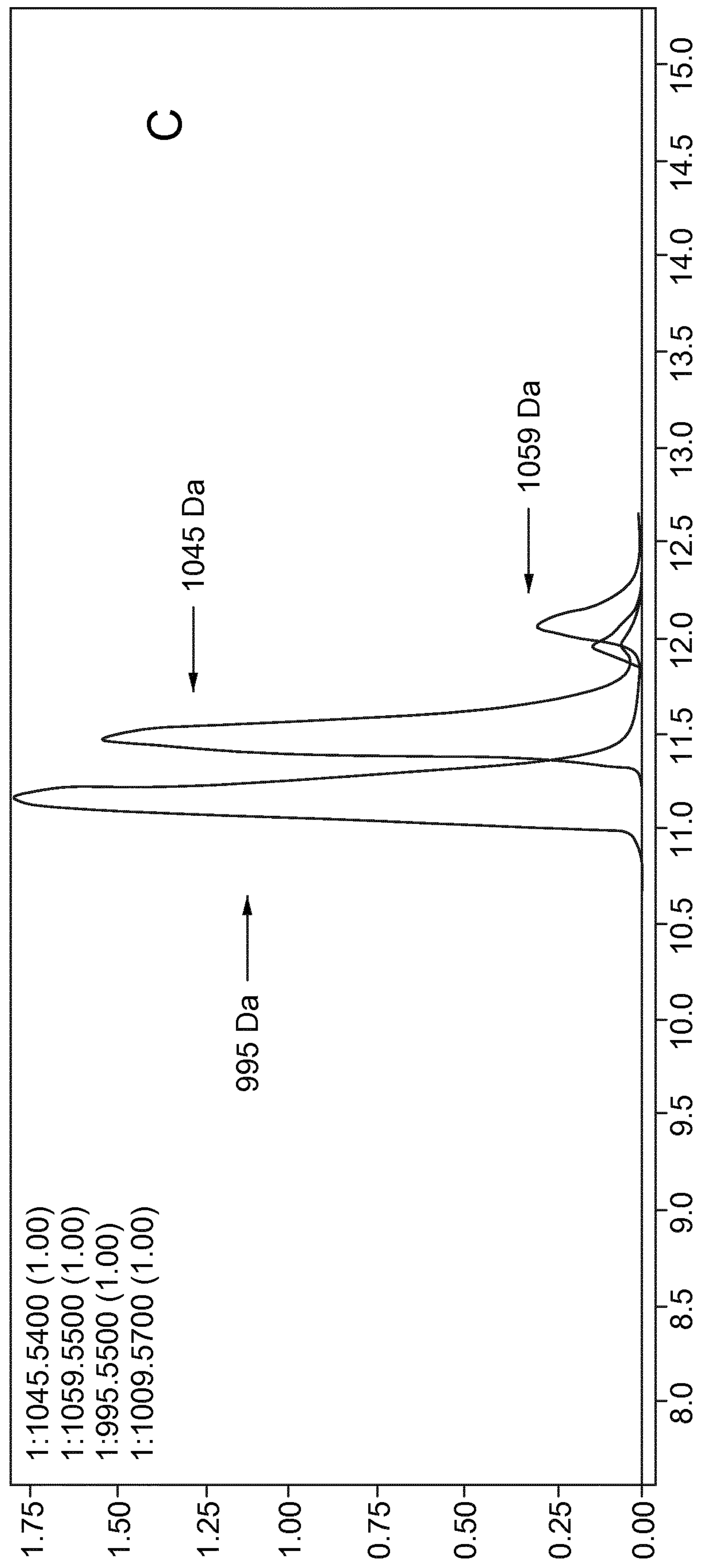
Figure 2C:
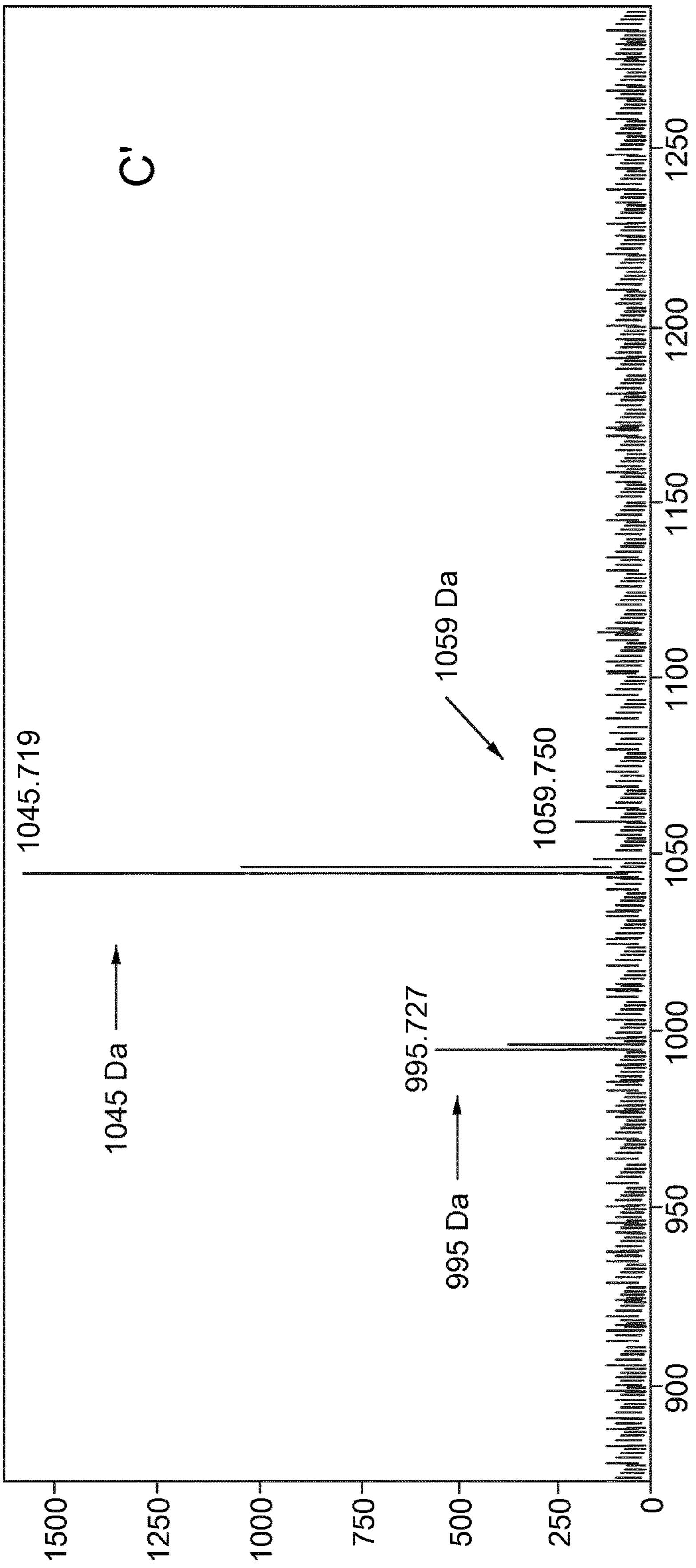
Figure 2C:
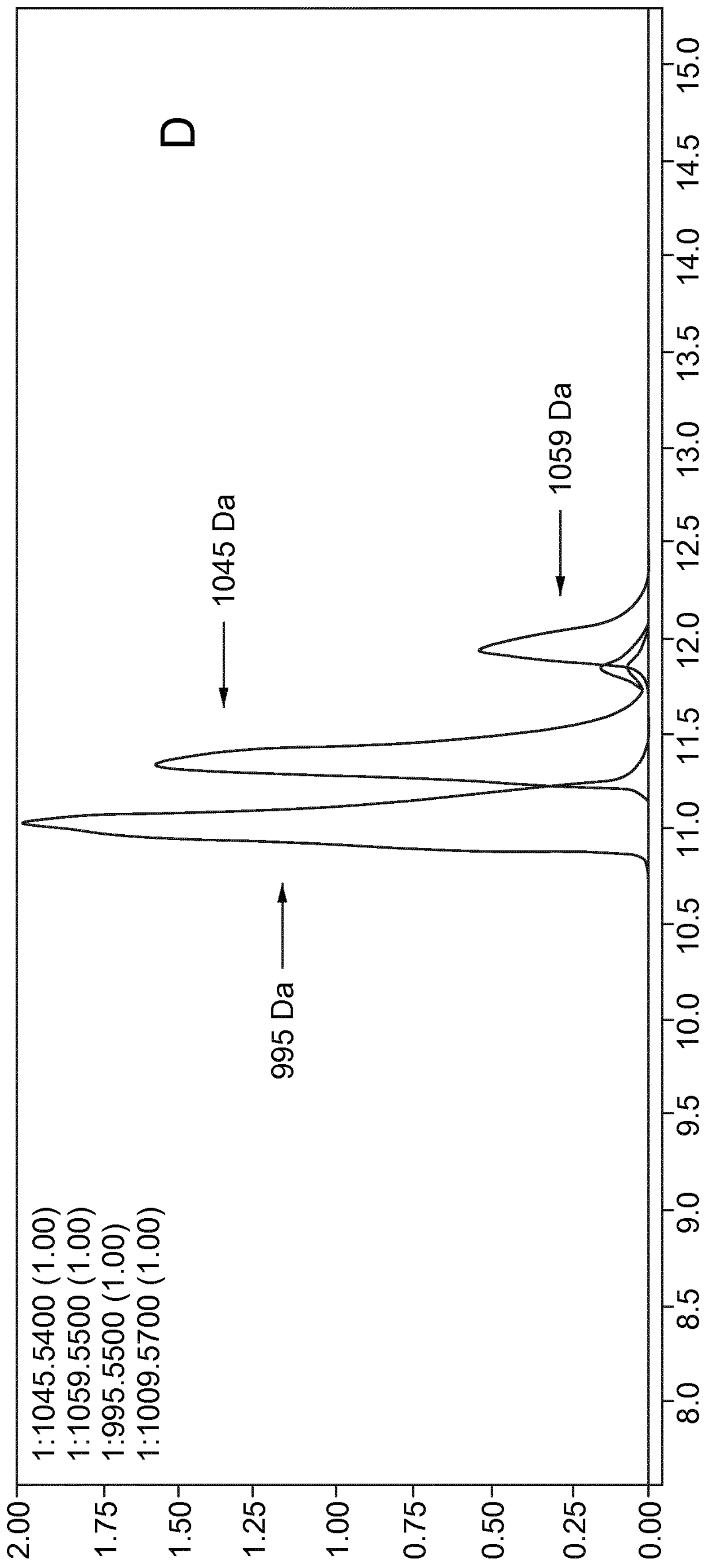
Figure 2C:
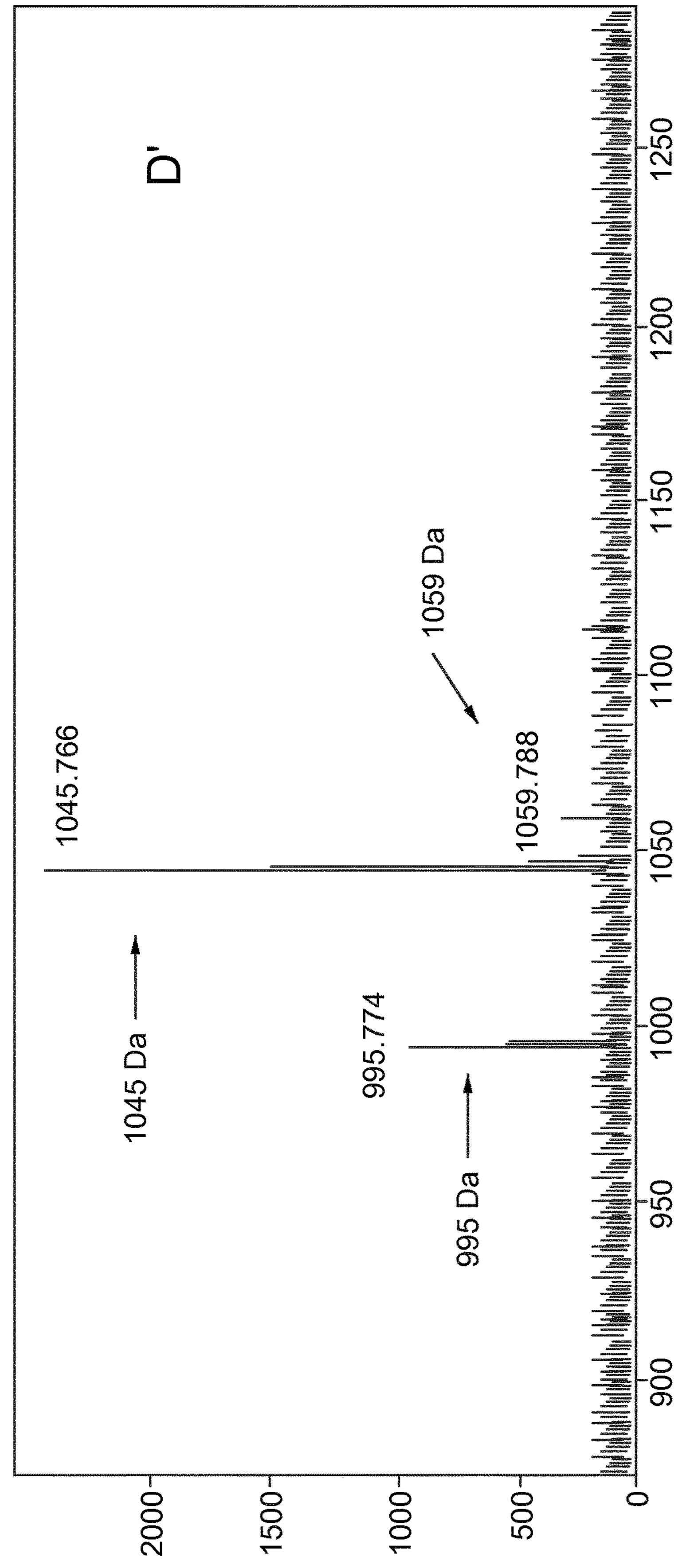
Figure 2C:
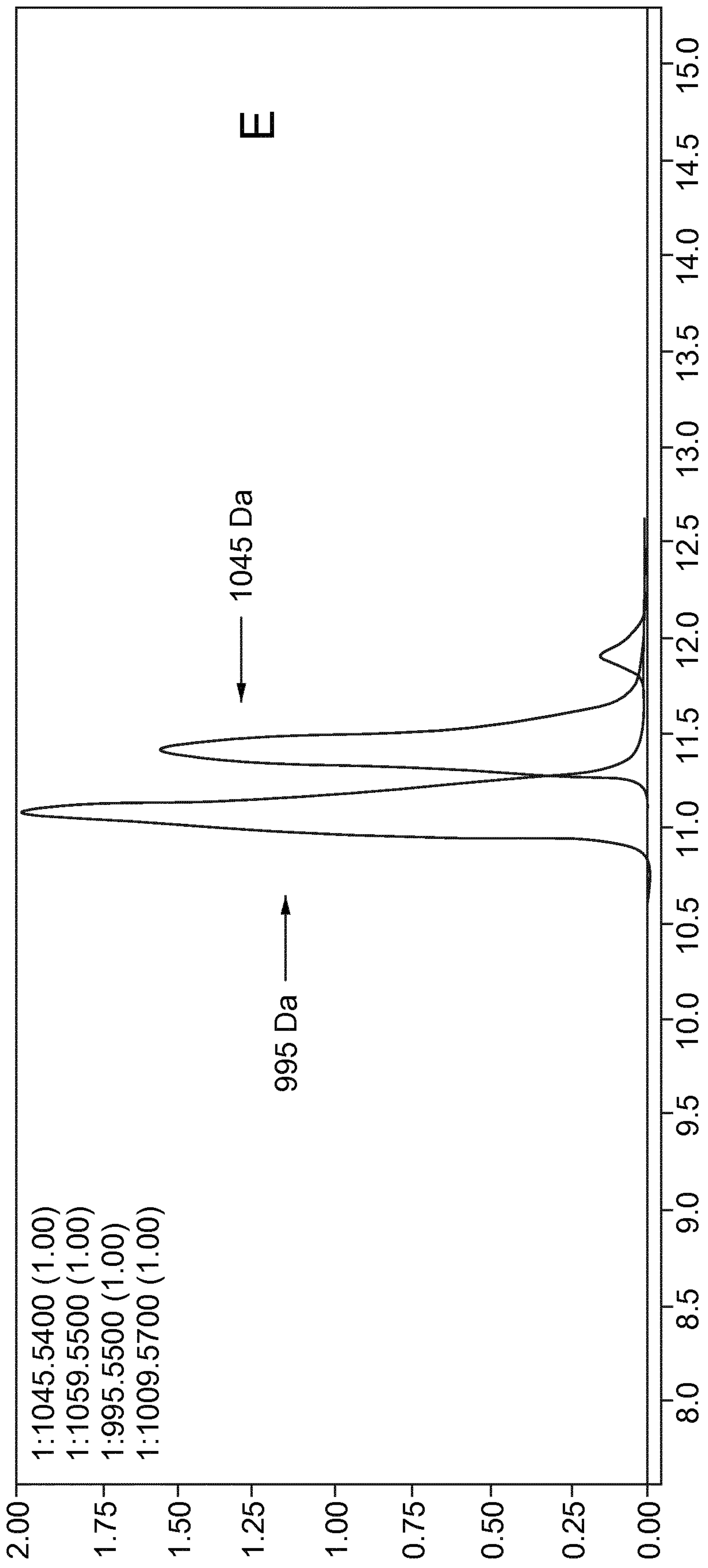
Figure 2C:
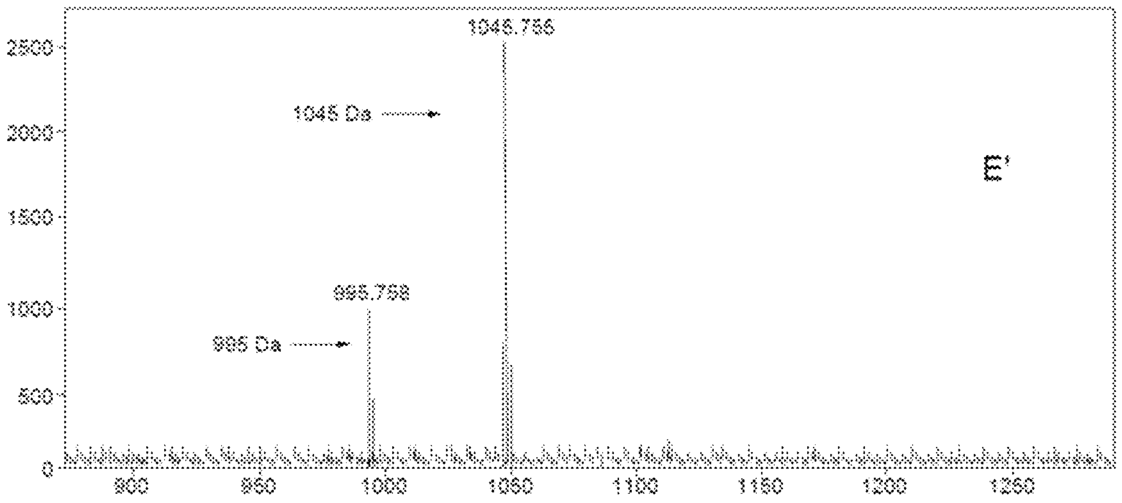
Figure 2D:
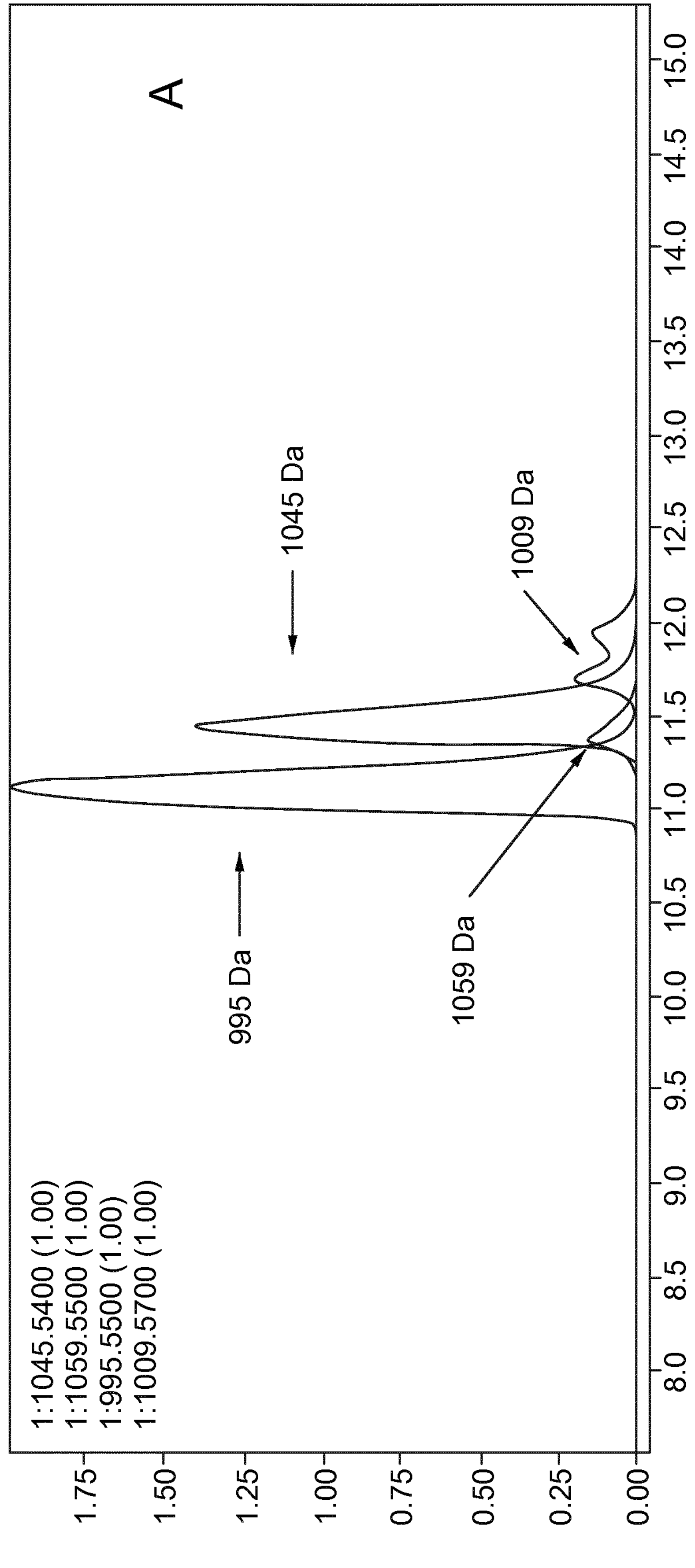
FIG. 2D: Detection of modified microcystins by two different mass spectrometry methods after feeding of modified substrates to a *Microcystis aeruginosa* strain CBT 480 with homoarginine in a 1.6 ml (dw-MTP) scale (ESI-IT-ToF-MS detection on the left; MALDI-ToF-MS detection on the right); A, A': feeding of 300 μM homoarginine (hR), w/o DMSO; B, B': feeding of 30 μM homoarginine (hR), w/o DMSO; C, C': feeding of 300 μM homoarginine (hR), w/1% DMSO; D, D': feeding of 30 μM homoarginine (hR), w/1% DMSO; E, E': control (no feeding); Molecule masses of naturally produced microcystins: 995 Da=MC-LR, 1045 Da=MC-YR; Molecule masses of modified microcystins generated by feeding with homoarginine: 1059 Da=MC-YhR; 1009 Da=MC-LhR.
Figure 2D:
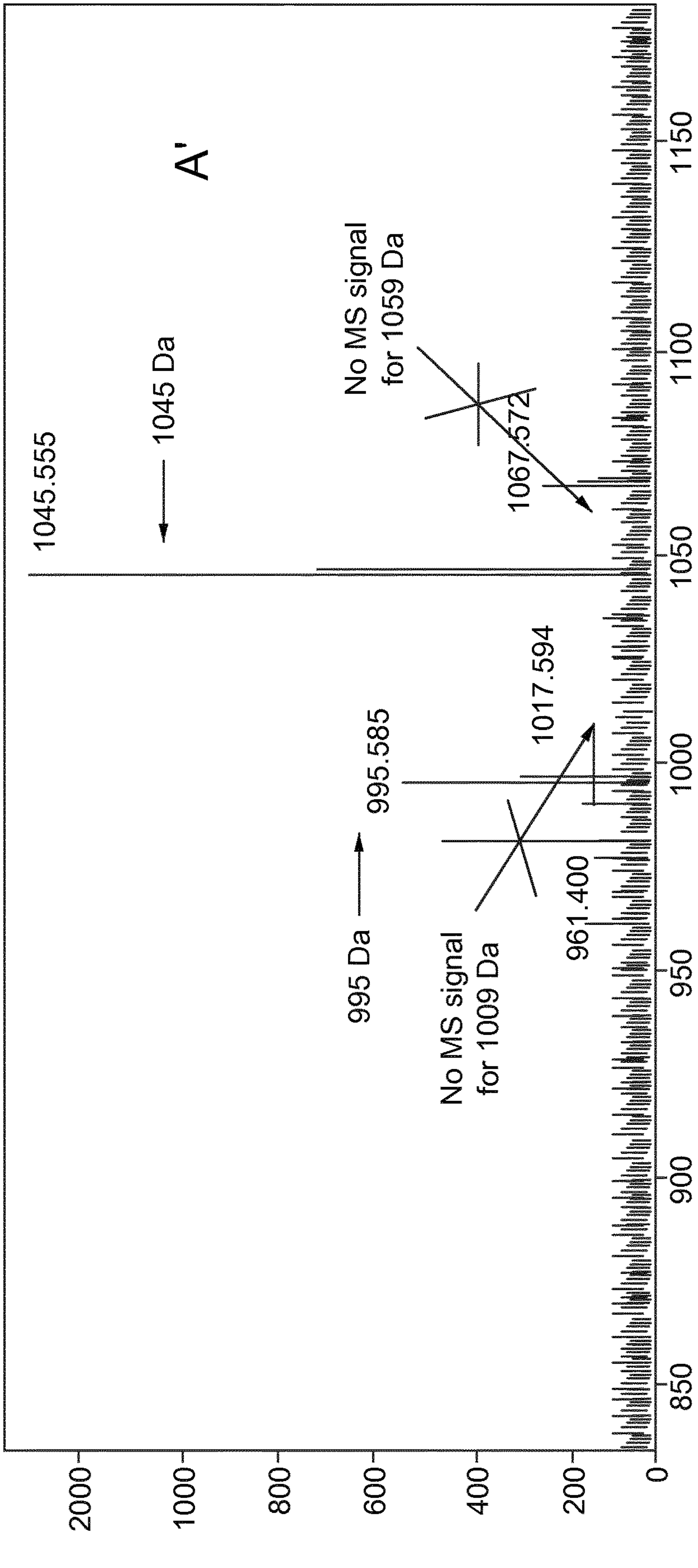
Figure 2D:
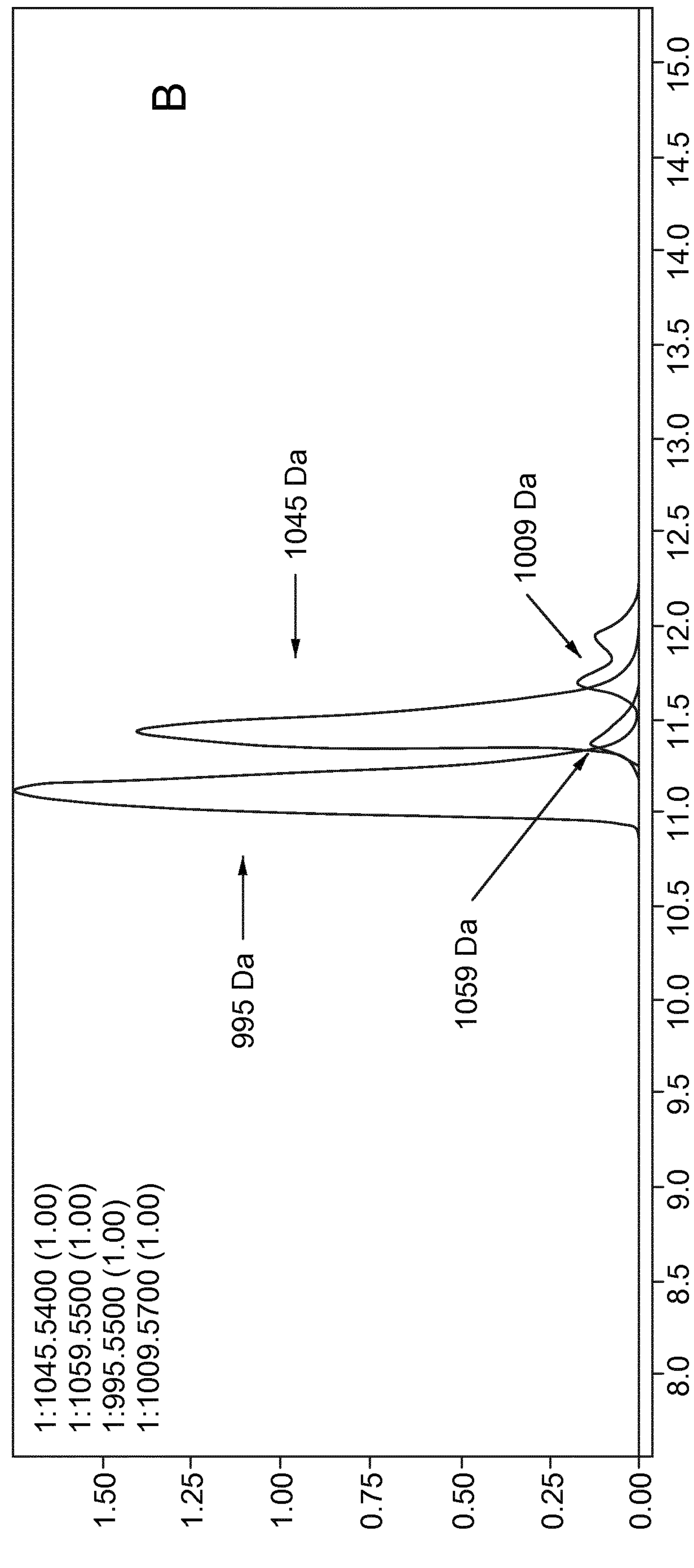
Figure 2D:
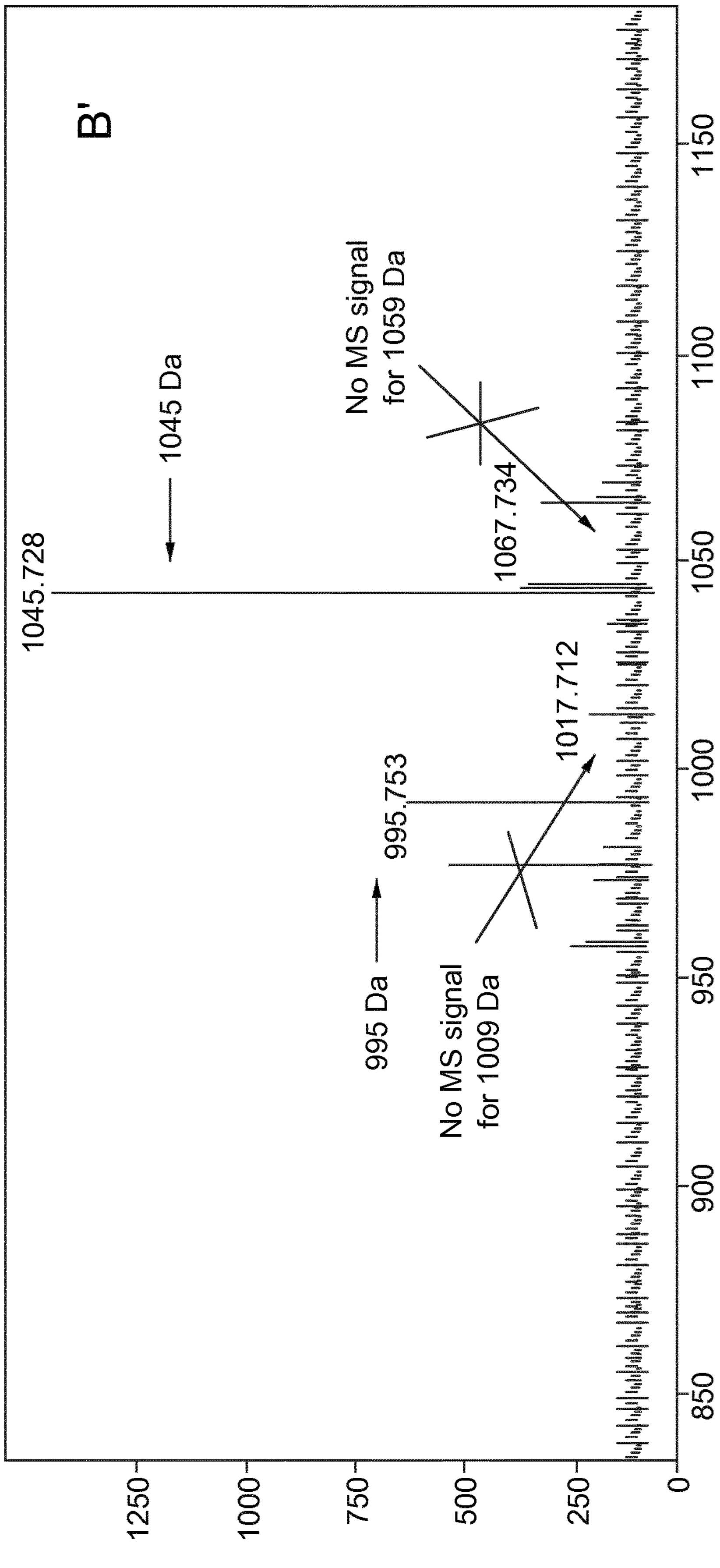
Figure 2D:
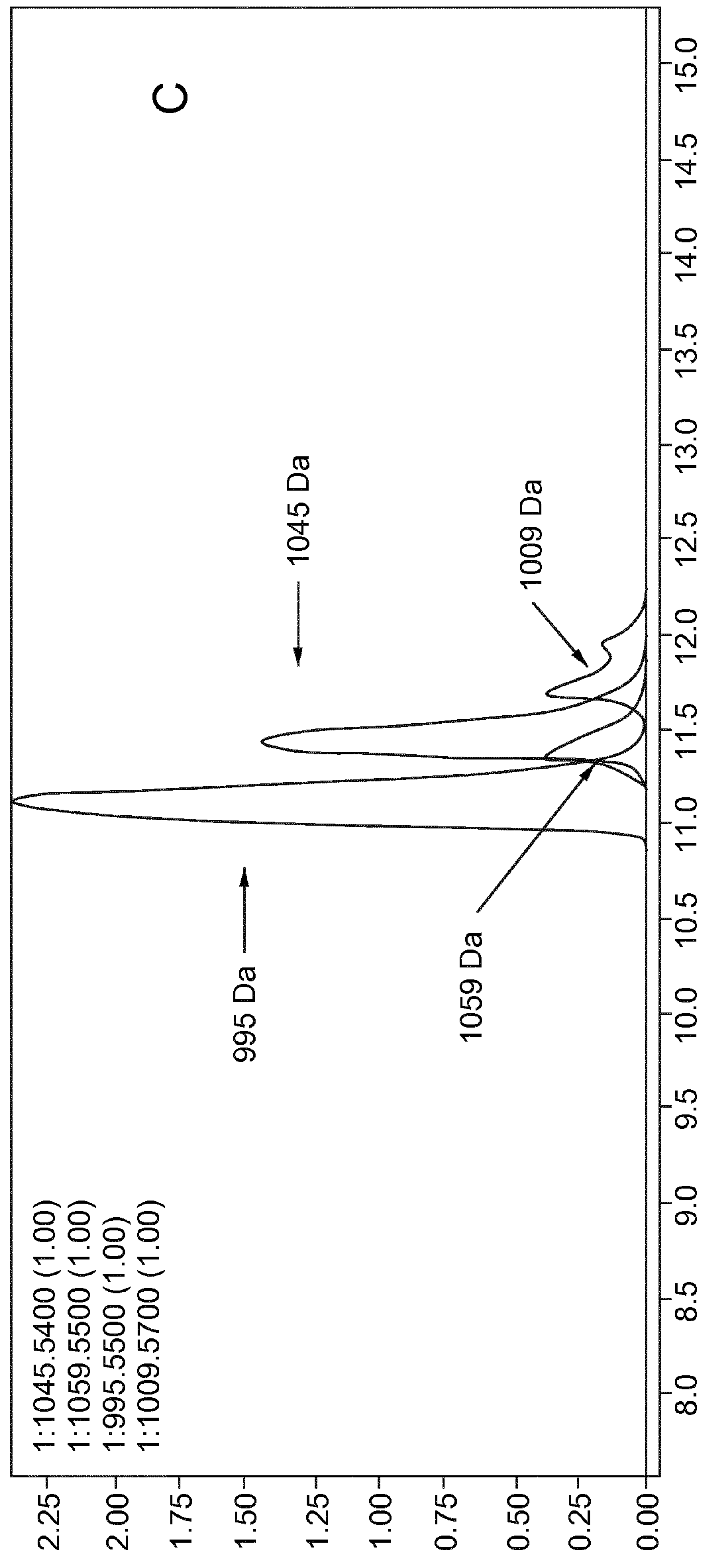
Figure 2D:
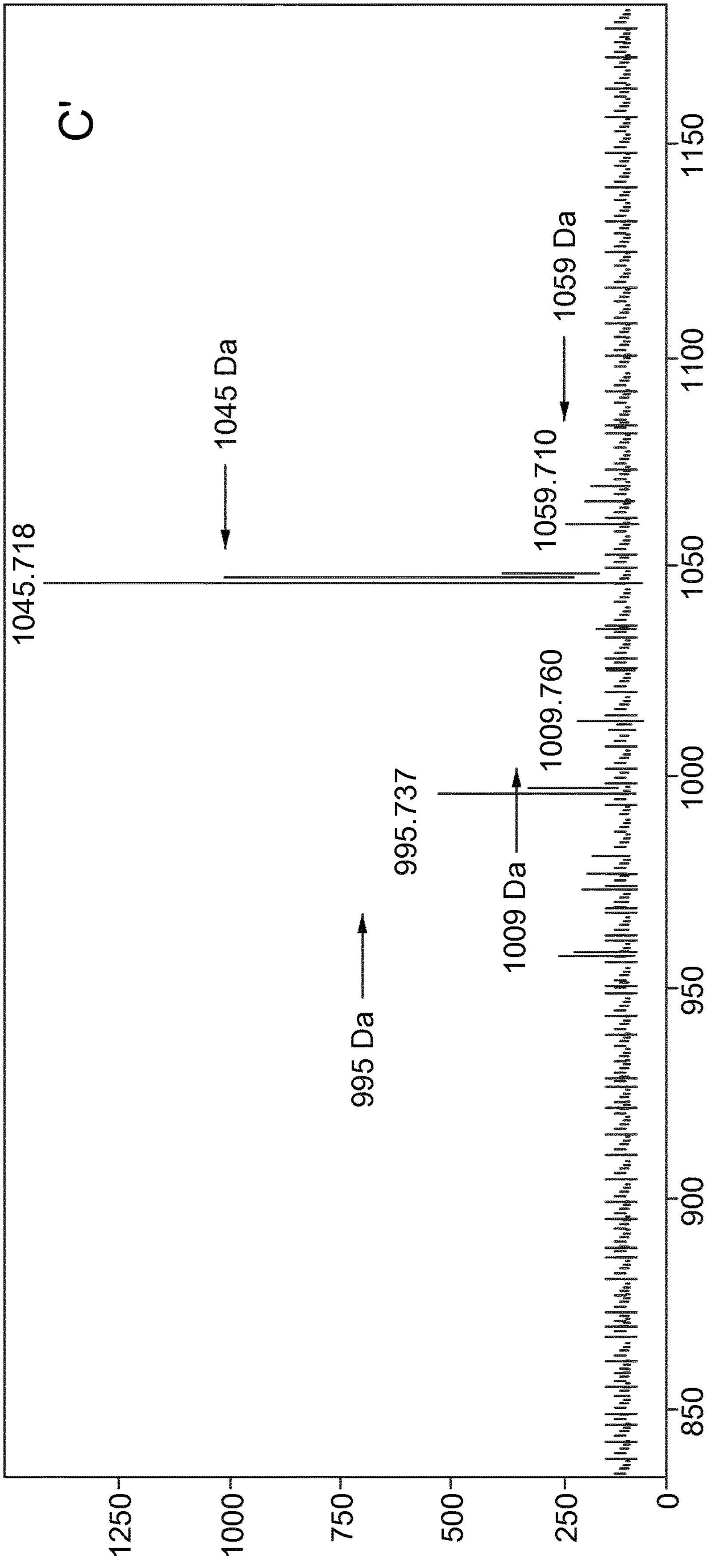
Figure 2D:
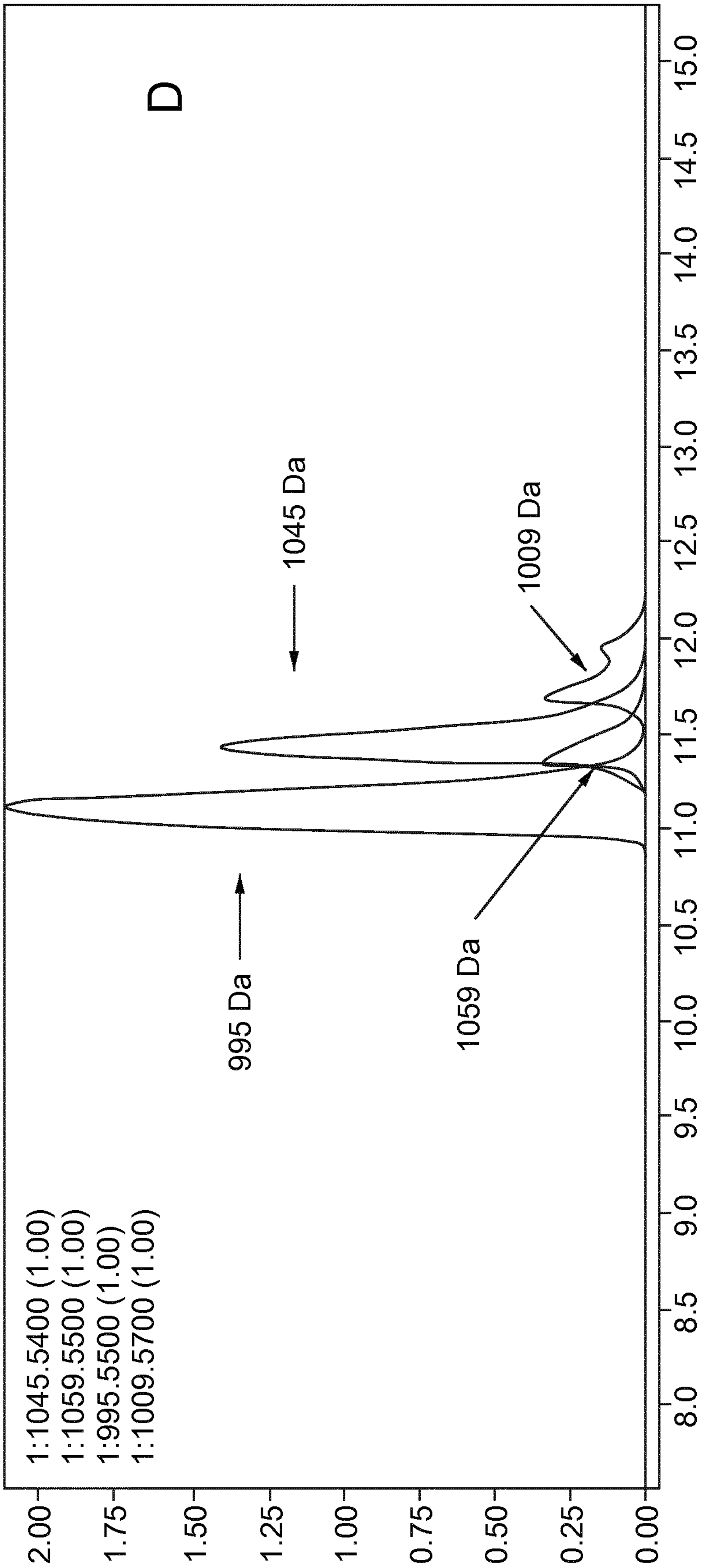
Figure 2D:
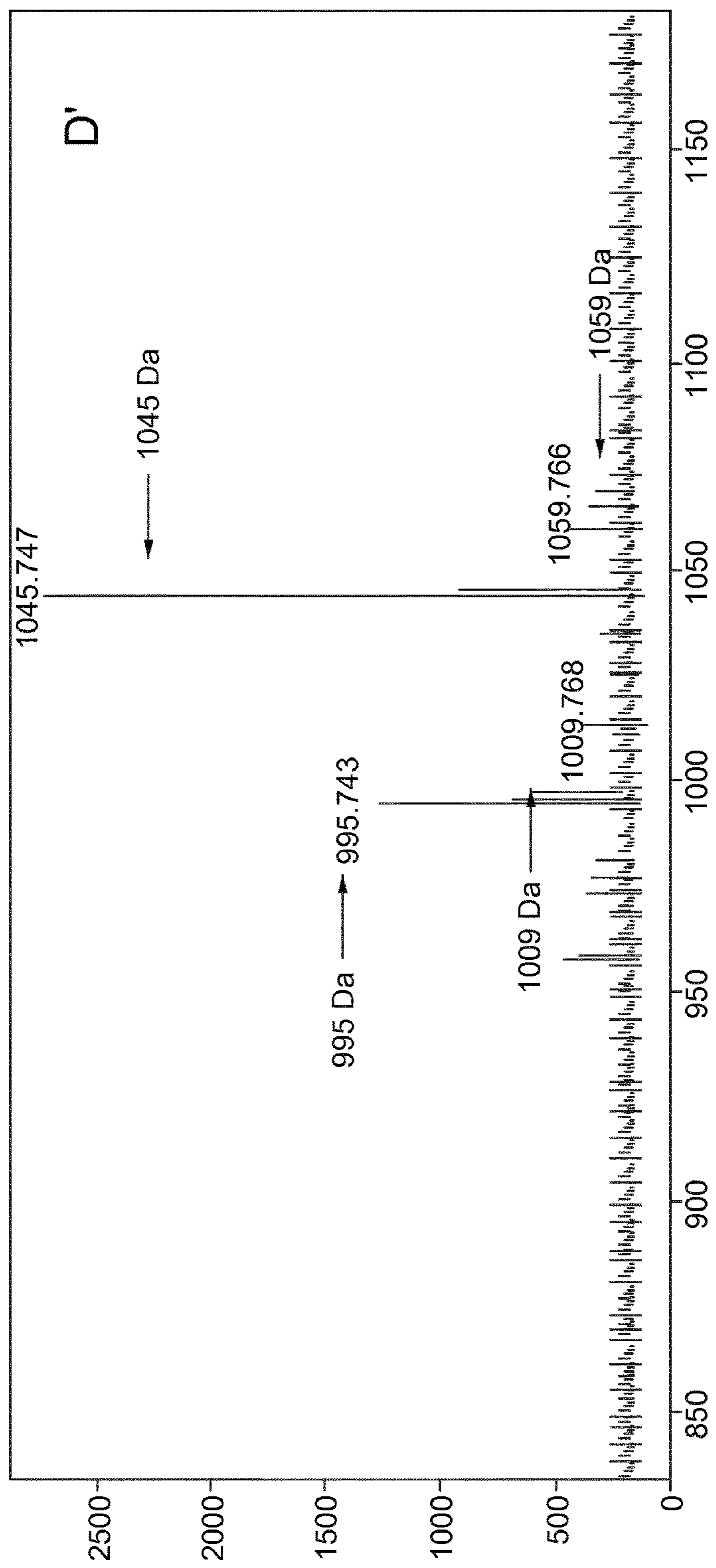
Figure 2D:
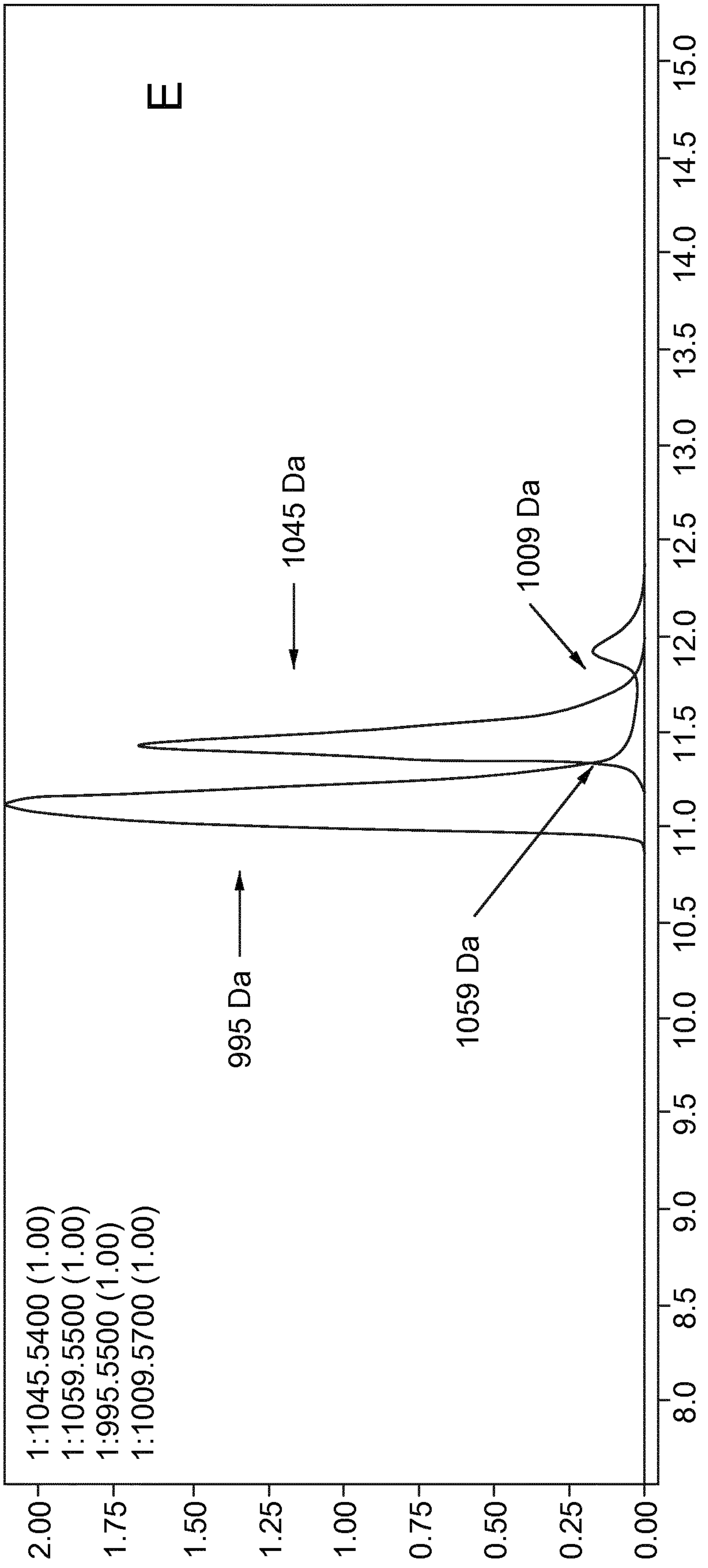
Figure 2D:
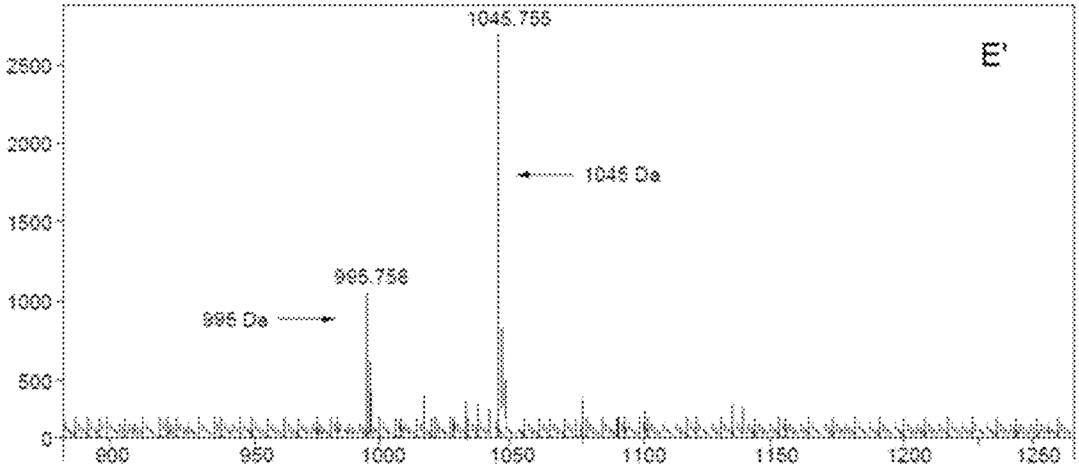
Figure 3:
FIG. 3: McyBI represents the first of two enzyme modules of McyB and is responsible for the incorporation of the amino acid at the position 2 of the microcystin molecule. This is the amino acid leucine in case of the Microcystin *aeruginosa* strain PCC7806 whereas it is leucine OR tyrosine in the *Microcystis aeruginosa* strain CBT 480. The so called core motifs A2-A6 of the adenylation (A) domain of McyBI are highlighted in black (A2-A6) and the amino acids responsible for substrate (amino acid) recognition and activation during the biosynthesis of the respective microcystin are indicated by big and bold white letters. These amino acids form the active pocket of the A domains and the sequence in their one-letter amino acid code represent the so called specificity-conferring code of A domains which shall allow for the prediction of substrate specificity of A domains. The only difference in the amino acid sequence of McyBI of both strains is in amino acid position 672. Only one of nine pocket-forming amino acids of the A domains of both strains is different between the strains and also the remaining parts of the A domain as well as of the whole biosynthetic gene clusters are almost identical between the strains leading to the conclusion that the incorporation of leucine and tyrosine at position 2 of the microcystin in the strain CBT 480 is a strain-specific feature but cannot be explained by differences in the DNA sequence of the biosynthetic gene clusters and amino acid sequence of the microcystin synthetases, resp. The consensus sequence as between the "Query" and "Sbjct" sequences is indicated by "Consensus" and corresponds to SEQ ID NO: 13. Each letter in the consensus sequence is an identical match. The blank spaces in the consensus sequence are where the match indicated a zero or negative score. The "+" symbol in the consensus sequence represents a conservative substitution. The "Query" sequence shown corresponds to SEQ ID NO: 11 and the "Sbjct" sequence shown corresponds to SEQ ID NO: 12.
Figure 4A:
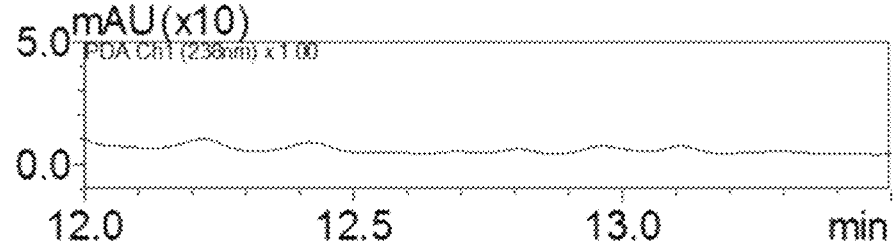
FIG. 4*a*: Exemplary embodiment No. 1: Incorporation of the modified substrate Azido-L-Phe (Phe=phenylalanine) into Microcystin-YR in position 2 produced by strain CBT 959. HPLC-PDA Chromatogram at 238 nm for sample of control cultivation, Detector signal intensities (y-Axis) are measured in milli-absorption units (mAU) and counts (dimensionless quantity) for PDA and mass spectrometry data, respectively. The growth of strain CBT 959 could not be followed by measurement of optical density at 750 nm ($OD_{750\ nm}$) as the cell formed aggregates making it impossible to measure reliable $OD_{750\ nm}$ values.
Figure 4B:
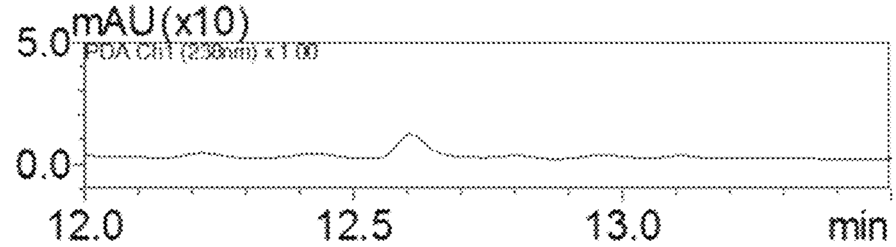
FIG. 4*b*: Exemplary embodiment No. 1: Incorporation of the modified substrate Azido-L-Phe (Phe=phenylalanine) into Microcystin-YR in position 2 produced by strain CBT 959. HPLC-PDA Chromatogram at 238 nm for sample of control cultivation for sample of cultivation with added modified substrate. Detector signal intensities (y-Axis) are measured in milli-absorption units (mAU) and counts (dimensionless quantity) for PDA and mass spectrometry data, respectively. The growth of strain CBT 959 could not be followed by measurement of optical density at 750 nm ($OD_{750\ nm}$) as the cell formed aggregates making it impossible to measure reliable $OD_{750\ nm}$ values.
Figure 4C:
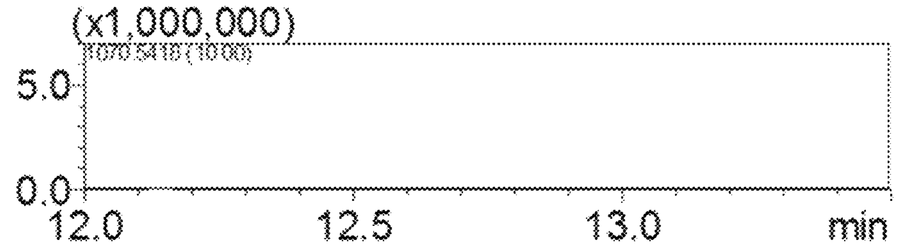
FIG. 4*c*: Exemplary embodiment No. 1: Incorporation of the modified substrate Azido-L-Phe (Phe=phenylalanine) into Microcystin-YR in position 2 produced by strain CBT 959. Extracted ion chromatogram from HPLC-MS data of mass value of protonated molecular ion of novel Microcystin variant for sample of control cultivation in the positive ionization mode. Detector signal intensities (y-Axis) are measured in milli-absorption units (mAU) and counts (dimensionless quantity) for PDA and mass spectrometry data, respectively. The growth of strain CBT 959 could not be followed by measurement of optical density at 750 nm ($OD_{750\ nm}$) as the cell formed aggregates making it impossible to measure reliable $OD_{750\ nm}$ values.
Figure 4D:
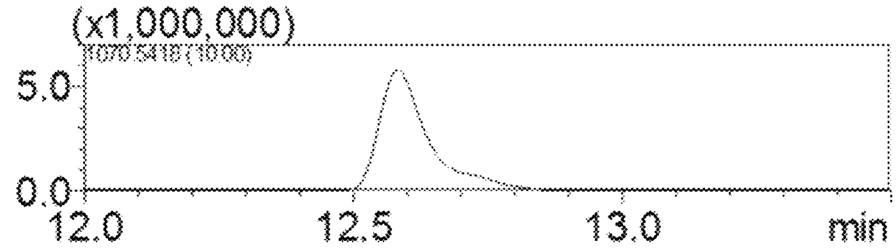
FIG. 4*d*: Exemplary embodiment No. 1: Incorporation of the modified substrate Azido-L-Phe (Phe=phenylalanine) into Microcystin-YR in position 2 produced by strain CBT 959. Extracted ion chromatogram from HPLC-MS data of mass value of protonated molecular ion of novel Microcystin variant for sample of cultivation with added modified substrate in the positive ionization mode. Detector signal intensities (y-Axis) are measured in milli-absorption units (mAU) and counts (dimensionless quantity) for PDA and mass spectrometry data, respectively. The growth of strain CBT 959 could not be followed by measurement of optical density at 750 nm ($OD_{750\ nm}$) as the cell formed aggregates making it impossible to measure reliable $OD_{750\ nm}$ values.
Figure 4E:
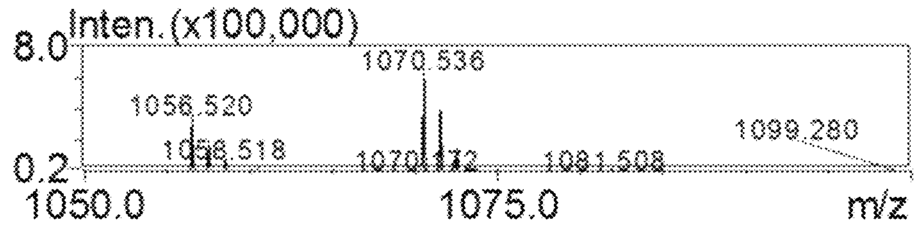
FIG. 4*e*: Exemplary embodiment No. 1: Incorporation of the modified substrate Azido-L-Phe (Phe=phenylalanine) into Microcystin-YR in position 2 produced by strain CBT 959. The averaged mass spectrum of the peak visible in chromatogram 4D is shown. Detector signal intensities (y-Axis) are measured in milli-absorption units (mAU) and counts (dimensionless quantity) for PDA and mass spectrometry data, respectively. The growth of strain CBT 959 could not be followed by measurement of optical density at 750 nm ($OD_{750\ nm}$) as the cell formed aggregates making it impossible to measure reliable $OD_{750\ nm}$ values.
Figure 5A:
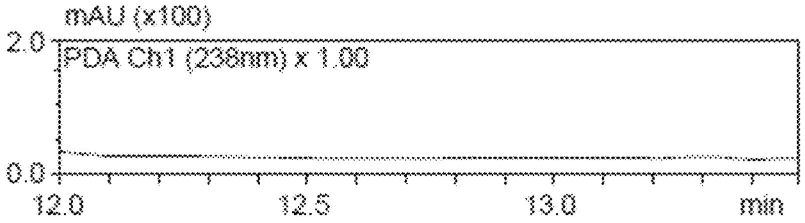
FIG. 5*a*: Exemplary embodiment No. 2: Incorporation of the modified substrate Prg-Tyr (Tyr=Tyrosine) into Microcystin YR in position 2 produced by strain CBT 480. HPLC-PDA Chromatogram at 238 nm for sample of control cultivation. Detector signal intensities (y-Axis) are measured in milli-absorption units (mAU) and counts (dimensionless quantity) for PDA and mass spectrometry data respectively.
Figure 5B:
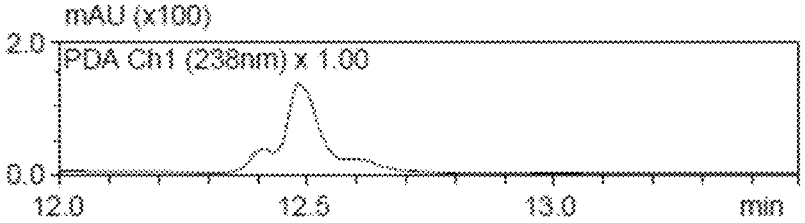
FIG. 5*b*: Exemplary embodiment No. 2: Incorporation of the modified substrate Prg-Tyr (Tyr=Tyrosine) into Microcystin YR in position 2 produced by strain CBT 480. HPLC-PDA Chromatogram at 238 nm for sample of cultivation with added modified substrate. Detector signal intensities (y-Axis) are measured in milli-absorption units (mAU) and counts (dimensionless quantity) for PDA and mass spectrometry data respectively.
Figure 5C:
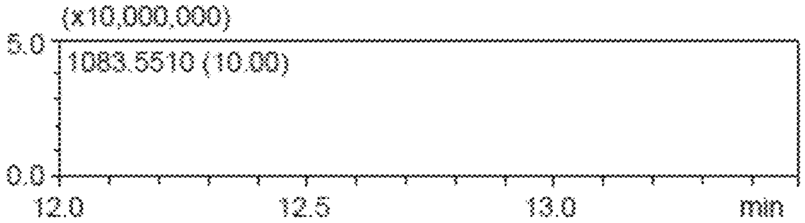
FIG. 5*c*: Exemplary embodiment No. 2: Incorporation of the modified substrate Prg-Tyr (Tyr=Tyrosine) into Microcystin YR in position 2 produced by strain CBT 480. Extracted ion chromatogram from HPLC-MS data of mass value of protonated molecular ion of novel Microcystin variant for sample of control cultivation in the positive ionization mode. Detector signal intensities (y-Axis) are measured in milli-absorption units (mAU) and counts (dimensionless quantity) for PDA and mass spectrometry data respectively.
Figure 5D:
FIG. 5*d*: Exemplary embodiment No. 2: Incorporation of the modified substrate Prg-Tyr (Tyr=Tyrosine) into Microcystin YR in position 2 produced by strain CBT 480. Extracted ion chromatogram from HPLC-MS data of mass value of protonated molecular ion of novel Microcystin variant for sample of cultivation with added modified substrate in the positive ionization mode. Detector signal intensities (y-Axis) are measured in milli-absorption units (mAU) and counts (dimensionless quantity) for PDA and mass spectrometry data respectively.
Figure 5E:
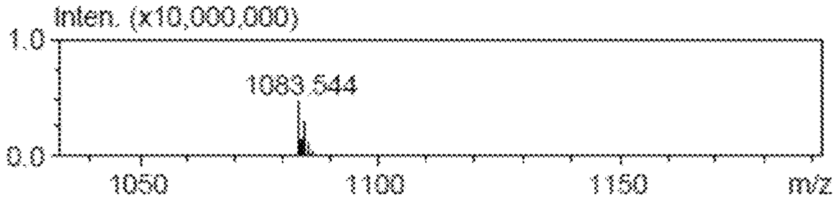
FIG. 5*e*: Exemplary embodiment No. 2: Incorporation of the modified substrate Prg-Tyr (Tyr=Tyrosine) into Microcystin YR in position 2 produced by strain CBT 480. (e) shows the averaged mass spectrum of the peak visible in chromatogram (d).
Figure 6:
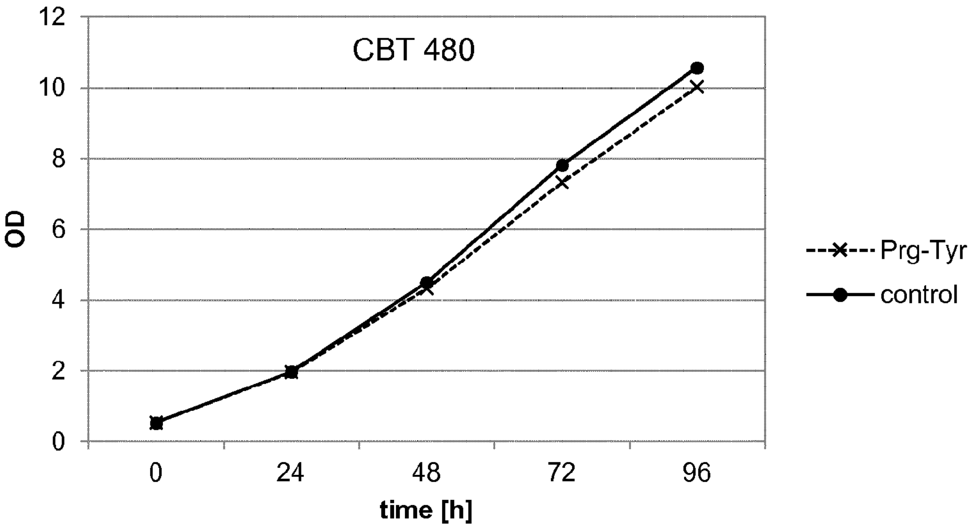
FIG. 6: Exemplary embodiment No. 2: Growths curve of CBT 480 cultures with and without Prg-Tyr (Tyr=Tyrosine) added.
Figure 7A:
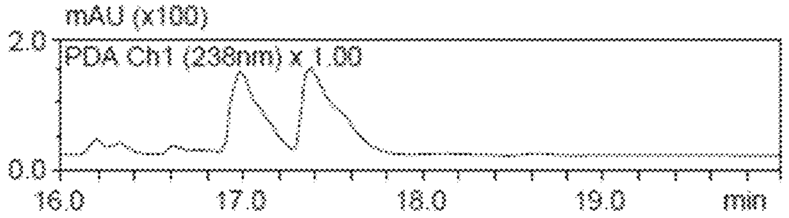
FIG. 7*a*: Exemplary embodiment No. 3: Incorporation of the modified substrate Azido-Lys (Lys=Lysine) into Microcystin LR in position 4 produced by strain CBT 275. HPLC-PDA Chromatogram at 238 nm for sample of control cultivation. Detector signal intensities (y-Axis) are measured in milli-absorption units (mAU) and counts (dimensionless quantity) for PDA and mass spectrometry data respectively.
Figure 7B:
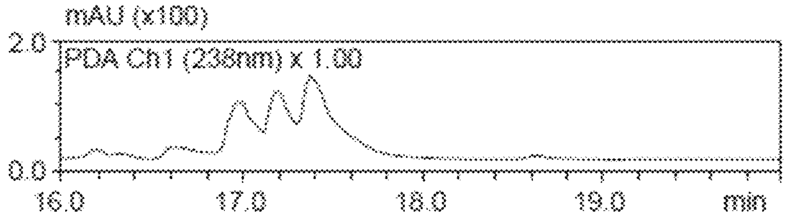
FIG. 7*b*: Exemplary embodiment No. 3: Incorporation of the modified substrate Azido-Lys (Lys=Lysine) into Microcystin LR in position 4 produced by strain CBT 275. HPLC-PDA Chromatogram at 238 nm for sample of cultivation with added modified substrate. Detector signal intensities (y-Axis) are measured in milli-absorption units (mAU) and counts (dimensionless quantity) for PDA and mass spectrometry data respectively.
Figure 7C:
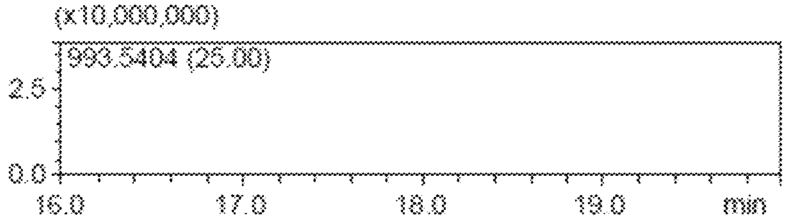
FIG. 7*c*: Exemplary embodiment No. 3: Incorporation of the modified substrate Azido-Lys (Lys=Lysine) into Microcystin LR in position 4 produced by strain CBT 275. Extracted ion chromatogram from HPLC-MS data of mass value of protonated molecular ion of novel Microcystin variant for sample of control cultivation in the positive ionization mode. Detector signal intensities (y-Axis) are measured in milli-absorption units (mAU) and counts (dimensionless quantity) for PDA and mass spectrometry data respectively.
Figure 7D:
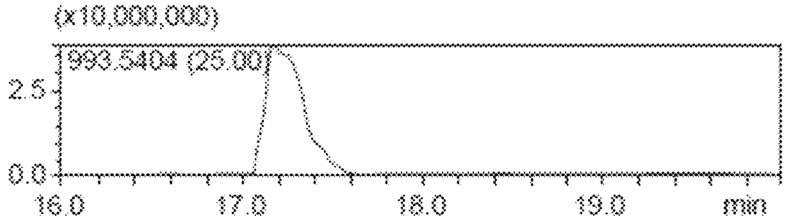
FIG. 7*d*: Exemplary embodiment No. 3: Incorporation of the modified substrate Azido-Lys (Lys=Lysine) into Microcystin LR in position 4 produced by strain CBT 275. Extracted ion chromatogram from HPLC-MS data of mass value of protonated molecular ion of novel Microcystin variant for sample of cultivation with added modified substrate in the positive ionization mode. Detector signal intensities (y-Axis) are measured in milli-absorption units (mAU) and counts (dimensionless quantity) for PDA and mass spectrometry data respectively.
Figure 7E:
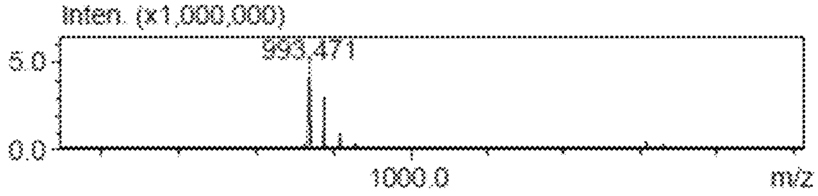
FIG. 7e: Exemplary embodiment No. 3: Incorporation of the modified substrate Azido-Lys (Lys=Lysine) into Microcystin LR in position 4 produced by strain CBT 275. (e) shows the averaged mass spectrum of the peak visible in chromatogram (d).
Figure 8:
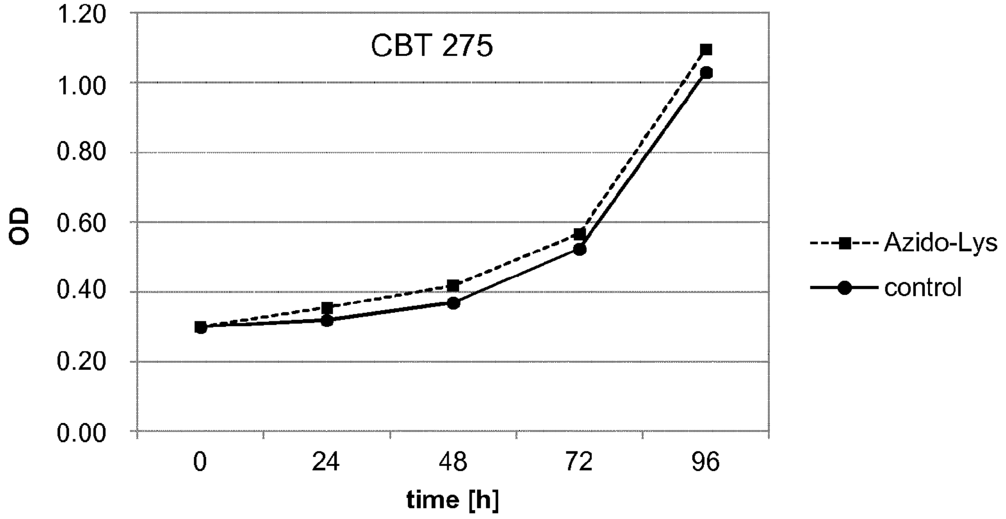
FIG. 8: Exemplary embodiment No. 3: Growths curve of CBT 275 cultures with and without Azido-Lys (Lys=Lysine) added.
Figure 9A:
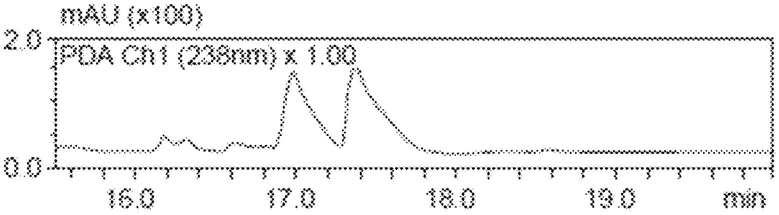
FIG. 9a: Exemplary embodiment No. 4: Incorporation of the modified substrate Prg-Tyr (Tyr=Tyrosine) into Microcystin LW in position 4 produced by strain CBT 275. HPLC-PDA Chromatogram at 238 nm for sample of control cultivation. Detector signal intensities (y-Axis) are measured in milli-absorption units (mAU) and counts (dimensionless quantity) for PDA and mass spectrometry data respectively.
Figure 9B:
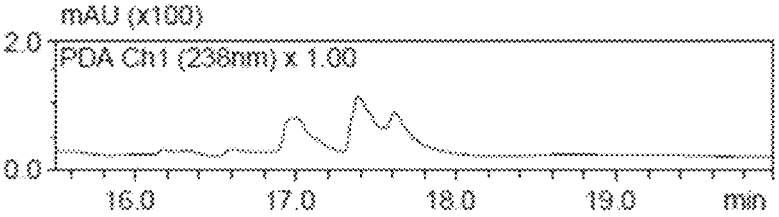
FIG. 9b: Exemplary embodiment No. 4: Incorporation of the modified substrate Prg-Tyr (Tyr=Tyrosine) into Microcystin LW in position 4 produced by strain CBT 275. HPLC-PDA Chromatogram at 238 nm for sample of cultivation with added modified substrate. Detector signal intensities (y-Axis) are measured in milli-absorption units (mAU) and counts (dimensionless quantity) for PDA and mass spectrometry data respectively.
Figure 9C:
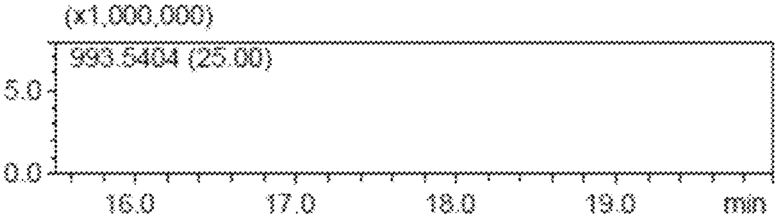
FIG. 9c: Exemplary embodiment No. 4: Incorporation of the modified substrate Prg-Tyr (Tyr=Tyrosine) into Microcystin LW in position 4 produced by strain CBT 275. Extracted ion chromatogram from HPLC-MS data of mass value of protonated molecular ion of novel Microcystin variant for sample of control cultivation in the positive ionization mode. Detector signal intensities (y-Axis) are measured in milli-absorption units (mAU) and counts (dimensionless quantity) for PDA and mass spectrometry data respectively.
Figure 9D:
FIG. 9d: Exemplary embodiment No. 4: Incorporation of the modified substrate Prg-Tyr (Tyr=Tyrosine) into Microcystin LW in position 4 produced by strain CBT 275. Extracted ion chromatogram from HPLC-MS data of mass value of protonated molecular ion of novel Microcystin variant for sample of cultivation with added modified substrate in the positive ionization mode. Detector signal intensities (y-Axis) are measured in milli-absorption units (mAU) and counts (dimensionless quantity) for PDA and mass spectrometry data respectively.
Figure 9E:
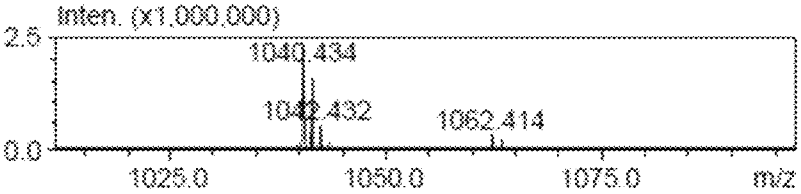
FIG. 9e: Exemplary embodiment No. 4: Incorporation of the modified substrate Prg-Tyr (Tyr=Tyrosine) into Microcystin LW in position 4 produced by strain CBT 275. (e) shows the averaged mass spectrum of the peak visible in chromatogram (d).
Figure 10:
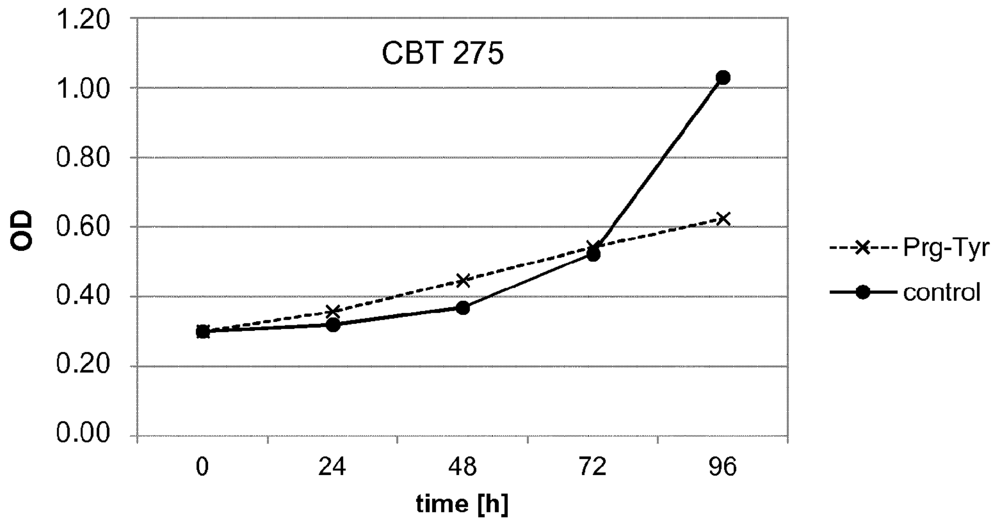
FIG. 10: Exemplary embodiment No. 4: Growths curve of CBT 275 cultures with and without Prg-Tyr (Tyr=Tyrosine) added.
Figure 11A:
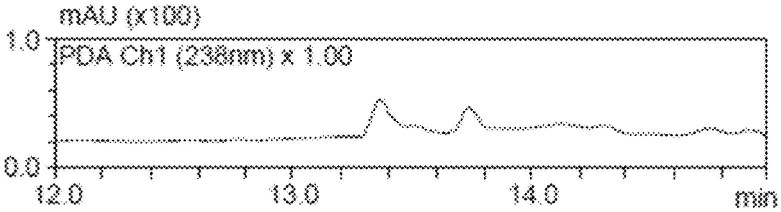
FIG. 11a: Exemplary embodiment No. 5: Incorporation of the modified substrate Nitro-Arg (Arg=Arginine) into Microcystin YR in position 4 produced by strain CBT 1. HPLC-PDA Chromatogram at 238 nm for sample of control cultivation. Detector signal intensities (y-Axis) are measured in milli-absorption units (mAU) and counts (dimensionless quantity) for PDA and mass spectrometry data respectively.
Figure 11B:
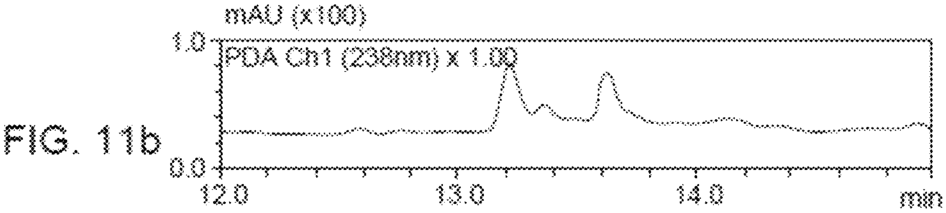
FIG. 11b: Exemplary embodiment No. 5: Incorporation of the modified substrate Nitro-Arg (Arg=Arginine) into Microcystin YR in position 4 produced by strain CBT 1. HPLC-PDA Chromatogram at 238 nm for sample of cultivation with added modified substrate. Detector signal intensities (y-Axis) are measured in milli-absorption units (mAU) and counts (dimensionless quantity) for PDA and mass spectrometry data respectively.
Figure 11C:
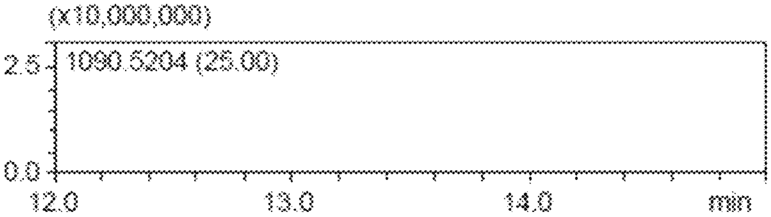
FIG. 11c: Exemplary embodiment No. 5: Incorporation of the modified substrate Nitro-Arg (Arg=Arginine) into Microcystin YR in position 4 produced by strain CBT 1. Extracted ion chromatogram from HPLC-MS data of mass value of protonated molecular ion of novel Microcystin variant for sample of control cultivation in the positive ionization mode. Detector signal intensities (y-Axis) are measured in milli-absorption units (mAU) and counts (dimensionless quantity) for PDA and mass spectrometry data respectively.
Figure 11D:
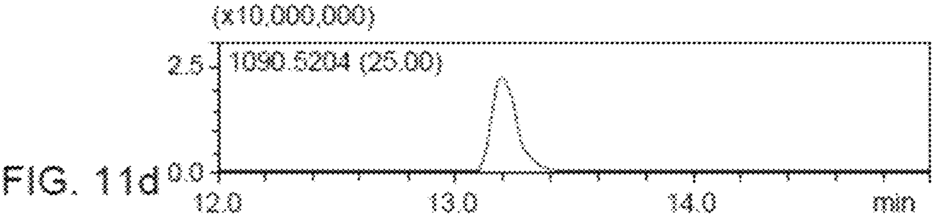
FIG. 11d: Exemplary embodiment No. 5: Incorporation of the modified substrate Nitro-Arg (Arg=Arginine) into Microcystin YR in position 4 produced by strain CBT 1. Extracted ion chromatogram from HPLC-MS data of mass value of protonated molecular ion of novel Microcystin variant for sample of cultivation with added modified substrate in the positive ionization mode. Detector signal intensities (y-Axis) are measured in milli-absorption units (mAU) and counts (dimensionless quantity) for PDA and mass spectrometry data respectively.
Figure 11E:
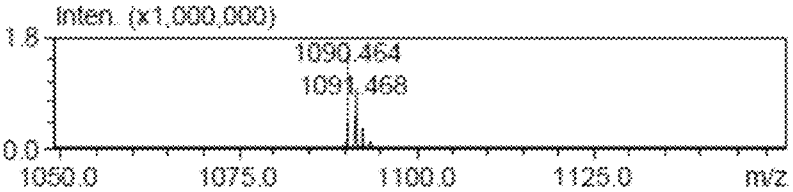
FIG. 11e: Exemplary embodiment No. 5: Incorporation of the modified substrate Nitro-Arg (Arg=Arginine) into Microcystin YR in position 4 produced by strain CBT 1. (e) shows the averaged mass spectrum of the peak visible in chromatogram (d).
Figure 12:
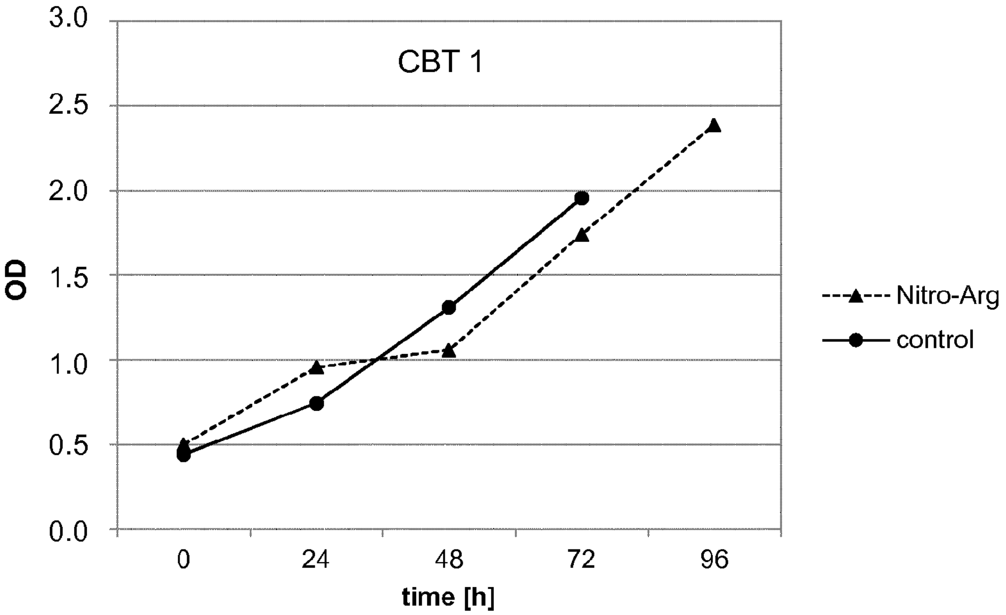
FIG. 12: Growths curve of CBT 1 cultures with and without Nitro-Arg (Arg=Arginine) added.
Figure 13A:
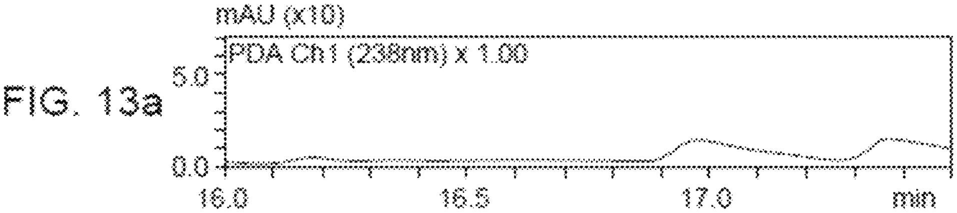
FIG. 13a: Exemplary embodiment No. 6: Incorporation of the modified substrate Furyl-L-Ala (Ala=Alanine) into Microcystin LR in position 4 produced by strain CBT 275. HPLC-PDA Chromatogram at 238 nm for sample of cultivation. Detector signal intensities (y-Axis) are measured in milli-absorption units (mAU) and counts (dimensionless quantity) for PDA and mass spectrometry data respectively.
Figure 13B:
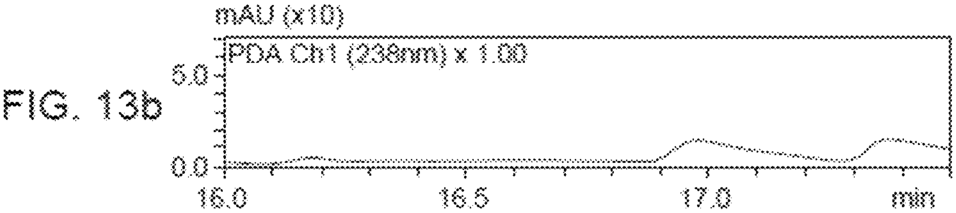
FIG. 13b: Exemplary embodiment No. 6: Incorporation of the modified substrate Furyl-L-Ala (Ala=Alanine) into Microcystin LR in position 4 produced by strain CBT 275. HPLC-PDA Chromatogram at 238 nm for sample of control cultivation with added modified substrate. Detector signal intensities (y-Axis) are measured in milli-absorption units (mAU) and counts (dimensionless quantity) for PDA and mass spectrometry data respectively. The PDA-Signal of the novel Furyl-Ala variant of Microcystin LR is not visible due to the low concentration.
Figure 13C:
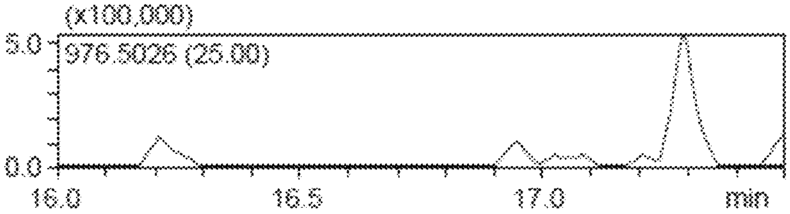
FIG. 13c: Exemplary embodiment No. 6: Incorporation of the modified substrate Furyl-L-Ala (Ala=Alanine) into Microcystin LR in position 4 produced by strain CBT 275. Extracted ion chromatogram from HPLC-MS data of mass value of protonated molecular ion of novel Microcystin variant for sample of control cultivation in the positive ionization mode. Detector signal intensities (y-Axis) are measured in milli-absorption units (mAU) and counts (dimensionless quantity) for PDA and mass spectrometry data respectively.
Figure 13D:
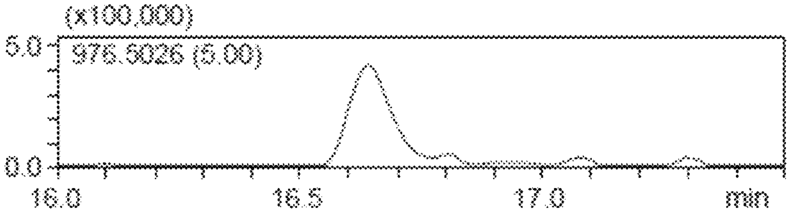
FIG. 13d: Exemplary embodiment No. 6: Incorporation of the modified substrate Furyl-L-Ala (Ala=Alanine) into Microcystin LR in position 4 produced by strain CBT 275. Extracted ion chromatogram from HPLC-MS data of mass value of protonated molecular ion of novel Microcystin variant for sample of cultivation with added modified substrate in the positive ionization mode. Detector signal intensities (y-Axis) are measured in milli-absorption units (mAU) and counts (dimensionless quantity) for PDA and mass spectrometry data respectively. The PDA-Signal of the novel Furyl-Ala variant of Microcystin LR is not visible due to the low concentration.
Figure 13E:
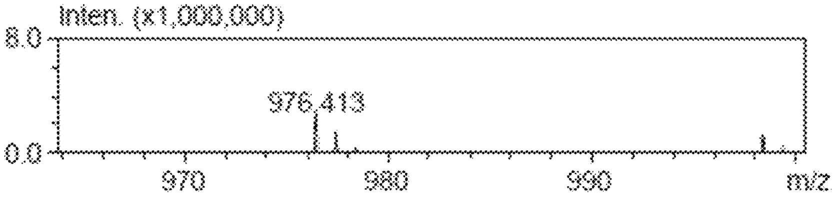
FIG. 13*e*: Exemplary embodiment No. 6: Incorporation of the modified substrate Furyl-L-Ala (Ala=Alanine) into Microcystin LR in position 4 produced by strain CBT 275. (e) shows the averaged mass spectrum of the peak visible in chromatogram (d).
Figure 14:
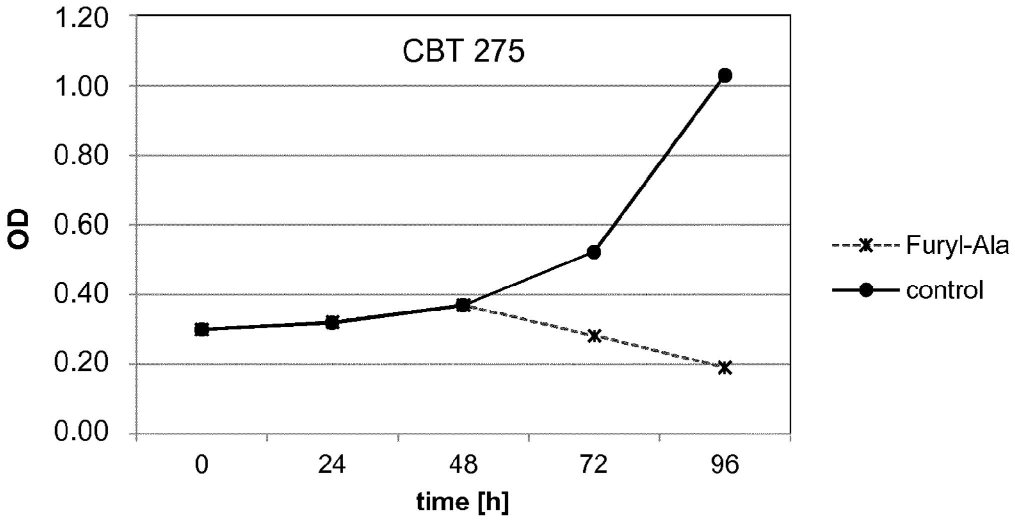
FIG. 14: Exemplary embodiment No. 6: Growths curve of CBT 275 cultures with and without Furyl-Ala (Ala=Alanine) added.
Figure 15A:
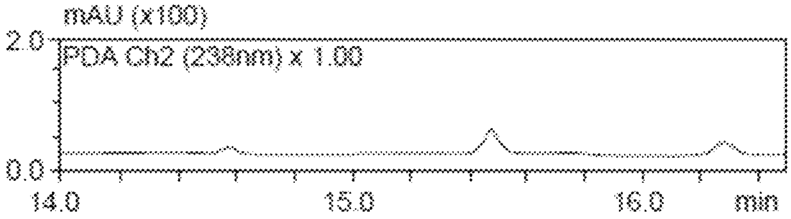
FIG. 15*a*: Exemplary embodiment No. 7: Incorporation of the modified substrate Nitro-Arg (Arg=Arginine) and Prg-Tyr (Tyr=Tyrosine) into Microcystin YR in position 2 and 4 respectively produced by strain CBT 480. HPLC-PDA Chromatogram at 238 nm for sample of control cultivation. Detector signal intensities (y-Axis) are measured in milli-absorption units (mAU) and counts (dimensionless quantity) for PDA and mass spectrometry data respectively.
Figure 15B:
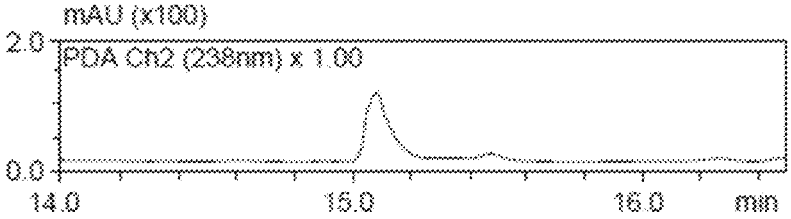
FIG. 15*b*: Exemplary embodiment No. 7: Incorporation of the modified substrate Nitro-Arg (Arg=Arginine) and Prg-Tyr (Tyr=Tyrosine) into Microcystin YR in position 2 and 4 respectively produced by strain CBT 480. HPLC-PDA Chromatogram at 238 nm for sample of cultivation with added modified substrate. Detector signal intensities (y-Axis) are measured in milli-absorption units (mAU) and counts (dimensionless quantity) for PDA and mass spectrometry data respectively.
Figure 15C:
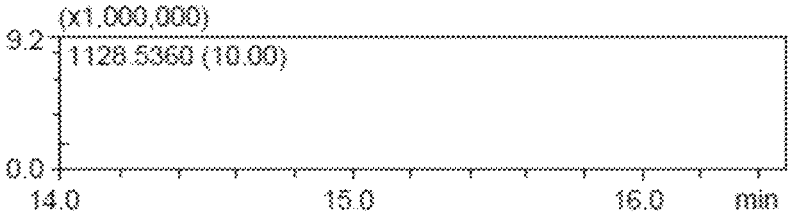
FIG. 15*c*: Exemplary embodiment No. 7: Incorporation of the modified substrate Nitro-Arg (Arg=Arginine) and Prg-Tyr (Tyr=Tyrosine) into Microcystin YR in position 2 and 4 respectively produced by strain CBT 480. Extracted ion chromatogram from HPLC-MS data of mass value of protonated molecular ion of novel Microcystin variant for sample of control cultivation in the positive ionization mode. Detector signal intensities (y-Axis) are measured in milli-absorption units (mAU) and counts (dimensionless quantity) for PDA and mass spectrometry data respectively.
Figure 15D:
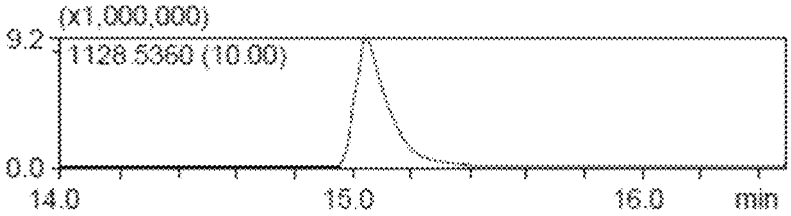
FIG. 15*d*: Exemplary embodiment No. 7: Incorporation of the modified substrate Nitro-Arg (Arg=Arginine) and Prg-Tyr (Tyr=Tyrosine) into Microcystin YR in position 2 and 4 respectively produced by strain CBT 480. Extracted ion chromatogram from HPLC-MS data of mass value of protonated molecular ion of novel Microcystin variant for sample of cultivation with added modified substrate in the positive ionization mode. Detector signal intensities (y-Axis) are measured in milli-absorption units (mAU) and counts (dimensionless quantity) for PDA and mass spectrometry data respectively.
Figure 15E:
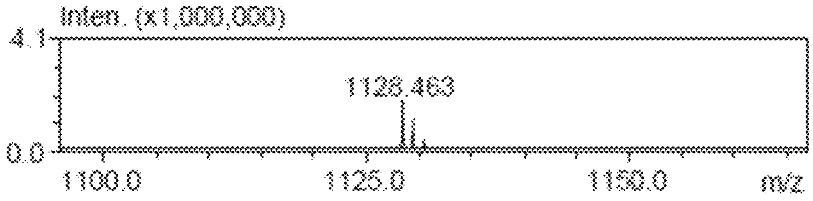
FIG. 15*e*: Exemplary embodiment No. 7: Incorporation of the modified substrate Nitro-Arg (Arg=Arginine) and Prg-Tyr (Tyr=Tyrosine) into Microcystin YR in position 2 and 4 respectively produced by strain CBT 480. (e) shows the averaged mass spectrum of the peak visible in chromatogram (d).
Figure 16:
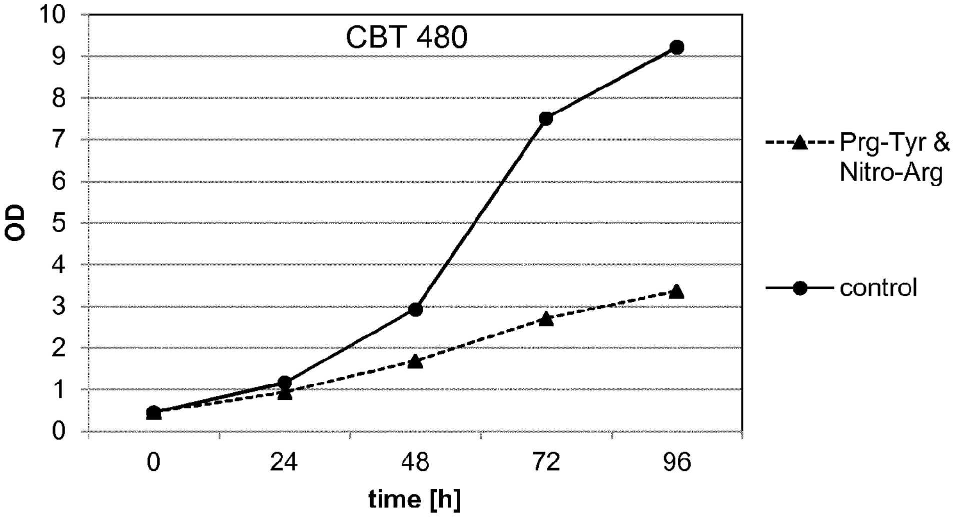
FIG. 16: Exemplary embodiment No. 7: Growths curve of CBT 480 cultures with and without Nitro-Arg (Arg=Arginine) and Prg-Tyr (Tyr=Tyrosine) added.
Figure 17A:
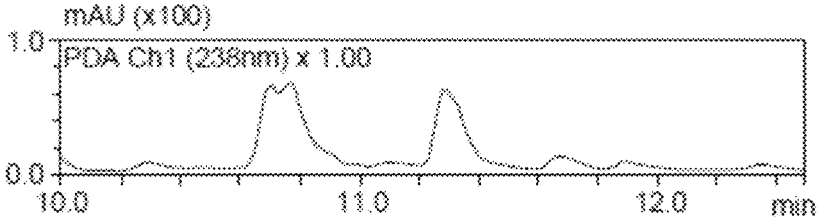
FIG. 17*a*: Exemplary embodiment No. 8: Incorporation of the modified substrate Nitro-Arg (Arg=Arginine) into Microcystin (D-Asp3, E-Dhb7)-RR in position 2/4 produced by strain CBT 329. HPLC-PDA Chromatogram at 238 nm for sample of control cultivation. Detector signal intensities (y-Axis) are measured in milli-absorption units (mAU) and counts (dimensionless quantity) for PDA and mass spectrometry data respectively.
Figure 17B:
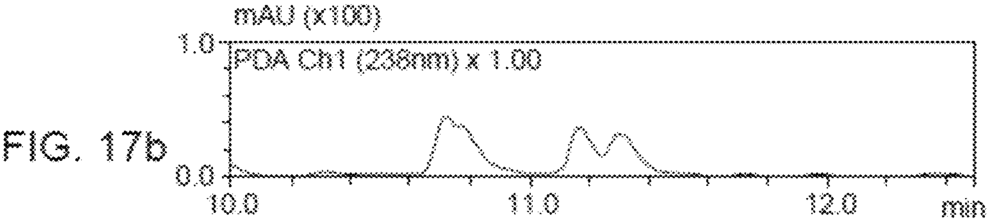
FIG. 17*b*: Exemplary embodiment No. 8: Incorporation of the modified substrate Nitro-Arg (Arg=Arginine) into Microcystin (D-Asp3, E-Dhb7)-RR in position 2/4 produced by strain CBT 329. HPLC-PDA Chromatogram at 238 nm for sample of cultivation with added modified substrate. Detector signal intensities (y-Axis) are measured in milli-absorption units (mAU) and counts (dimensionless quantity) for PDA and mass spectrometry data respectively.
Figure 17C:
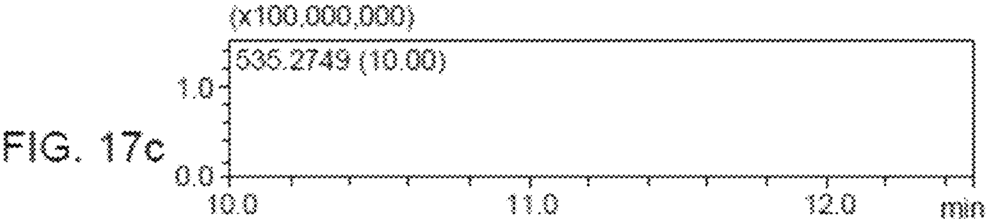
FIG. 17*c*: Exemplary embodiment No. 8: Incorporation of the modified substrate Nitro-Arg (Arg=Arginine) into Microcystin (D-Asp3, E-Dhb7)-RR in position 2/4 produced by strain CBT 329. Extracted ion chromatogram from HPLC-MS data of mass value of double protonated molecular ion of novel Microcystin variant for sample of control cultivation in the positive ionization mode. Detector signal intensities (y-Axis) are measured in milli-absorption units (mAU) and counts (dimensionless quantity) for PDA and mass spectrometry data respectively.
Figure 17D:
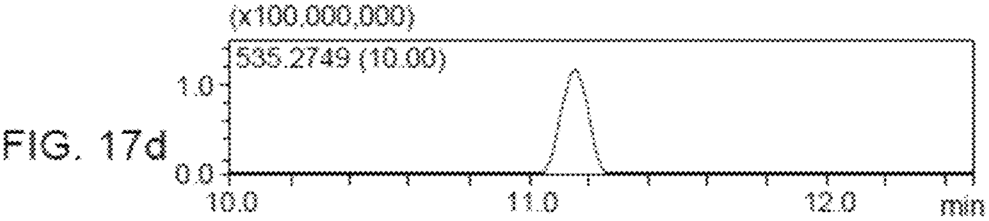
FIG. 17*d*: Exemplary embodiment No. 8: Incorporation of the modified substrate Nitro-Arg (Arg=Arginine) into Microcystin (D-Asp3, E-Dhb7)-RR in position 2/4 produced by strain CBT 329. Extracted ion chromatogram from HPLC-MS data of mass value of double protonated molecular ion of novel Microcystin variant for sample of cultivation with added modified substrate in the positive ionization mode. Detector signal intensities (y-Axis) are measured in milli-absorption units (mAU) and counts (dimensionless quantity) for PDA and mass spectrometry data respectively.
Figure 17E:
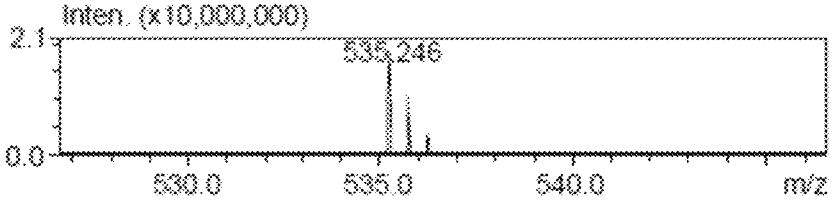
FIG. 17*e*: Exemplary embodiment No. 8: Incorporation of the modified substrate Nitro-Arg (Arg=Arginine) into Microcystin (D-Asp3, E-Dhb7)-RR in position 2/4 produced by strain CBT 329. (e) shows the averaged mass spectrum of the peak visible in chromatogram (d).
Figure 18:
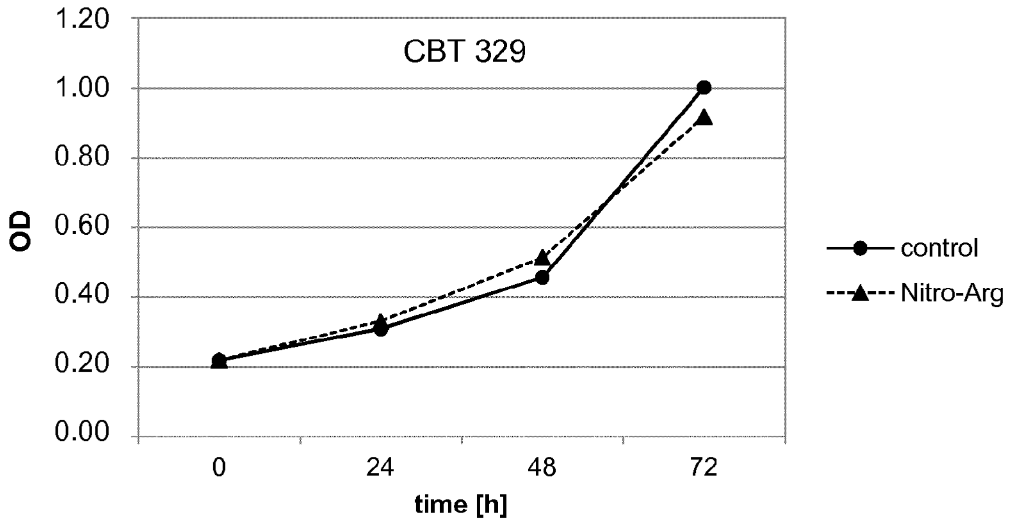
FIG. 18: Exemplary embodiment No. 8: Growths curve of CBT 329 cultures with and without Nitro-Arg (Arg=Arginine) added.
Figure 19A:
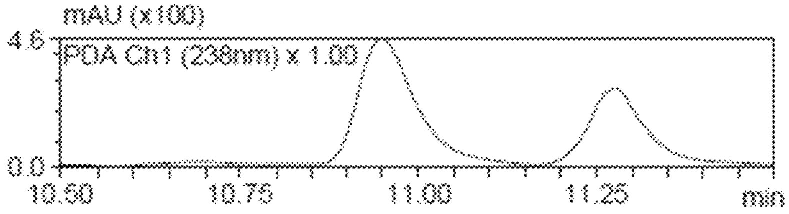
FIG. 19*a*: Exemplary embodiment No. 9: Incorporation of the modified substrate Azido-Lys (Lys=Lysine) into Microcystin YR in position 4 produced by strain CBT 1. HPLC-PDA Chromatogram at 238 nm for sample of control cultivation. Detector signal intensities (y-Axis) are measured in milli-absorption units (mAU) and counts (dimensionless quantity) for PDA and mass spectrometry data respectively.
Figure 19B:
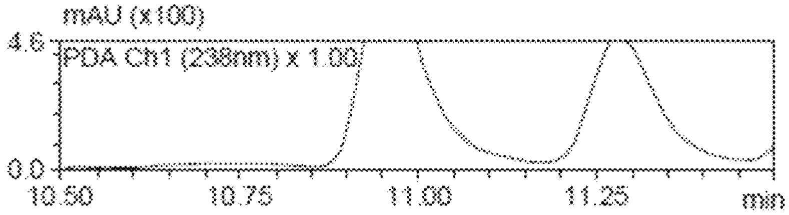
FIG. 19*b*: Exemplary embodiment No. 9: Incorporation of the modified substrate Azido-Lys (Lys=Lysine) into Microcystin YR in position 4 produced by strain CBT 1. HPLC-PDA Chromatogram at 238 nm for sample of cultivation with added modified substrate. Detector signal intensities (y-Axis) are measured in milli-absorption units (mAU) and counts (dimensionless quantity) for PDA and mass spectrometry data respectively. The PDA-Signal of the novel Azido-Lys (Lys=Lysine) variant of Microcystin YR is not visible due to overlapping peaks in the sample.
Figure 19C:
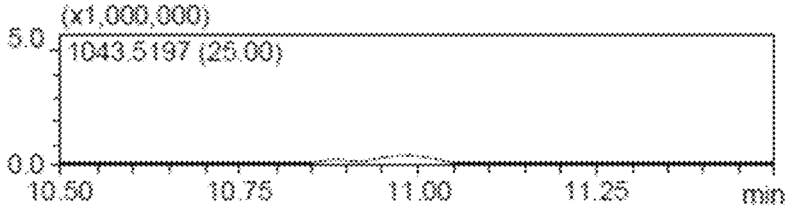
FIG. 19*c*: Exemplary embodiment No. 9: Incorporation of the modified substrate Azido-Lys (Lys=Lysine) into Microcystin YR in position 4 produced by strain CBT 1. Extracted ion chromatogram from HPLC-MS data of mass value of protonated molecular ion of novel Microcystin variant for sample of control cultivation in the positive ionization mode. Detector signal intensities (y-Axis) are measured in milli-absorption units (mAU) and counts (dimensionless quantity) for PDA and mass spectrometry data respectively.
Figure 19D:
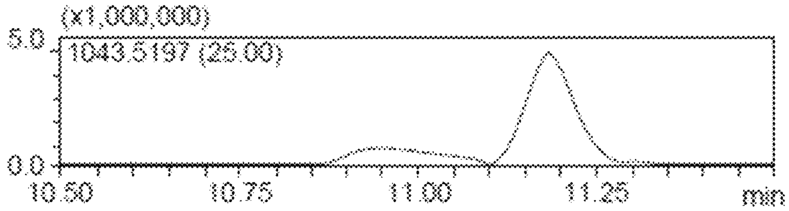
FIG. 19*d*: Exemplary embodiment No. 9: Incorporation of the modified substrate Azido-Lys (Lys=Lysine) into Microcystin YR in position 4 produced by strain CBT 1. Extracted ion chromatogram from HPLC-MS data of mass value of protonated molecular ion of novel Microcystin variant for sample of cultivation with added modified substrate in the positive ionization mode. Detector signal intensities (y-Axis) are measured in milli-absorption units (mAU) and counts (dimensionless quantity) for PDA and mass spectrometry data respectively. The PDA-Signal of the novel Azido-Lys (Lys=Lysine) variant of Microcystin YR is not visible due to overlapping peaks in the sample.
Figure 19E:
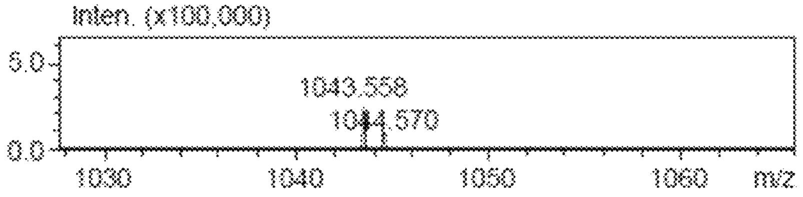
FIG. 19*e*: Exemplary embodiment No. 9: Incorporation of the modified substrate Azido-Lys (Lys=Lysine) into Microcystin YR in position 4 produced by strain CBT 1. (e) shows the averaged mass spectrum of the peak visible in chromatogram (d). The PDA-Signal of the novel Azido-Lys (Lys=Lysine) variant of Microcystin YR is not visible due to overlapping peaks in the sample.
Figure 20:
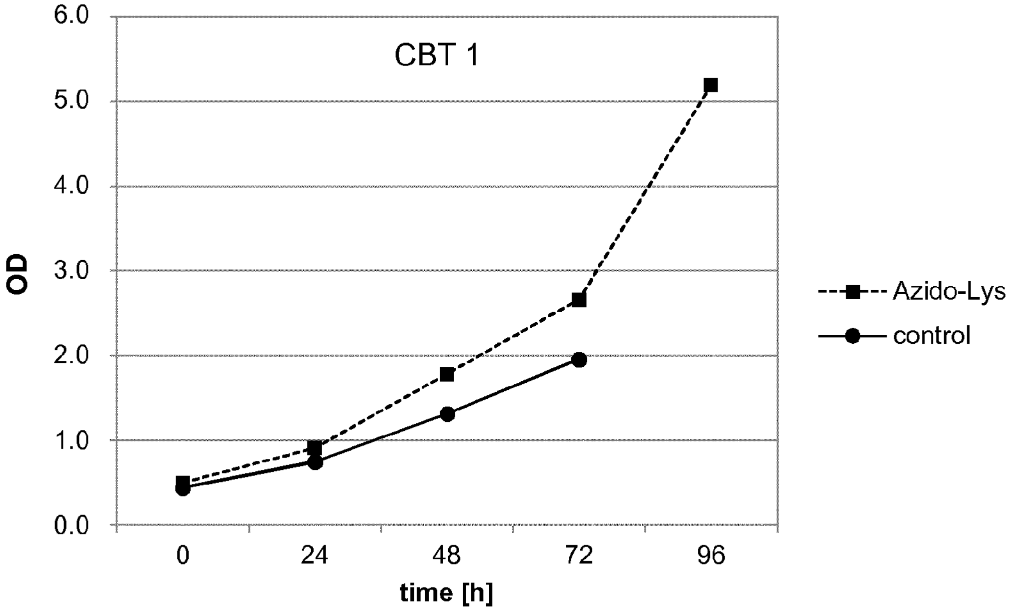
FIG. 20: Exemplary embodiment No. 9: Growths curve of CBT 1 cultures with and without Azido-Lys (Lys=Lysine) added.
Figure 21A:
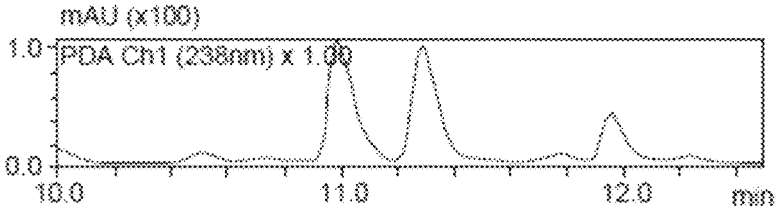
FIG. 21*a*: Exemplary embodiment No. 10: Incorporation of the modified substrate Azido-Norval (Norval=Norvaline) into Microcystin RR in position 2 produced by strain CBT 633. HPLC-PDA Chromatogram at 238 nm for sample of control cultivation. Detector signal intensities (y-Axis) are measured in milli-absorption units (mAU) and counts (dimensionless quantity) for PDA and mass spectrometry data respectively.
Figure 21B:
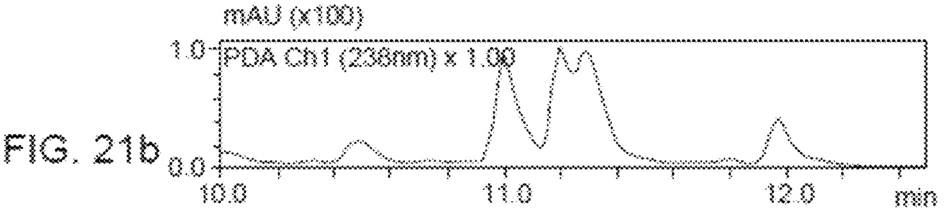
FIG. 21*b*: Exemplary embodiment No. 10: Incorporation of the modified substrate Azido-Norval (Norval=Norvaline) into Microcystin RR in position 2 produced by strain CBT 633. HPLC-PDA Chromatogram at 238 nm for sample of cultivation with added modified substrate. Detector signal intensities (y-Axis) are measured in milli-absorption units (mAU) and counts (dimensionless quantity) for PDA and mass spectrometry data respectively.
Figure 21C:
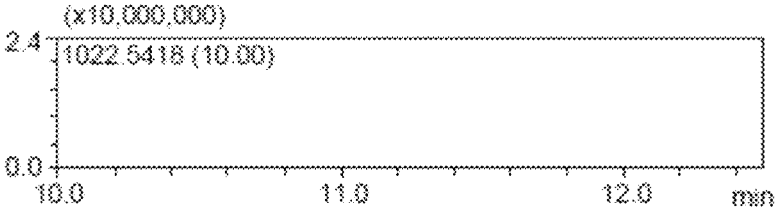
FIG. 21*c*: Exemplary embodiment No. 10: Incorporation of the modified substrate Azido-Norval (Norval=Norvaline) into Microcystin RR in position 2 produced by strain CBT 633. Extracted ion chromatogram from HPLC-MS data of mass value of protonated molecular ion of novel Microcystin variant for sample of control cultivation in the positive ionization mode. Detector signal intensities (y-Axis) are measured in milli-absorption units (mAU) and counts (dimensionless quantity) for PDA and mass spectrometry data respectively.
Figure 21D:
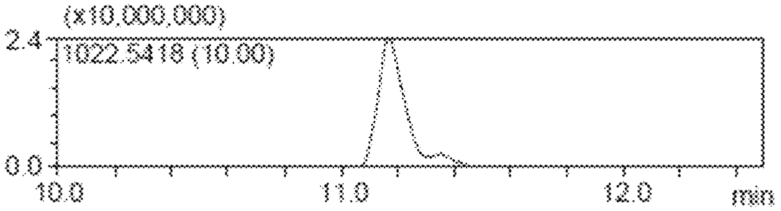
FIG. 21*d*: Exemplary embodiment No. 10: Incorporation of the modified substrate Azido-Norval (Norval=Norvaline) into Microcystin RR in position 2 produced by strain CBT 633. Extracted ion chromatogram from HPLC-MS data of mass value of protonated molecular ion of novel Microcystin variant for sample of cultivation with added modified substrate in the positive ionization mode. Detector signal intensities (y-Axis) are measured in milli-absorption units (mAU) and counts (dimensionless quantity) for PDA and mass spectrometry data respectively.
Figure 21E:
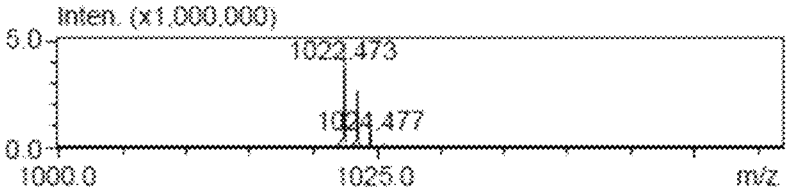
FIG. 21*e*: Exemplary embodiment No. 10: Incorporation of the modified substrate Azido-Norval (Norval=Norvaline) into Microcystin RR in position 2 produced by strain CBT 633. (e) shows the averaged mass spectrum of the peak visible in chromatogram (d).
Figure 22:
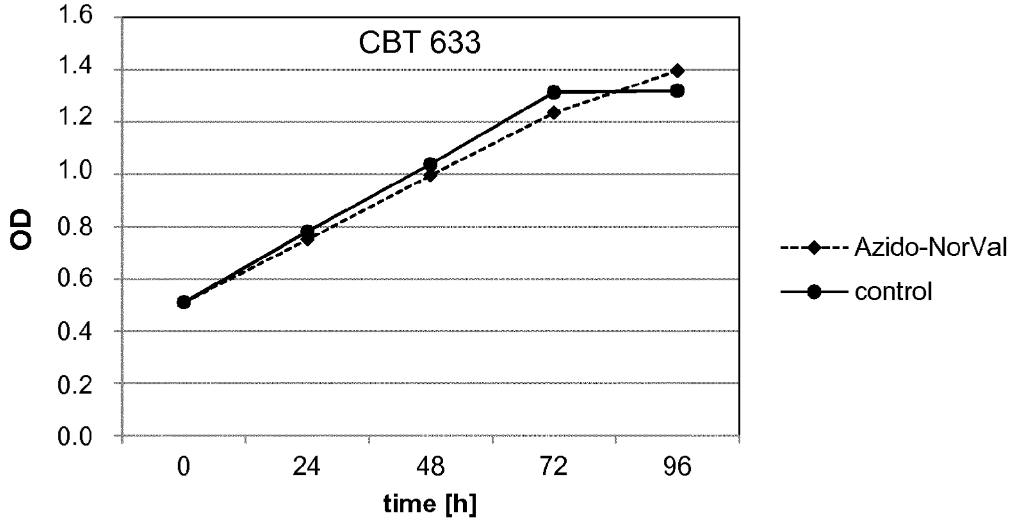
FIG. 22: Growths curve of CBT 633 cultures with and without Azido-Norval (Norval=Norvaline) added.
Figure 23A:
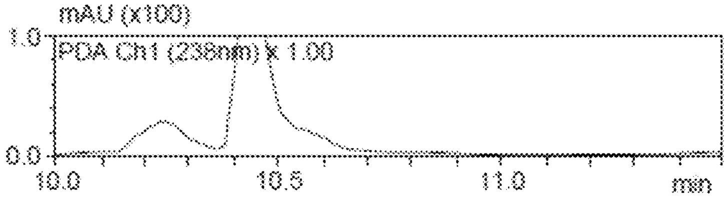
FIG. 23*a*: Exemplary embodiment No. 11: Incorporation of the modified substrate H-homoarg-OH (homoarg=homoarginine) into Nodularin in position 2 produced by strain CBT 786. HPLC-PDA Chromatogram at 238 nm for sample of control cultivation. Detector signal intensities (y-Axis) are measured in milli-absorption units (mAU) and counts (dimensionless quantity) for PDA and mass spectrometry data respectively.
Figure 23B:
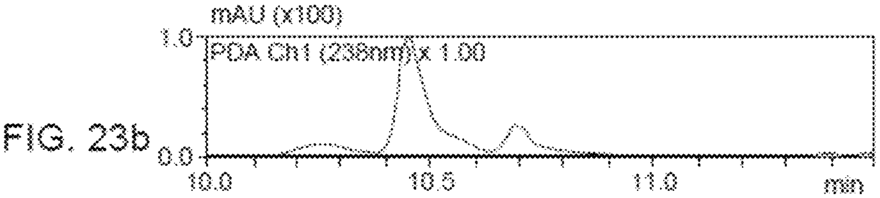
FIG. 23*b*: Exemplary embodiment No. 11: Incorporation of the modified substrate H-homoarg-OH (homoarg=homoarginine) into Nodularin in position 2 produced by strain CBT 786. HPLC-PDA Chromatogram at 238 nm for sample of cultivation with added modified substrate. Detector signal intensities (y-Axis) are measured in milli-absorption units (mAU) and counts (dimensionless quantity) for PDA and mass spectrometry data respectively.
Figure 23C:
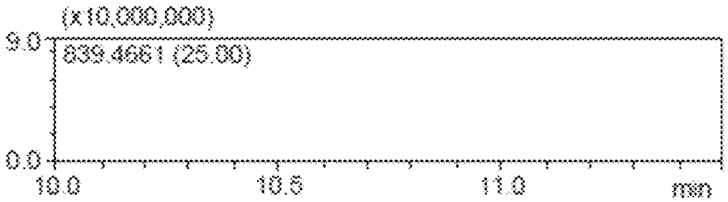
FIG. 23*c*: Exemplary embodiment No. 11: Incorporation of the modified substrate H-homoarg-OH (homoarg=homoarginine) into Nodularin in position 2 produced by strain CBT 786. Extracted ion chromatogram from HPLC-MS data of mass value of protonated molecular ion of novel Nodularin variant for sample of control cultivation in the positive ionization mode. Detector signal intensities (y-Axis) are measured in milli-absorption units (mAU) and counts (dimensionless quantity) for PDA and mass spectrometry data respectively.
Figure 23D:
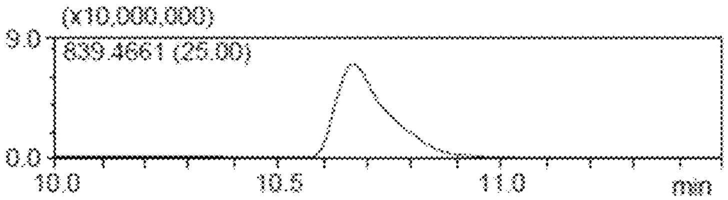
FIG. 23*d*: Exemplary embodiment No. 11: Incorporation of the modified substrate H-homoarg-OH (homoarg=homoarginine) into Nodularin in position 2 produced by strain CBT 786. Extracted ion chromatogram from HPLC-MS data of mass value of protonated molecular ion of novel Nodularin variant for sample of cultivation with added modified substrate in the positive ionization mode. Detector signal intensities (y-Axis) are measured in milli-absorption units (mAU) and counts (dimensionless quantity) for PDA and mass spectrometry data respectively.
Figure 23E:
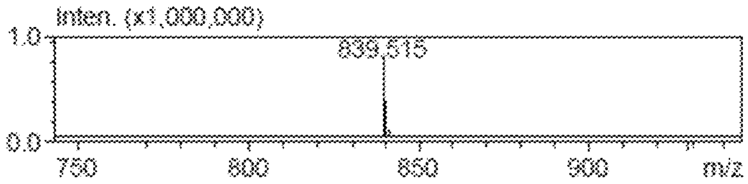
FIG. 23*e*: Exemplary embodiment No. 11: Incorporation of the modified substrate H-homoarg-OH (homoarg=homoarginine) into Nodularin in position 2 produced by strain CBT 786. (e) shows the averaged mass spectrum of the peak visible in chromatogram (d).
Figure 24A:
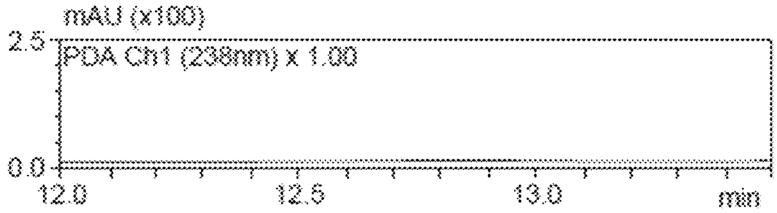
FIG. 24*a*: Exemplary embodiment No. 12: Incorporation of the modified substrate Azido-L-Phe (Phe=phenylalanine) into Microcystin YR in position 2 produced by strain CBT 480 in a large scale (2 l) cultivation system. HPLC-PDA Chromatogram at 238 nm for sample of control cultivation. Detector signal intensities (y-Axis) are measured in milli-absorption units (mAU) and counts (dimensionless quantity) for PDA and mass spectrometry data respectively.
Figure 24B:
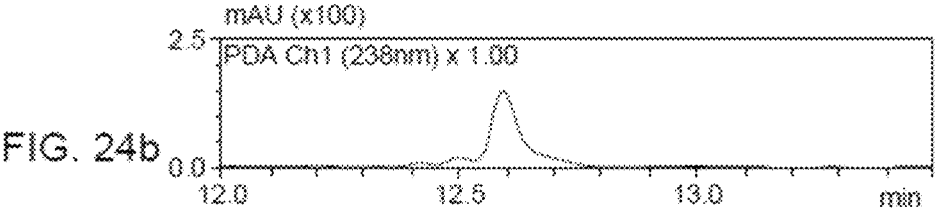
FIG. 24*b*: Exemplary embodiment No. 12: Incorporation of the modified substrate Azido-L-Phe (Phe=phenylalanine) into Microcystin YR in position 2 produced by strain CBT 480 in a large scale (2 l) cultivation system. HPLC-PDA Chromatogram at 238 nm for sample of cultivation with added modified substrate. Detector signal intensities (y-Axis) are measured in milli-absorption units (mAU) and counts (dimensionless quantity) for PDA and mass spectrometry data respectively.
Figure 24C:
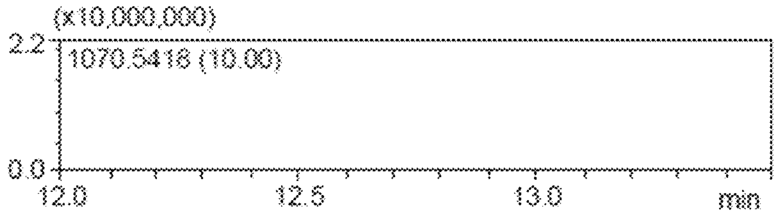
FIG. 24*c*: Exemplary embodiment No. 12: Incorporation of the modified substrate Azido-L-Phe (Phe=phenylalanine) into Microcystin YR in position 2 produced by strain CBT 480 in a large scale (2 l) cultivation system. Extracted ion chromatogram from HPLC-MS data of mass value of protonated molecular ion of novel Microcystin variant for sample of control cultivation in the positive ionization mode. Detector signal intensities (y-Axis) are measured in milli-absorption units (mAU) and counts (dimensionless quantity) for PDA and mass spectrometry data respectively.
Figure 24D:
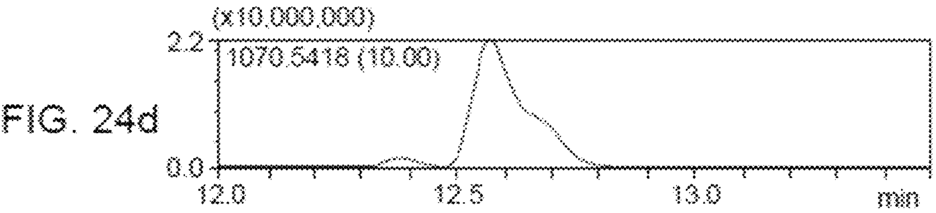
FIG. 24*d*: Exemplary embodiment No. 12: Incorporation of the modified substrate Azido-L-Phe (Phe=phenylalanine) into Microcystin YR in position 2 produced by strain CBT 480 in a large scale (2 l) cultivation system. Extracted ion chromatogram from HPLC-MS data of mass value of protonated molecular ion of novel Microcystin variant for sample of cultivation with added modified substrate in the positive ionization mode. Detector signal intensities (y-Axis) are measured in milli-absorption units (mAU) and counts (dimensionless quantity) for PDA and mass spectrometry data respectively.
Figure 24E:
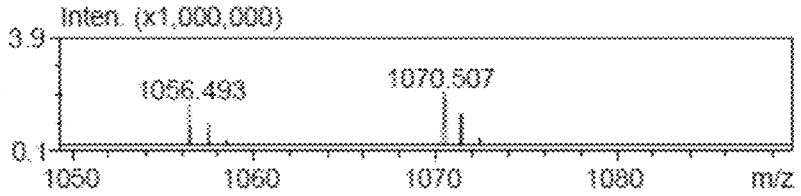
FIG. 24*e*: Exemplary embodiment No. 12: Incorporation of the modified substrate Azido-L-Phe (Phe=phenylalanine) into Microcystin YR in position 2 produced by strain CBT 480 in a large scale (2 I) cultivation system. (e) shows the averaged mass spectrum of the peak visible in chromatogram (d).

BMPR1B (bone morphogenetic protein receptor-type IB, Genbank accession no. NM-001203);

E16 (LAT1, SLC7A5, Genbank accession no. NM-003486);

STEAP1 (six transmembrane epithelial antigen of prostate, Genbank accession no. NM-012449);

0772P (CA125, MUC16, Genbank accession no. AF361486);

MPF (MPF, MSLN, SMR, megakaryocyte potentiating factor, mesothelin, Genbank accession no. NM-005823);

Napi3b (NAPI-3B, NPTIIb, SLC34A2, solute carrier family 34 (sodium phosphate), member 2, type II sodium-dependent phosphate transporter 3b, Genbank accession no. NM-006424);

Sema 5b (F1110372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B, Genbank accession no. AB040878);

PSCA hlg (2700050C12Rik, C530008O16Rik, RIKEN cDNA 2700050C12, RIKEN cDNA 2700050C12 gene, Genbank accession no. AY358628);

ETBR (Endothelin type B receptor, Genbank accession no. AY275463);

MSG783 (RNF124, hypothetical protein F1120315, Genbank accession no. NM-017763);

STEAP2 (HGNC-8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138);

TrpM4 (BR22450, F1120041, TRPM4, TRPM4B, transient receptor potential cation channel, subfamily M, member 4, Genbank accession no. NM-017636);

CRIPTO (CR, CR1, CRGF, CRIPTO, TDGF1, teratocarcinoma-derived growth factor, Genbank accession no. NP-003203 or NM-003212);

CD21 (CR2 (Complement receptor 2) or C3DR(C3d/Epstein Barr virus receptor) or Hs.73792 Genbank accession no. M26004);

CD79b (CD79B, CD79β, IGb (immunoglobulin-associated beta), B29, Genbank accession no. NM-000626 or 11038674);

FcRH2 (IFGP4, IRTA4, SPAP1A (SH2 domain containing phosphatase anchor protein 1a), SPAP1B, SPAP1C, Genbank accession no. NM-030764, AY358130);

HER2 (ErbB2, Genbank accession no. M11730); Coussens L., et al Science (1985) 230(4730):1132-1139);

NCA (CEACAM6, Genbank accession no. M18728); Barnett T., et al Genomics 3, 59-66, 1988;

MDP (DPEP1, Genbank accession no. BC017023);

IL20Rα (IL20Ra, ZCYTOR7, Genbank accession no. AF184971);

Brevican (BCAN, BEHAB, Genbank accession no. AF229053);

EphB2R (DRT, ERK, HekS, EPHT3, Tyro5, Genbank accession no. NM-004442);

ASLG659 (B7h, Genbank accession no. AX092328); US20040101899 (claim 2);

PSCA (Prostate stem cell antigen precursor, Genbank accession no. AJ297436);

GEDA (Genbank accession No. AY260763); AAP14954 lipoma HMGIC fusion-partner-like protein/pid=AAP14954.1 *Homo sapiens* (human);

(26) BAFF-R (B cell-activating factor receptor, BLyS receptor 3, BR3, Genbank accession No. AF116456); BAFF receptor/pid=NP-443177.1-*Homo sapiens*; Thompson, J. S., et al Science 293 (5537), 2108-2111 (2001); WO2004058309; WO2004011611; WO2003045422 (Example; Page 32-33); WO2003014294 (claim 35; FIG. 6B); WO2003035846 (claim 70; Page 615-616); WO200294852 (Col 136-137); WO200238766 (claim 3; Page 133); WO200224909 (Example 3; FIG. 3); Cross-references: MIM:606269; NP-443177.1; NM-052945-1; AF132600

CD22 (B-cell receptor CD22-B isoform, BL-CAM, Lyb-8, Lyb8, SIGLEC-2, FLJ22814, Genbank accession No. AK026467);

CD79a (CD79A, CD79a, immunoglobulin-associated alpha, a B cell-specific protein that covalently interacts with Ig beta (CD79B) and forms a complex on the surface with Ig M molecules, transduces a signal involved in B-cell differentiation);

CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia);

HLA-DOB (Beta subunit of MHC class II molecule (Ia antigen) that binds peptides and presents them to CD4+T lymphocytes);

P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability);

CD72 (B-cell differentiation antigen CD72, Lyb-2); 359 aa), pI: 8.66, MW: 40225 TM: 1 [P] Gene Chromosome: 9p13.3, Genbank accession No. NP-001773.1);

LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis);

FcRH1 (Fc receptor-like protein 1, a putative receptor for the immunoglobulin Fc domain that contains C2 type Ig-like and ITAM domains, may have a role in B-lymphocyte differentiation);

IRTA2 (FcRH5, Immunoglobulin superfamily receptor translocation associated 2, a putative immunoreceptor with possible roles in B cell development and lymphomagenesis;

TENB2 (TMEFF2, tomoregulin, TPEF, HPP1, TR, putative transmembrane proteoglycan, related to the EGF/heregulin family of growth factors and follistatin);

MUC1 (Tumor-associated MUC1 glycopeptide epitopes); Human adenocarcinomas overexpress a hypoglycosylated, tumor-associated form of the mucin-like glycoprotein MUC1 containing abnormal mono- and disaccharide antigens, such as Tn, sialyl-Tn, and TF, as well as stretches of unglycosylated protein backbone in the variable number of tandem repeats (VNTR) region.

The ADC which can be produced based on the present invention may be used to treat various diseases or disorders in a patient, such as cancer and autoimmune conditions including those characterized by the overexpression of a disease-associated antigen, including but not limited to tumor-associated antigen. Exemplary conditions or disorders include infection diseases, thrombosis and others and specifically benign or malignant tumors; leukemia and lymphoid malignancies; other disorders such as neuronal, glial, astrocytal, hypothalamic, glandular, macrophagal, epithelial, stromal, blastocoelic, inflammatory, angiogenic and immunologic disorders. Cancer types susceptible to ADC treatment include those which are characterized by the overexpression of certain tumor associated antigens or cell surface receptors, e.g. HER2.

One method is for the treatment of cancer in a mammal, wherein the cancer is characterized by the overexpression of an ErbB receptor. The mammal optionally does not respond, or responds poorly, to treatment with an unconjugated anti-ErbB antibody. The method comprises administering to the mammal a therapeutically effective amount of an antibody-drug conjugate compound. The growth of tumor cells that overexpress a growth factor receptor such as HER2 receptor or EGF receptor may be inhibited by administering to a patient an ADC according to the invention which binds specifically to said growth factor receptor and a chemotherapeutic agent wherein said antibody-drug conjugate and said chemotherapeutic agent are each administered in amounts effective to inhibit growth of tumor cells in the patient (see FIG. 34).

Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, gastrointestinal stromal tumor (GIST), pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

EXAMPLES

Successful feedings of modified substrates were performed in different cultivation systems and scales allowing for screening (small scales of up to 10 ml; see FIG. 2 A-D) and for production (2-20 L scales; see FIG. 24, 25) of modified non-ribosomal peptides. The different screening scales comprise:

1.6 ml cultures cultivated in ca. 2.2 ml deep-well microtiter plates (dw-MTP) whereas $CO_2$ supply was assured by intense shaking of 600 rpm and a constant $CO_2$ concentration of 5% in the head space above the dw-MTP. Illumination occurred via LED panel or vial fluorescence bulbs for 24 hours a day. Light intensity was adjusted in dependence of the strain and its growth phase between 35-250 μmol/s*$m^2$. The temperature was strain-specific varied between 20° C. and 30° C.

A cultivation according to the method is thus preferred wherein the shaking is between 400-800 rpm and a constant $CO_2$ concentration of 1 to 10% in the head space, preferably 3 to 8% in the head space.

10 ml cultures cultivated in 40 ml polystyrene tubes whereas $CO_2$ supply was assured by intense shaking of 250-350 rpm and a constant $CO_2$ concentration of 5% below the culture vessel. Hereby $CO_2$ got introduced into the culture via a $CO_2$ permeable polypropylene membrane on the bottom of the culture vessels. Illumination occurred via fluorescence bulbs for 24 hours a day and light intensity was again adjusted in dependence of the strain and its growth phase between 35-250 μmol/s*$m^2$. The temperature was again strain-specific varied between 20° C. and 30° C.

A cultivation according to the method is thus preferred wherein the illumination occurred via fluorescence bulbs for 24 hours a day and is between 20-450 μmol/s*m2.

50 ml cultures cultivated in glass flasks whereas $CO_2$ supply was assured by bubbling with constant $CO_2$ concentration of 5%. The cultures were mixed via stirring with a magnetic stir bar at 100 rpm. Illumination occurred via fluorescence bulbs for 24 hours a day and intensity was adjusted in dependence of strain and growth phase between 35-250 μmol/s*m2.

In addition, feeding experiments were also performed in a production scale between 2 L and 20 L whereas $CO_2$ supply and mixing was assured by bubbling with constant $CO_2$ concentration of 0.5-5.0%. Illumination occurred via fluorescence bulbs and intensity was adjusted in dependence of strain and growth phase between 35-250 μmol/s*m2

Optionally, the cultivations were performed under day-night-cycles of 16 hours light/8 hours at the same light intensities during the day period as described above.

Optionally, the cultivations were performed with different light sources (e.g. LED lights or sulfur-plasma lamps) and using strain-specific variations of light intensity, $CO_2$ concentration, shaking/stirring intensity and media composition.

Exemplary feeding scheme for the 10 ml scale:

All strains were cultivated in BG11 medium (see below), according to strain-specific cultivation conditions determined before.

Cells were pre-cultivated in Erlenmeyer flasks under low light conditions (30 μmol/s*m2) for 4 days at 25° C. and on a shaker at 70 rpm.

For the feeding experiment in the 10 ml scale, the cells were inoculated at optical density at 750 nm (0D750 nm) of 0.5 in ca. 40 ml polystyrene tubes. The medium was buffered by addition of TES to a concentration of 10 mM in the medium. Optionally DMSO was added to a concentration of 1% in the medium.

The feeding of cultures started at inoculation by adding the respective modified substrate(s) to a concentration of 10 µM in the medium. Daily additions of modified substrates remained constant over 4 days by feeding of additional 10 µM per day (day 1-4). Alternatively, additions of modified substrate(s) were done on day one and day three after inoculation by feeding of the modified substrate(s) to a concentration of 30 µM in the medium at each of the days. Growth of cultures was monitored daily by measurements of optical density at 750 nm (0D750 nm). Cultivation was finished by adding methanol to the culture to an end concentration of 20%. Subsequently extraction was done via a standard solid phase extraction procedure using C18-modified silica cartridges.

For other scales mentioned above the protocols were similar and only slightly varied. For example, at 2 and 20 L scale the medium was not always buffered and due to the slower growth rate the duration of cultivation was prolonged for another week. Furthermore, in some cases increased amounts of added modified substrates up to 300 µM media concentration were used (if strain tolerated such concentrations) in order to increase the yield of modified non-ribosomal peptides.

TABLE

Recipe for BG11 medium which has been used for feeding experiments

| Component | mg/L | mM |
|---|---|---|
| $NaNO_3$ | 1500 | 17.6 |
| $K_2HPO_4*3H_2O$ | 40 | 0.23 |
| $MgSO_4*7H_2O$ | 75 | 0.3 |
| $CaCl_2*2H_2O$ | 36 | 0.24 |
| $Na_2CO_3$ | 20 | 0.19 |
| Ferric ammon. citrate | 6 | 0.021 |
| Citric acid | 6 | 0.031 |
| $Na_2EDTA*2H_2O$ | 1 | 0.0027 |
| **Trace elements** | **µg/L** | **µM** |
| $H_3BO_3$ | 2.86 | 46.3 |
| $MnCl_2•4H_2O$ | 1.8 | 9.15 |
| $ZnSO_4•7H_2O$ | 0.22 | 0.77 |
| $Na_2MoO_4•2H_2O$ | 0.390 | 1.61 |
| $CuSO_4•5H_2O$ | 0.079 | 0.32 |
| $Co(NO_3)_2•6H_2O$ | 0.0494 | 0.17 |

For the following strains feeding of at least one modified and clickable substrate were demonstrated.

| Cyano Biotech Strain ID No. | Genera | Main non-ribosomal peptide variants produced |
|---|---|---|
| 1 | *Microcystis* | MC-YR |
| 265 | *Microcystis* | MC-LR<br>MC-LR, Cyanopeptolin A, B, C, D und 963A;<br>Microcyclamide, Aeruginosin, Aerucyclamide A, B, C, D |
| 275 | *Microcystis* | MC-LR<br>MC-LW<br>MC-LF |
| 280 | *Planktothrix* | MC-LR |
| 329 | *Planktothrix* | (D-Asp3, Dhb7)MC-RR |
| 332 | *Planktothrix* | (D-Asp3, Dhb7)MC-RR,<br>Anabaenopeptin A,<br>B, E/F, NZ867 |
| 480 | *Microcystis* | MC-LR<br>MC-YR |
| 633 | *Microcystis* | MC-RR |
| 786 | *Nodularia* | NOD |
| 861 | *Microcystis* | MC-RY<br>MC-LY |
| 959 | *Microcystis* | MC-LR<br>MC-YR |
| 1161 | *Planktothrix* | (D-Asp3, E-Dhb7)MC-RR<br>Anabaenopeptin A, E/F, B<br>Oscillamide Y |

MC is microcystin, the two letters behind MC define the amino acids at the variable positions 2 and 4 whereas R is arginine, Y is tyrosine, L is leucine, W is tryptophan, and F ist phenylalanine. D-MAsp3 is D-erythro-β-methylaspartic acid at position 3 and Dhb7 is dehydrobutyrate at position 7. NOD is Nodularin.

FIGS. 4-30 illustrate incorporations of modified amino acids into non-ribosomal peptides, more specific into microcystins, nodularins, anabaenopeptins and oscillamides at different positions and produced by different genera and strains, resp. which carry clickable anchor groups or anchor groups that are easily accessible to additional modification towards conjugable anchor groups.

The following tables summarize results of feeding experiments of different cyanobacterial genera and strains, resp. with one or two modified substrates each comprising an anchor group directly accessible or transformable for use in conjugation chemistry (incl. click chemistry), for the attachment of a targeting moiety and/or a label via a linker or w/o a linker between the modified amino acid and the targeting moiety and/or a label.

TABLE 1

Part 1 of summary of results of feeding one modified substrate to different cyanobacterial strains of the genera *Microcystis* and *Planktothrix*. MC - microcystin with letters behind MC indicating the amino acids at the variable position 2 and 4 in the one-letter-code.

| CBT strain no. | Genera/ Species | NRP variants naturally produced by the strain | Naturally produced NRP variant which is effected by fed modified substrate | Sum formula of naturally produced NRP variant | Monoisotopic mass of naturally produced NRP variant | Naturally incorporated amino acid which is replaced by modified substrate | Sum formula (zwitterion) of natural substrate | Monoisotopic Mass (Zwitterion) of natural substrate |
|---|---|---|---|---|---|---|---|---|
| 1 | *Microcystis* sp. | MC-LR<br>MC-YR | MC-YR | C52H72N10O13 | 1044.52803 | Arg | C6H14N4O2 | 174.111679 |
| 1 | *Microcystis* sp. | MC-LR<br>MC-YR | MC-YR | C52H72N10O13 | 1044.52803 | Tyr | C9H11NO3 | 181.073898 |
| 1 | *Microcystis* sp. | MC-LR<br>MC-YR | MC-YR | C52H72N10O13 | 1044.52803 | Arg | C6H14N4O2 | 174.111679 |

TABLE 1-continued

Part 1 of summary of results of feeding one modified substrate to different cyanobacterial strains of the genera *Microcystis* and *Planktothrix*. MC - microcystin with letters behind MC indicating the amino acids at the variable position 2 and 4 in the one-letter-code.

| | | | | | | | | |
|---|---|---|---|---|---|---|---|---|
| 1 | *Microcystis* sp. | MC-LR MC-YR | MC-YR | C52H72N10O13 | 1044.52803 | Tyr | C9H11NO3 | 181.073898 |
| 265 | *Microcystis aeruginosa* | MC-LR, Cyanopeptolin A, B, C, D und 963A; Microcyclamide, Aeruginosin, Aerucyclamide, A, B, C, D | MC-LR | C49H74N10O12 | 994.548767 | Arg | C6H14N4O2 | 174.111679 |
| 265 | *Microcystis aeruginosa* | MC-LR, Cyanopeptolin A, B, C, D und 963A; Microcyclamide, Aeruginosin, Aerucyclamide, A, B, C, D | MC-LR | C49H74N10O12 | 994.548767 | Leu | C6H13NO2 | 131.094635 |
| 275 | *Microcystis aeruginosa* | MC-LR MC-LW MC-LF | MC-LR | C49H74N10O12 | 994.548767 | Arg | C6H14N4O2 | 174.111679 |
| 275 | *Microcystis aeruginosa* | MC-LR MC-LW MC-LF | MC-LR | C49H74N10O12 | 994.548767 | Arg | C6H14N4O2 | 174.111679 |
| 275 | *Microcystis aeruginosa* | MC-LR MC-LW MC-LF | MC-LR | C49H74N10O12 | 994.548767 | Arg | C6H14N4O2 | 174.111679 |
| 275 | *Microcystis aeruginosa* | MC-LR MC-LW MC-LF | MC-LF | C52H71N7O12 | 985.516071 | Phe | C9H11NO2 | 165.078979 |
| 275 | *Microcystis aeruginosa* | MC-LR MC-LW MC-LF | MC-LF | C52H71N7O12 | 985.516071 | Phe | C9H11NO2 | 165.078979 |
| 275 | *Microcystis aeruginosa* | MC-LR MC-LW MC-LF | MC-LR | C49H74N10O12 | 994.548767 | Arg | C6H14N4O2 | 174.111679 |
| 275 | *Microcystis aeruginosa* | MC-LR MC-LW MC-LF | MC-LR | C49H74N10O12 | 994.548767 | Arg | C6H14N4O2 | 174.111679 |
| 275 | *Microcystis aeruginosa* | MC-LR MC-LW MC-LF | MC-LW | C54H72N8O12 | 1024.52697 | Trp | C11H12N2O2 | 204.089878 |
| 275 | *Microcystis aeruginosa* | MC-LR MC-LW MC-LF | MC-LW | C54H72N8O12 | 1024.52697 | Trp | C11H12N2O2 | 204.089878 |

| CBT strain no. | Position of naturally incorporated amino acid in NRP | Short name of modified substrate | Sum formula (zwitterion) of modified substrate | Monoisotopic mass (zwitterion) of modified substrate | Mass difference between natural und modified substrate (Da) | Calculated monoisotopic mass of mutasynthesis product (novel microcystin) | Measured monoisotopic mass of mutasynthesis product [M + H]+ | MS Peak EIC (Mass spectrometry) | UV Peak PDA (HPLC) |
|---|---|---|---|---|---|---|---|---|---|
| 1 | 2 | Azido-Lys | C6H12N4O2 | 172.0960 | 2.0157 | 1042.5124 | 1043.5197 | yes | yes |
| 1 | 4 | Prg-Tyr | C12H13NO3 | 219.0895 | −38.0156 | 1082.5437 | 1083.5510 | yes | yes |
| 1 | 2 | Nitro-Arg | C6H13N5O4 | 219.0968 | −44.9851 | 1089.5131 | 1090.5204 | yes | yes |
| 1 | 4 | Azido-L-Phe | C9H10N4O2 | 206.0804 | −25.0065 | 1069.5345 | 1070.5418 | yes | yes |
| 265 | 4 | Prg-Tyr | C12H13NO3 | 219.0895 | −44.9779 | 1039.5266 | 1040.5339 | yes | no |
| 265 | 2 | Prg-Tyr | C12H13NO3 | 219.0895 | −87.9949 | 1082.5437 | 1083.5510 | yes | no |
| 275 | 4 | Nitro-Arg | C6H13N5O4 | 219.0968 | −44.9851 | 1039.5338 | 1040.5411 | yes | undetermined |
| 275 | 4 | Furyl-Ala | C7H9NO3 | 155.0582 | 19.0534 | 975.4953 | 976.5026 | yes | undetermined |
| 275 | 4 | Lys(Poc) | C10H16N2O4 | 228.1110 | −53.9993 | 1048.5481 | 1049.5554 | yes | undetermined |
| 275 | 4 | Prg-Tyr | C12H13NO3 | 219.0895 | −54.0106 | 1039.5266 | 1040.5339 | yes | yes |
| 275 | 4 | Azido-L-Phe | C9H10N4O2 | 206.0804 | −41.0014 | 1026.5175 | 1027.5247 | yes | yes |
| 275 | 4 | Azido-Lys | C6H12N4O2 | 172.0960 | 2.0157 | 992.5331 | 993.5404 | yes | yes |
| 275 | 4 | Azido-Norval | C5H10N4O2 | 158.0804 | 16.0313 | 978.5175 | 979.5247 | yes | yes |
| 275 | 4 | Prg-Tyr | C12H13NO3 | 219.0895 | −14.9997 | 1039.5266 | 1040.5339 | yes | yes |
| 275 | 4 | Azido-L-Phe | C9H10N4O2 | 206.0804 | −1.9905 | 1026.5175 | 1027.5247 | yes | yes |

TABLE 2

Part 2 of summary of results of feeding one modified substrate to different cyanobacterial strains of the genera *Microcystis* and *Planktothrix*. MC - microcystin with letters behind MC indicating the amino acids at the variable position 2 and 4 in the one-letter-code.

| CBT strain no. | Genera/ Species | NRP variants naturally produced by the strain | Naturally produced NRP variant which is effected by fed modified substrate | Sum formula of naturally produced NRP variant | Monoiso-topic mass of naturally produced NRP variant | Naturally incorporated amino acid which is replaced by modified substrate | Sum formula (zwit-terion) of natural substrate | Monoiso-topic mass (Zwit-terion) of natural substrate |
|---|---|---|---|---|---|---|---|---|
| 329 | *Planktothrix agardhii* | (D-Asp3, E-Dhb7)MC-RR | (D-Asp3, E-Dhb7)MC-RR | C48H73N13O12 | 1023.5502 | Arg | C6H14N4O2 | 174.11168 |
| 332 | *Planktothrix rubescnes* | Anabaenopeptin A, B, E/Fund NZ857, (D-Asp3, E-Dhb7)MC-RR | (D-Asp3, E-Dhb7)MC-RR | C48H73N13O12 | 1023.5502 | Arg | C6H14N4O2 | 174.11168 |
| 480 | *Microcystis aeruginosa* | MC-LR (D-Asp3)MC-YR | MC-LR | C49H74N10O12 | 994.548767 | Leu | C6H13NO2 | 131.09464 |
| 480 | *Microcystis aeruginosa* | MC-LR (D-Asp3)MC-YR | MC-LR | C49H74N10O12 | 994.548767 | Arg | C6H14N4O2 | 174.11168 |
| 480 | *Microcystis aeruginosa* | MC-LR (D-Asp3)MC-YR | MC-LR | C49H74N10O12 | 994.548767 | Arg | C6H14N4O2 | 174.11168 |
| 480 | *Microcystis aeruginosa* | MC-LR (D-Asp3)MC-YR | MC-YR | C52H72N10O13 | 1044.52803 | Arg | C6H14N4O2 | 174.11168 |
| 480 | *Microcystis aeruginosa* | MC-LR (D-Asp3)MC-YR | MC-YR | C52H72N10O13 | 1044.52803 | Tyr | C9H11NO3 | 181.0739 |
| 480 | *Microcystis aeruginosa* | MC-LR (D-Asp3)MC-YR | MC-YR | C52H72N10O13 | 1044.52803 | Arg | C6H14N4O2 | 174.11168 |
| 480 | *Microcystis aeruginosa* | MC-LR (D-Asp3)MC-YR | MC-YR | C52H72N10O13 | 1044.52803 | Tyr | C9H11NO3 | 181.0739 |
| 480 | *Microcystis aeruginosa* | MC-LR (D-Asp3)MC-YR | MC-YR | C52H72N10O13 | 1044.52803 | Tyr | C9H11NO3 | 181.0739 |
| 480 | *Microcystis aeruginosa* | MC-LR (D-Asp3)MC-YR | MC-LR | C49H74N10O12 | 994.548767 | Leu | C6H13NO2 | 131.09464 |
| 480 | *Microcystis aeruginosa* | MC-LR (D-Asp3)MC-YR | MC-YR | C52H72N10O13 | 1044.52803 | Tyr | C9H11NO3 | 181.0739 |

| CBT strain no. | Position of naturally incor-porated amino acid in NRP | Short name of modified substrate | Sum formula (zwitterion) of modified substrate | Monoiso-topic mass (zwitter-ion) of modified substrate | Mass difference between natural und modified substrate (Da) | Calculated monoiso-topic mass of mutasyn-thesis product (novel NRP) | Measured monoiso-topic mass of mutasyn-thesis product [M + H]+ | MS Peak EIC (Mass spectro-metry) | UV Peak PDA (HPLC) |
|---|---|---|---|---|---|---|---|---|---|
| 329 | 4 | Nitro-Arg | C6H13N5O4 | 219.0968 | −44.9851 | 1068.5353 | 1069.5426 | yes | yes |
| 332 | 2 | Prg-Tyr | C12H13NO3 | 219.0895 | −44.9779 | 1068.5281 | 1069.5353 | yes | yes |
| 480 | 2 | Azido-Norval | C5H10N4O2 | 158.0804 | −26.9857 | 1021.5345 | 1022.5418 | yes | undeter-mined |
| 480 | 4 | Nitro-Arg | C6H13N5O4 | 219.0968 | −44.9851 | 1039.5338 | 1040.5411 | yes | yes |
| 480 | 4 | Azido-Lys | C6H12N4O2 | 172.0960 | 2.0157 | 992.5331 | 993.5404 | yes | yes |
| 480 | 4 | Azido-Lys | C6H12N4O2 | 172.0960 | 2.0157 | 1042.5124 | 1043.5197 | yes | yes |
| 480 | 2 | Prg-Tyr | C12H13NO3 | 219.0895 | −38.0156 | 1082.5437 | 1083.5510 | yes | yes |
| 480 | 4 | Nitro-Arg | C6H13N5O4 | 219.0968 | −44.9851 | 1089.5131 | 1090.5204 | yes | yes |
| 480 | 2 | Azido-L-Phe | C9H10N4O2 | 206.0804 | −25.0065 | 1069.5345 | 1070.5418 | yes | yes |
| 480 | 2 | Prg-Tyr | C12H13NO3 | 219.0895 | −38.0156 | 1082.5437 | 1083.5510 | yes | yes |
| 480 | 2 | Azido-Lys | C6H12N4O2 | 172.0960 | −41.0014 | 1035.5502 | 1036.5574 | yes | yes |
| 480 | 2 | Azido-Lys | C6H12N4O2 | 172.0960 | 8.9779 | 1035.5502 | 1036.5574 | yes | yes |

TABLE 3

Part 3 of summary of results of feeding one modified substrate to different cyanobacterial strains of the genera *Microcystis* and *Planktothrix*. MC - microcystin with letters behind MC indicating the amino acids at the variable position 2 and 4 in the one-letter-code.

| CBT strain no. | Genera/ Species | Microcystin variants naturally produced by the strain | Naturally produced NRP variant which is effected by fed modified substrate | Sum formula of naturally produced NRP variant | Monoiso-topic mass of naturally produced NRP variant | Naturally incorporated amino acid which is replaced by modified substrate | Sum formula (zwit-terion) of natural substrate | Monoiso-topic Mass (Zwit-terion) of natural substrate |
|---|---|---|---|---|---|---|---|---|
| 633 | *Microcystis* sp. | MC-RR | MC-RR | C49H75N13O12 | 1037.5658 | Arg | C6H14N4O2 | 174.11168 |
| 633 | *Microcystis* sp. | MC-RR | MC-RR | C49H75N13O12 | 1037.5658 | Arg | C6H14N4O2 | 174.11168 |
| 633 | *Microcystis* sp. | MC-RR | MC-RR | C49H75N13O12 | 1037.5658 | Arg | C6H14N4O2 | 174.11168 |
| 633 | *Microcystis* sp. | MC-RR | MC-RR | C49H75N13O12 | 1037.5658 | Arg | C6H14N4O2 | 174.11168 |
| 786 | *Nodularia* sp. | NOD(MeAsp1?) | NOD (MeAsp1?) | C41H60N8O10 | 824.44324 | Arg | C7H16N4O2 | 174.11168 |
| 959 | *Microcystis* sp. | MC-LR MC-YR | MC-LR | C49H74N10O12 | 994.548767 | Arg | C6H14N4O2 | 174.11168 |
| 959 | *Microcystis* sp. | MC-LR MC-YR | MC-YR | C52H72N10O13 | 1044.52803 | Arg | C6H14N4O2 | 174.11168 |
| 959 | *Microcystis* sp. | MC-LR MC-YR | MC-LR | C49H74N10O12 | 994.548767 | Arg | C6H14N4O2 | 174.11168 |
| 959 | *Microcystis* sp. | MC-LR MC-YR | MC-YR | C52H72N10O13 | 1044.52803 | Arg | C6H14N4O2 | 174.11168 |
| 959 | *Microcystis* sp. | MC-LR MC-YR | MC-LR | C49H74N10O12 | 994.548767 | Arg | C6H14N4O2 | 174.11168 |
| 959 | *Microcystis* sp. | MC-LR MC-YR | MC-YR | C52H72N10O13 | 1044.52803 | Arg | C6H14N4O2 | 174.11168 |
| 959 | *Microcystis* sp. | MC-LR MC-YR | MC-YR | C52H72N10O13 | 1044.52803 | Tyr | C9H11NO3 | 181.0739 |
| 959 | *Microcystis* sp. | MC-LR MC-YR | MC-YR | C52H72N10O13 | 1044.52803 | Tyr | C9H11NO3 | 181.0739 |
| 1161 | *Planktothrix rubescens* | (D-Asp3, E-Dhb7)MC-RR, Anabaenopeptin A, B, E/F, Oscillamide Y | (D-Asp3, E-Dhb7)MC-RR | C48H73N13O12 | 1023.5502 | Arg | C6H14N4O2 | 174.11168 |
| 861R | *Microcystis aeruginosa* | MC-LY MC-RY | MC-LY | C52H71N7O13 | 1001.51099 | Leu | C6H13NO2 | 131.09464 |
| 861R | *Microcystis aeruginosa* | MC-LY MC-RY | MC-RY | C52H72N10O13 | 1044.52803 | Arg | C6H14N4O2 | 174.11168 |
| 861R | *Microcystis aeruginosa* | MC-LY MC-RY | MC-RY | C52H72N10O13 | 1044.52803 | Tyr | C9H11NO3 | 181.0739 |

| CBT strain no. | Position of naturally incor-porated amino acid in NRP | Short name of modified substrate | Sum formula (zwitterion) of modified substrate | Monoiso-topic mass (zwitter-ion) of modified substrate | Mass difference between natural und modified substrate (Da) | Calculated monoiso-topic mass of mutasyn-thesis product (novel microcystin) | Measured monoiso-topic mass of mutasyn-thesis product [M + H]+ | MS Peak EIC (Mass spectro-metry) | UV Peak PDA (HPLC) |
|---|---|---|---|---|---|---|---|---|---|
| 633 | 2 | Azido-L-Ala | C3H6N4O2 | 130.0491 | 44.0626 | 993.5032 | 994.5105 | yes | yes |
| 633 | 2 | Azido-Norval | C5H10N4O2 | 158.0804 | 16.0313 | 1021.5345 | 1022.5418 | yes | yes |
| 633 | 2 | Nitro-Arg | C6H13N5O4 | 219.0968 | −44.9851 | 1082.5509 | 1083.5582 | yes | yes |
| 633 | 2 | Azido-Lys | C6H12N4O2 | 172.0960 | 2.0157 | 1035.5501 | 1036.5574 | yes | yes |
| 786 | 2 | H-homo-Arg-OH | C7H16N4O2 | 188.1273 | −14.0156 | 838.4589 | 839.4661 | yes | yes |
| 959 | 4 | Nitro-Arg | C6H13N5O4 | 219.0968 | −44.9851 | 1039.5338 | 1040.5411 | yes | undeter-mined |
| 959 | 4 | Nitro-Arg | C6H13N5O4 | 219.0968 | −44.9851 | 1089.5131 | 1090.5204 | yes | undeter-mined |
| 959 | 4 | Azido-L-Ala | C3H6N4O2 | 130.0491 | 44.0626 | 950.4862 | 951.4934 | yes | yes |
| 959 | 4 | Azido-L-Ala | C3H6N4O2 | 130.0491 | 44.0626 | 1000.4654 | 1001.4727 | yes | yes |
| 959 | 4 | Azido-Norval | C5H10N4O2 | 158.0804 | 16.0313 | 978.5175 | 979.5247 | yes | yes |
| 959 | 4 | Azido-Norval | C5H10N4O2 | 158.0804 | 16.0313 | 1028.4967 | 1029.5040 | yes | yes |
| 959 | 2 | Prg-Tyr | C12H13NO3 | 219.0895 | −38.0156 | 1082.5437 | 1083.5510 | yes | yes |
| 959 | 2 | Azido-L-Phe | C9H10N4O2 | 206.0804 | −25.0065 | 1069.5345 | 1070.5418 | yes | yes |
| 1161 | 2 | Prg-Tyr | C12H13NO3 | 219.0895 | −44.9779 | 1068.5281 | 1069.5353 | yes | yes |

TABLE 3-continued

Part 3 of summary of results of feeding one modified substrate to different cyanobacterial strains of the genera *Microcystis* and *Planktothrix*. MC - microcystin with letters behind MC indicating the amino acids at the variable position 2 and 4 in the one-letter-code.

| | | | | | | | | | |
|---|---|---|---|---|---|---|---|---|---|
| 861R | 2 | Azido-Lys | C6H12N4O2 | 172.0960 | −41.0014 | 1042.5124 | 1043.5197 | yes | yes |
| 861R | 2 | Azido-Lys | C6H12N4O2 | 172.0960 | 2.0157 | 1042.5124 | 1043.5197 | yes | yes |
| 861R | 4 | Azido-Lys | C6H12N4O2 | 172.0960 | 8.9779 | 1035.5502 | 1036.5574 | yes | yes |

TABLE 4

Summary of results of feeding two modified substrates to different cyanobacterial culture of the genera *Microcystis*. MC - microcystin with letters behind MC indicating the amino acids at the variable position 2 and 4 in the one-letter-code.

| CBT strain no. | Genera/ Species | Microcystin variants naturally produced by the strain | Monoisotopic mass of naturally produced microcystin variant which is effected by the substrates | Naturally incorporated; amino acid which is replaced by modified substrate 1 (position in MC) | Naturally incorporated amino acid which is replaced by modified substrate 2 (position in MC) | Short names of modified substrate 1 | Monoisotopic mass (zwitterion) of modified substrate 1 | Short names of modified substrate 2 |
|---|---|---|---|---|---|---|---|---|
| 1 | *Microcystis* sp. | MC-YR | 1044.528032 | Tyr (pos. 4) | Arg (pos. 2) | Prg-Tyr | 219.0895433 | Nitro-Arg |
| 1 | *Microcystis* sp. | MC-YR | 1044.528032 | Arg (pos. 2) | Tyr (pos. 4) | Nitro-Arg | 219.0967539 | Azido-L-Phe |
| 480 | *Microcystis aeruginosa* | MC-LR (D-Asp3)MC-YR | 1044.528032 | Arg (pos. 4) | Tyr (pos. 2) | Nitro-Arg | 219.0967539 | Prg-Tyr |
| 480 | *Microcystis aeruginosa* | MC-LR (D-Asp3)MC-YR | 1044.528032 | Arg (pos. 4) | Tyr (pos. 2) | Nitro-Arg | 219.0967539 | Azido-L-Phe |

| CBT strain no. | Monoisotopic mass (zwitterion) of modified substrate 2 | Mass difference between natural und modified substrate 1 (Da) | Mass difference between natural und modified substrate 2 (Da) | Calculated monoisotopic mass of mutasynthesis product (novel microcystin) | Measured monoisotopic mass of mutasynthesis product [M + H]+ | MS Peak EIC (Mass spectrometry) | UV Peak PDA (HPLC) |
|---|---|---|---|---|---|---|---|
| 1 | 219.0967538 | −38.01564528 | −44.885 | 1127.5288 | 1128.3360 | yes | yes |
| 1 | 206.0803756 | −44.08507492 | −25.00647758 | 1114.5196 | 1115.5269 | yes | yes |
| 480 | 219.0899433 | −44.98507492 | −38.03564528 | 1127.5288 | 1128.5360 | yes | yes |
| 480 | 206.0803756 | −44.98507492 | −25.00547758 | 1134.5396 | 3115.5269 | yes | yes |

Figure Captions

FIG. 1:

Upper left: General structure of Microcystins. X2 and Z4 indicate variable L-amino acids. D-Ala=D-Alanine, D-Me-Asp=D-methyl aspartic acid, Arg=Arginine, Adda=3-amino-9-methoxy-2,6,8-trimethyl-10-phenyldeca-4,6-dienoic acid, D-Glu=D-glutamic acid, Mdha=N-methyldehydroalanine. Upper right: General structure of Nodularins. $Arg_2$ indicates the variable L-amino acid corresponding to Z4 in the microcystin molecule. D-Me-Asp=D-methyl aspartic acid, Arg=Arginine, Adda=3-amino-9-methoxy-2,6,8-trimethyl-10-phenyldeca-4,6-dienoic acid, D-Glu=D-glutamic acid, Mdhb=N-methyldehydrobutyrate.

Down right: General structure of anabaenopeptin A and schematic general structure of anabaenopeptin type peptides (incl. oscillamides): Anabaenopeptins (and oscillamides) are cyclic peptides that are characterized by a lysine in position 5 and the formation of the ring by an N-6-peptide bond between Lys and the carboxy group of the amino acid in position 6 A side chain of one amino acid unit is attached to the ring by an ureido bond formed between the a-N of Lys and the a-N of the side chain amino acid. All other positions in the ring and side chain are variable.

Down right: Chemical structure of cryptophycin-1. Cryptophycins are a class of macrocyclic depsipeptides produced as secondary metabolites by cyanobacteria of the genus *Nostoc*. Isolation of the first representative, cryptophycin-1, from cultivated *Nostoc* species ATCC 53789 was published in 1990 by researchers at Merck.

FIG. 2:

Comparison between different cultivation systems and scales and different mass spectrometry detections in the context of suitable screening approaches towards strains that are suited for feeding of modified substrates for modifying non-ribosomal peptides including CA (FIGS. 2 A to 2 D)

FIG. 2 A:

Detection of modified microcystins by two different mass spectrometry method after feeding of modified substrates to a *Microcystis aeruginosa* strain CBT 480 in a 50 ml scale (above of each of the four figures A, B, C, D detection with ESI-IT-ToF-MS; below of each of the four figures A, B, C, D detection with MALDI-ToF-MS).

| | |
|---|---|
| A: Control (no feeding with O-methyltyrosine) | B: Control (no feeding with homoarginine) |
| C: Feeding with O-methyltyrosine | D: Feeding with homoarginine |

Molecule Masses of Naturally Produced Microcystins:

995 Da=MC-LR, 1045 Da=MC-YR

Molecule masses of modified microcystins generated by feeding with O-methyltyrosine (OMetY) and homoarginine (hR)

1059 Da=MC-OMetYR or MC-YhR; 1009 Da=MC-LhR

FIG. 2 B:

Detection of modified microcystins by two different mass spectrometry method after feeding of modified substrates to a *Microcystis aeruginosa* strain CBT 480 in a 6 ml scale (above of each of the two figures A/A' and B/B' detection with ESI-IT-ToF-MS; below of each of the two figures A/A' and B/B' detection with MALDI-ToF-MS).

| | |
|---|---|
| A, A': CBT 480 culture fed with O-methyltyrosine | B, B': CBT 480 culture fed with homoarginine |

Molecule Masses of Naturally Produced Microcystins:

995 Da=MC-LR, 1045 Da=MC-YR

Molecule masses of modified microcystins generated by feeding with O-methyltyrosine (OMetY) and homoarginine (hR)

1059 Da=MC-OMetYR or MC-YhR; 1009 Da=MC-LhR;

FIG. 2 C:

Detection of modified microcystins by two different mass spectrometry method after feeding of modified substrates to a *Microcystis aeruginosa* strain CBT 480 with O-methyltyrosine in a 1.6 ml (dw-MTP) scale (ESI-IT-ToF-MS on the left; MALDI-ToF-MS on the right)

A, A': feeding of 300 μM O-methyltyrosine (OMetY), w/o DMSO

B, B': feeding of 30 μM O-methyltyrosine (0-MetY), w/o DMSO

C, C': feeding of 300 μM O-methyltyrosine (OMetY), w/1% DMSO

D, D': feeding of 30 μM O-methyltyrosine (OMetY), w/1% DMSO

E, E': control (no feeding)

Molecule Masses of Naturally Produced Microcystins:

995 Da=MC-LR, 1045 Da=MC-YR

Molecule masses of modified microcystin generated by feeding with O-methyltyrosine 1059 Da=MC-OMetYR

FIG. 2 D:

Detection of modified microcystins by two different mass spectrometry method after feeding of modified substrates to a *Microcystis aeruginosa* strain CBT 480 with homoarginine in a 1.6 ml (dw-MTP) scale (ESI-IT-ToF-MS detection on the left; MALDI-ToF-MS detection on the right)

A, A': feeding of 300 μM homoarginine (hR), w/o DMSO

B, B': feeding of 30 μM homoarginine (hR), w/o DMSO

C, C': feeding of 300 μM homoarginine (hR), w/1% DMSO

D, D': feeding of 30 μM homoarginine (hR), w/1% DMSO

E, E': control (no feeding)

Molecule Masses of Naturally Produced Microcystins:

995 Da=MC-LR, 1045 Da=MC-YR

Molecule masses of modified microcystins generated by feeding with homoarginine

1059 Da=MC-YhR; 1009 Da=MC-LhR

All modified microcystins could be detected with both MS methods. However, most samples resulting from feeding without the addition of DMSO of 1% in the culture medium could not be detected with MALDI-ToF-MS but with ESI-IT-ToF-MS. Therefore, it is recommended to use DMSO for feeding experiments in screenings of small scale cultures (between 1 and 10 ml culture volumes) especially if the MS detection of modified non-ribosomal peptides is based on MALDI-ToF-MS.

On the other side MALDI-ToF-MS detection of modified non-ribosomal peptides after feeding of modified substrates to small scale cultures of 1.6 ml cultivated in deep-well-microtiter plates (dw-MTW) allows for high throughput screening (HTS). Both cultivation (with and without feeding of modified substrates) and sample preparation for MALDI-ToF-MS can be done using a pipetting robot allowing for the parallel test of diverse strains and substrates as described in Tillich et al. BMC Microbiology 2014, 14:239.

FIG. 3:

McyBI represent the first of two enzyme modules of McyB and is responsible for the incorporation of the amino acid at the position 2 of the microcystin molecule. This is the amino acid leucine in case of the Microcystin *aeruginosa* strain PCC7806 whereas it is leucine OR tyrosine in the *Microcystis aeruginosa* strain CBT 480. The so called core motifs A2-A6 of the adenylation (A) domain of McyBI are highlighted in black (A2-A6) and the amino acids responsible for substrate (amino acid) recognition and activation during the biosynthesis of the respective microcystin are indicated by big and bold white letters. These amino acids form the active pocket of the A domains and the sequence in their one-letter amino acid code represent the so called specificity-conferring code of A domains which shall allow for the prediction of substrate specificity of A domains. The box and the arrow indicate the only difference in the amino acid sequence of McyBI of both strains. Only one of nine pocket-forming amino acids of the A domains of both strains is different between the strains and also the remaining parts of the A domain as well as of the whole biosynthetic gene clusters are almost identical between the strains leading to the conclusion that the incorporation of leucine and tyrosine at position 2 of the microcystin in the strain CBT 480 is a strain-specific feature but cannot be explained by differences in the DNA sequence of the biosynthetic gene clusters and amino acid sequence of the microcystin synthetases, resp.

FIGS. 4*a-e:*

Exemplary embodiment No. 1: Incorporation of the modified substrate Azido-L-Phe (Phe=phenylalanine) into Microcystin-YR in position 2 produced by strain CBT 959. HPLC-PDA Chromatogram at 238 nm for sample of control cultivation (a) for sample of cultivation with added modified substrate (b). Extracted ion chromatogram from HPLC-MS data of mass value of protonated molecular ion of novel Microcystin variant for sample of control cultivation (c) and for sample of cultivation with added modified substrate (d) in the positive ionization mode. Finally, (e) shows the averaged mass spectrum of the peak visible in chromatogram d). Detector signal intensities (y-Axis) are measured in milli-absorption units (mAU) and counts (dimensionless quantity) for PDA and mass spectrometry data, respectively.

The growth of strain CBT 959 could not be followed by measurement of optical density at 750 nm ($OD_{750\ nm}$) as the cell formed aggregates making it impossible to measure reliable $OD_{750\ nm}$ values.

FIGS. 5*a-e:*

Exemplary embodiment No. 2: Incorporation of the modified substrate Prg-Tyr (Tyr=Tyrosine) into Microcystin YR in position 2 produced by strain CBT 480.

HPLC-PDA Chromatogram at 238 nm for sample of control cultivation (a) for sample of cultivation with added modified substrate (b). Extracted ion chromatogram from HPLC-MS data of mass value of protonated molecular ion of novel Microcystin variant for sample of control cultivation (c) and sample of cultivation with added modified substrate (d) in the positive ionization mode. Finally, e) shows the averaged mass spectrum of the peak visible in chromatogram d). Detector signal intensities (y-Axis) are measured in milli-absorption units (mAU) and counts (dimensionless quantity) for PDA and mass spectrometry data respectively.

FIG. 6:

Exemplary embodiment No. 2: Growths curve of CBT 480 cultures with and without Prg-Tyr (Tyr=Tyrosine) added.

FIGS. 7*a-e:*

Exemplary embodiment No. 3: Incorporation of the modified substrate Azido-Lys (Lys=Lysine) into Microcystin LR in position 4 produced by strain CBT 275.

HPLC-PDA Chromatogram at 238 nm for sample of control cultivation (a) for sample of cultivation with added modified substrate (b). Extracted ion chromatogram from HPLC-MS data of mass value of protonated molecular ion of novel Microcystin variant for sample of control cultivation (c) and sample of cultivation with added modified substrate (d) in the positive ionization mode. Finally, e) shows the averaged mass spectrum of the peak visible in chromatogram d). Detector signal intensities (y-Axis) are measured in milli-absorption units (mAU) and counts (dimensionless quantity) for PDA and mass spectrometry data respectively.

FIG. 8:

Exemplary embodiment No. 3: Growths curve of CBT 275 cultures with and without Azido-Lys (Lys=Lysine) added.

FIGS. 9*a-e:*

Exemplary embodiment No. 4: Incorporation of the modified substrate Prg-Tyr (Tyr=Tyrosine) into Microcystin LW in position 4 produced by strain CBT 275.

HPLC-PDA Chromatogram at 238 nm for sample of control cultivation (a) for sample of cultivation with added modified substrate (b). Extracted ion chromatogram from HPLC-MS data of mass value of protonated molecular ion of novel Microcystin variant for sample of control cultivation (c) and sample of cultivation with added modified substrate (d) in the positive ionization mode. Finally, e) shows the averaged mass spectrum of the peak visible in chromatogram d). Detector signal intensities (y-Axis) are measured in milli-absorption units (mAU) and counts (dimensionless quantity) for PDA and mass spectrometry data respectively.

FIG. 10:

Exemplary embodiment No. 4: Growths curve of CBT 275 cultures with and without Prg-Tyr (Tyr=Tyrosine) added.

FIGS. 11*a-e:*

Exemplary embodiment No. 5: Incorporation of the modified substrate Nitro-Arg (Arg=Arginine) into Microcystin YR in position 4 produced by strain CBT 1.

HPLC-PDA Chromatogram at 238 nm for sample of control cultivation (a) for sample of cultivation with added modified substrate (b). Extracted ion chromatogram from HPLC-MS data of mass value of protonated molecular ion of novel Microcystin variant for sample of control cultivation (c) and sample of cultivation with added modified substrate (d) in the positive ionization mode. Finally, e) shows the averaged mass spectrum of the peak visible in chromatogram d). Detector signal intensities (y-Axis) are measured in milli-absorption units (mAU) and counts (dimensionless quantity) for PDA and mass spectrometry data respectively.

FIG. 12:

Growths curve of CBT 1 cultures with and without Nitro-Arg (Arg=Arginine) added.

FIGS. 13*a-e:*

Exemplary embodiment No. 6: Incorporation of the modified substrate Furyl-L-Ala (Ala=Alanine) into Microcystin LR in position 4 produced by strain CBT 275.

HPLC-PDA Chromatogram at 238 nm for sample of control cultivation (a) for sample of cultivation with added modified substrate (b). Extracted ion chromatogram from HPLC-MS data of mass value of protonated molecular ion of novel Microcystin variant for sample of control cultivation (c) and sample of cultivation with added modified substrate (d) in the positive ionization mode. Finally, e) shows the averaged mass spectrum of the peak visible in chromatogram d). Detector signal intensities (y-Axis) are measured in milli-absorption units (mAU) and counts (dimensionless quantity) for PDA and mass spectrometry data respectively. The PDA-Signal of the novel Furyl-Ala variant of Microcystin LR is not visible due to the low concentration.

FIG. 14:

Exemplary embodiment No. 6: Growths curve of CBT 275 cultures with and without Furyl-Ala (Ala=Alanine) added.

FIGS. 15*a-e:*

Exemplary embodiment No. 7: Incorporation of the modified substrate Nitro-Arg (Arg=Arginine) and Prg-Tyr (Tyr=Tyrosine) into Microcystin YR in position 2 and 4 respectively produced by strain CBT 480.

HPLC-PDA Chromatogram at 238 nm for sample of control cultivation (a) for sample of cultivation with added modified substrate (b). Extracted ion chromatogram from HPLC-MS data of mass value of protonated molecular ion of novel Microcystin variant for sample of control cultivation (c) and sample of cultivation with added modified substrate (d) in the positive ionization mode. Finally, e) shows the averaged mass spectrum of the peak visible in chromatogram d). Detector signal intensities (y-Axis) are measured in milli-absorption units (mAU) and counts (dimensionless quantity) for PDA and mass spectrometry data respectively.

FIG. 16:

Exemplary embodiment No. 7: Growths curve of CBT 480 cultures with and without Nitro-Arg (Arg=Arginine) and Prg-Tyr (Tyr=Tyrosine) added.

FIGS. 17*a-e:*

Exemplary embodiment No. 8: Incorporation of the modified substrate Nitro-Arg (Arg=Arginine) into Microcystin (D-Asp3, E-Dhb7)-RR in position 2/4 produced by strain CBT 329.

HPLC-PDA Chromatogram at 238 nm for sample of control cultivation (a) for sample of cultivation with added modified substrate (b). Extracted ion chromatogram from HPLC-MS data of mass value of double protonated molecular ion of novel Microcystin variant for sample of control cultivation (c) and sample of cultivation with added modified substrate (d) in the positive ionization mode. Finally, e)

shows the averaged mass spectrum of the peak visible in chromatogram d). Detector signal intensities (y-Axis) are measured in milli-absorption units (mAU) and counts (dimensionless quantity) for PDA and mass spectrometry data respectively.

FIG. 18:

Exemplary embodiment No. 8: Growths curve of CBT 329 cultures with and without Nitro-Arg (Arg=Arginine) added.

FIGS. 19*a-e:*

Exemplary embodiment No. 9: Incorporation of the modified substrate Azido-Lys (Lys=Lysine) into Microcystin YR in position 4 produced by strain CBT 1.

HPLC-PDA Chromatogram at 238 nm for sample of control cultivation (a) for sample of cultivation with added modified substrate (b). Extracted ion chromatogram from HPLC-MS data of mass value of protonated molecular ion of novel Microcystin variant for sample of control cultivation (c) and sample of cultivation with added modified substrate (d) in the positive ionization mode. Finally, e) shows the averaged mass spectrum of the peak visible in chromatogram d). Detector signal intensities (y-Axis) are measured in milli-absorption units (mAU) and counts (dimensionless quantity) for PDA and mass spectrometry data respectively. The PDA-Signal of the novel Azido-Lys (Lys=Lysine) variant of Microcystin YR is not visible due to overlapping peaks in the sample.

FIG. 20:

Exemplary embodiment No. 9: Growths curve of CBT 1 cultures with and without Azido-Lys (Lys=Lysine) added.

FIGS. 21*a-e:*

Exemplary embodiment No. 10: Incorporation of the modified substrate Azido-Norval (Norval=Norvaline) into Microcystin RR in position 2 produced by strain CBT 633.

HPLC-PDA Chromatogram at 238 nm for sample of control cultivation (a) for sample of cultivation with added modified substrate (b). Extracted ion chromatogram from HPLC-MS data of mass value of protonated molecular ion of novel Microcystin variant for sample of control cultivation (c) and sample of cultivation with added modified substrate (d) in the positive ionization mode. Finally, e) shows the averaged mass spectrum of the peak visible in chromatogram d). Detector signal intensities (y-Axis) are measured in milli-absorption units (mAU) and counts (dimensionless quantity) for PDA and mass spectrometry data respectively.

FIG. 22:

Growths curve of CBT 633 cultures with and without Azido-Norval (Norval=Norvaline) added.

FIGS. 23*a-e:*

Exemplary embodiment No. 11: Incorporation of the modified substrate H-homoarg-OH (homoarg=homoarginine) into Nodularin in position 2 produced by strain CBT 786.

HPLC-PDA Chromatogram at 238 nm for sample of control cultivation (a) for sample of cultivation with added modified substrate (b). Extracted ion chromatogram from HPLC-MS data of mass value of protonated molecular ion of novel Nodularin variant for sample of control cultivation (c) and sample of cultivation with added modified substrate (d) in the positive ionization mode. Finally, e) shows the averaged mass spectrum of the peak visible in chromatogram d). Detector signal intensities (y-Axis) are measured in milli-absorption units (mAU) and counts (dimensionless quantity) for PDA and mass spectrometry data respectively.

FIGS. 24*a-e:*

Exemplary embodiment No. 12: Incorporation of the modified substrate Azido-L-Phe (Phe=phenylalanine) into Microcystin YR in position 2 produced by strain CBT 480 in a large scale (2 l) cultivation system.

HPLC-PDA Chromatogram at 238 nm for sample of control cultivation (a) for sample of cultivation with added modified substrate (b). Extracted ion chromatogram from HPLC-MS data of mass value of protonated molecular ion of novel Microcystin variant for sample of control cultivation (c) and sample of cultivation with added modified substrate (d) in the positive ionization mode. Finally, e) shows the averaged mass spectrum of the peak visible in chromatogram d). Detector signal intensities (y-Axis) are measured in milli-absorption units (mAU) and counts (dimensionless quantity) for PDA and mass spectrometry data respectively.

FIG. 25:

Exemplary embodiment No. 13: Feeding of *Microcystis aeruginosa* strain CBT 480 with different amounts of modified substrate 4-azido-L-phenylalanine (0 μM, 10 μM, 30 μM) results an increasing amount of produced modified microcystin with increasing amount of fed modified substrate 4-azido-L-phenylalanine. This result allows for optimization of feeding protocols for respective productions of modified non-ribosomal peptides (here modified microcystins).

The upper part of the figure shoes overlaid HPLC-PDA Chromatograms at 238 nm for sample of control cultivation, sample of cultivation with added substrate 4-azido-L-phenylalanine of 10 μM in culture medium and sample of cultivation with added substrate 4-azido-L-phenylalanine of 30 μM in culture medium. The lower figure shows the averaged mass spectrum of the newly formed peak visible at about 10 min in the HPLC chromatogram. Detector signal intensities (y-Axis) are measured in milli-absorption units (mAU) and counts (dimensionless quantity) for PDA and mass spectrometry data, respectively.

FIGS. 26*a-e:*

Exemplary embodiment No. 14: Incorporation of the modified substrate Prg-Tyr (Tyr=Tyrosine) into (D-$Asp^3$, E-$Dhb^7$) Microcystin-RR in position 2 produced by strain CBT 280.

HPLC-PDA Chromatogram at 238 nm for sample of control cultivation (a) for sample of cultivation with added modified substrate (b). Extracted ion chromatogram from HPLC-MS data of mass value of protonated molecular ion of novel Microcystin variant for sample of control cultivation (c) and sample of cultivation with added modified substrate (d) in the positive ionization mode. Finally, e) shows the averaged mass spectrum of the peak visible in chromatogram d). Detector signal intensities (y-Axis) are measured in milli-absorption units (mAU) and counts (dimensionless quantity) for PDA and mass spectrometry data respectively.

FIGS. 27*a-e:*

Exemplary embodiment No. 15: Incorporation of the modified substrate Prg-Tyr (Tyr=Tyrosine) into Anabaenopeptin A in position 2 produced by strain CBT 280.

HPLC-PDA Chromatogram at 210 nm for sample of control cultivation (a) for sample of cultivation with added modified substrate (b). Extracted ion chromatogram from HPLC-MS data of mass value of protonated molecular ion of novel Anabaenopeptin variant for sample of control cultivation (c) and sample of cultivation with added modified substrate (d) in the positive ionization mode. Finally, e) shows the averaged mass spectrum of the peak visible in chromatogram d). Detector signal intensities (y-Axis) are measured in milli-absorption units (mAU) and counts (dimensionless quantity) for PDA and mass spectrometry data respectively.

FIGS. 28*a-e:*

Exemplary embodiment No. 16: Incorporation of the modified substrate Azido-Phe (Phe=Phenylalanine) into Anabaenopeptin NZ857 produced by strain CBT 332.

HPLC-PDA Chromatogram at 210 nm for sample of control cultivation (a) for sample of cultivation with added modified substrate (b). Extracted ion chromatogram from HPLC-MS data of mass value of protonated molecular ion of novel Anabaenopeptin variant for sample of control cultivation (c) and sample of cultivation with added modified substrate (d) in the positive ionization mode. Finally, e) shows the averaged mass spectrum of the peak visible in chromatogram d). Detector signal intensities (y-Axis) are measured in milli-absorption units (mAU) and counts (dimensionless quantity) for PDA and mass spectrometry data respectively.

FIGS. 29*a-e:*

Exemplary embodiment No. 17: Incorporation of the modified substrate Azido-Phe (Phe=Phenylalanine) into Oscillamide Y produced by strain CBT 1161.

HPLC-PDA Chromatogram at 210 nm for sample of control cultivation (a) for sample of cultivation with added modified substrate (b). Extracted ion chromatogram from HPLC-MS data of mass value of protonated molecular ion of novel Oscillamide variant for sample of control cultivation (c) and sample of cultivation with added modified substrate (d) in the positive ionization mode. Finally, e) shows the averaged mass spectrum of the peak visible in chromatogram d). Detector signal intensities (y-Axis) are measured in milli-absorption units (mAU) and counts (dimensionless quantity) for PDA and mass spectrometry data respectively.

FIGS. 30*a-e:*

Exemplary embodiment No. 18: Incorporation of the modified substrate Prg-Tyr (Tyr=Tyrosine) into Oscillamide Y produced by strain CBT 1161.

HPLC-PDA Chromatogram at 210 nm for sample of control cultivation (a) for sample of cultivation with added modified substrate (b). Extracted ion chromatogram from HPLC-MS data of mass value of protonated molecular ion of novel Oscillamide variant for sample of control cultivation (c) and sample of cultivation with added modified substrate (d) in the positive ionization mode. Finally, e) shows the averaged mass spectrum of the peak visible in chromatogram d). Detector signal intensities (y-Axis) are measured in milli-absorption units (mAU) and counts (dimensionless quantity) for PDA and mass spectrometry data respectively.

FIGS. 31*a-c:*

Exemplary embodiment No. 19: Incorporation of the modified substrate Prg-Tyr (Tyr=Tyrosine) into Cryptophycin 1 produced by strain CBT 567.

Extracted ion chromatogram from HPLC-MS data of mass value of protonated molecular ion of novel Cryptophycin variant for sample of control cultivation (a) and sample of cultivation with added modified substrate (b) in the positive ionization mode. Finally, c) shows the averaged mass spectrum of the additional peak in chromatogram b). Detector signal intensities (y-Axis) are measured in counts (dimensionless quantity).

FIG. 32:

Exemplary embodiment No. 20: Produced ADCs and results of analytical SEC-HPLC. In analytical SEC-HPLC the conjugates Microcystin-ADC1 and Microcystin-ADC2 showed a high level of purity with 98.9% and 99.0% monomers. In both cases, aggregates and small fragments were detected with rates of 0.8% and 0.2%.

FIG. 33:

Exemplary embodiment No. 21: Coomassie stained Gelelectrophoresis gels demonstrating the binding of Microcystin variants 1 and 2 as payloads on monoclonal antibodies. In Coomassie staining under reducing conditions all samples showed a signal for the heavy chain at app. 50 kDa and the light chain at app. 25 kDa. All conjugates showed an up-shift of the protein signal of the heavy and the light chain compared to the naked MAB indicating toxin conjugation to both antibody chains. For all ADCs a double-signal was detected for the light chain indicating both, conjugated and unconjugated species. In Coomassie staining under non-reducing conditions the naked antibody showed a double signal at app. 150 kDa for the intact antibody. The ADCs showed a variety of signals between 25 kDa and 150 kDa, since in both cases the toxin was conjugated to reduced interchain disulfides leading to instability of the antibody during incubation at 37° C.

FIG. 34:

Exemplary embodiment No. 22: Successful in vitro proof of concept of Microcystin-based ADCs. The cell viability is monitored in an in-vitro-assay with a cancer cell line for the different concentrations of the Microcystin ADC for two Microcystin variants as payloads. The ADC carries a non-cleavable linker. For Microcystin-ADC-2 an $EC_{50}$ values of 220 pM was determined. Differences between structural payload variants underline huge potential of further structural optimizations.

The invention claimed is:

1. A method of producing a modified non-ribosomal peptide from cyanobacteria, comprising:

a) growing a non-ribosomal peptide producing cyanobacteria strain in a culture medium, b) adding one or more modified substrates to said culture medium, and c) growing the cyanobacteria strain in the presence of said one or more modified substrates, wherein the one or more modified substrates are a modified amino acid that is not found in nature in the non-ribosomal peptide produced by said cyanobacteria strain, which comprises an anchor group that is directly accessible or transformable for use in conjugation chemistry for the attachment of a targeting moiety or a label.

2. The method according to claim 1, further comprising: selecting the cyanobacteria strain based upon incorporation of the one or more modified substrates into the non-ribosomal peptide occurs at a defined position.

3. The method according to claim 1, wherein the non-ribosomal peptide is a microcystin of the following general structure:

$$D\text{-}Ala_1\text{-}X_2\text{-}D\text{-}MeAsp_3\text{-}Z_4\text{-}Adda_5\text{-}DGlu_6\text{-}Mdha_7$$

wherein $X_2$ and $Z_4$ are L-amino acids, and wherein the one or more modified substrates are incorporated in at least one position other than $Adda_5$ and $DGlu_6$.

4. The method according to claim 3, wherein the incorporation of said one or more modified substrates occurs in position $X_2$ and/or $Z_4$.

5. The method according to claim 1, wherein the non-ribosomal peptide is a nodularin of the following general structure:

$$D\text{-}MeAsp_1\text{-}Arg_2\text{-}Adda_3\text{-}DGlu_4\text{-}Mdhb_5$$

and wherein the one or more modified substrates are incorporated at any position other than Adda3 and DGlu4.

6. The method according to claim 5, wherein the incorporation of said one or more modified substrates occurs in position $Arg_2$.

7. The method according to claim 3, wherein the modified position is $X_2$ and the one or more modified substrates are a modified amino acid.

8. The method according to claim 3, wherein the modified position is $Z_4$ and the one or more modified substrates are a modified amino acid.

9. The method according to claim 5, wherein the modified position is $Arg_2$ and the one or more modified substrates are a modified amino acid.

10. The method according to claim 1, wherein the one or more modified substrates is at least one substrate selected from the group consisting of (2S)-2-amino-3-azidopropanoic acid, (2S)-2-amino-6-azidohexanoic acid, (S)-2-Amino-5-azidopentanoic acid, (2S)-2-amino-3-(4-prop-2-ynyloxyphenyl)propanoic acid, (2S)-2-amino-5-(N'-nitrocarbamimidamido)pentanoic acid, (2S)-2-amino-3-(furan-2-yl)propanoic acid, (S)-Amino-6-((prop-2-ynyloxy)carbonylamino)hexanoic acid, and (2S)-2-Amino-3-(4-azidophenyl)propanoic acid.

11. The method according to claim 3, wherein in the modified non-ribosomal peptide, independently of one another, D-$Ala_1$ is selected from the group consisting of D-Ala, D-Ser and D-Leu, D-$MeAsp_3$ is selected from the group consisting of D-MeAsp and D-Asp, $Adda_5$ is selected from the group consisting of Adda, DM-Adda, (6Z)Adda and ADM-Adda, $DGlu_6$ is selected from the group consisting of D-Glu and D-Glu(OCH3), $Mdha_7$ is selected from the group consisting of Mdha, Dha, L-Ser, L-MeSer, Dhb, and MeLan, and $X_2$ and/or $Z_4$ comprise the at least one modified substrate.

12. The method according to claim 5, wherein in the modified non-ribosomal peptide, independently of one another, $MeAsp_1$ is selected from the group consisting of D-MeAsp and D-Asp, $Arg_2$ is selected from the group consisting of Arg and Homo-Arg, $Adda_3$ is selected from the group consisting of Adda, DM-Adda, (6Z)Adda and Me-Adda, $DGlu_4$ is selected from the group consisting of D-Glu and D-Glu($OCH_3$), $Mdhb_5$ is selected from the group consisting of Mdhb and Dhb, and wherein the position for $MeAsp_1$, $Arg_2$ and $Mdhb_5$ comprises the at least one modified substrate.

13. The method according to claim 1, wherein the concentration of the one or more modified substrates in the culture medium is between 5 μM and 500 μM and/or DMSO is added as an additional ingredient.

14. The method according to claim 1, wherein the conjugation chemistry is at least one selected from the group consisting of copper(I)-catalyzed azide-alkyne cycloaddition, strain promoted azide-alkyne cycloaddition, alkyne-azide cycloaddition, alkene-tetrazine inverse-demand Diels-Alder reaction, and reactions exploiting the specific reactivities of primary amines, thiols, aldehydes, carboxyls, and oximes.

15. The method according to claim 1, wherein the cyanobacteria strain is at least one selected from the group consisting of *Microcystis, Planktothrix, Oscillatoria, Nostoc, Anabaena, Aphanizomenon, Hapalosiphon, Nodularia, Lyngbya, Phormidium, Spirulina, Halospirulina, Arthrospira, Trichodesmium, Leptolyngbya, Plectonema, Myxosarcina, Pleurocapsa, Pseudanabaena, Geitlerinema, Euhalothece, Calothrix, Tolypothrix, Scytonema, Fischerella, Mastigocladus, Westiellopsis, Stigonema, Chlorogloeopsis, Cyanospira, Cylindrospermopsis, Cylindrospermum, Microchaete, Rivularia, Autosira, Trichonema, Trichodesmium, Symploca, Starria, Prochlorothrix, Microcoleus, Limnothrix, Crinalium, Borzia, Chroococcidiopsis, Cyanocystis, Dermocarpella, Staniera, Xenococcus, Chamaesiphon, Chroococcus, Cyanobacterium, Cyanobium, Cyanothece, Dactylococcopsis, Gloeobacter, Gloeocapsa*, and *Gloeothece*.

16. A method of producing a compound for targeted therapy comprising a non-ribosomal peptide linked to a targeting moiety, the method comprising:

A) providing a targeting moiety and a non-ribosomal peptide comprising at least one modified amino acid, wherein the at least one modified amino acid comprises an anchor group directly accessible or transformable for use in conjugation chemistry by performing a method according to claim 1, and B) attaching said targeting moiety to said non-ribosomal peptide via chemical conjugation to said anchor group.

17. The method according to claim 16, wherein the targeting moiety is attached via a linker arranged between the modified amino acid and the targeting moiety.

18. The method according to claim 16, wherein the targeting moiety is an antibody.

19. The method according to claim 1, wherein the one or more modified substrates are the modified amino acid which comprises an anchor group directly accessible or transformable for use in click chemistry.

20. The method according to claim 1, wherein said anchor group that is directly accessible for use in conjugation chemistry is selected from the group consisting of azide, alkyne, tetrazine, primary amine, thiol, aldehyde, carboxyl, and oxime.

21. The method according to claim 1, wherein the anchor group that is directly transformable for use in conjugation chemistry is selected from the group consisting of a furanyl group and a nitro group.

22. The method according to claim 1, wherein the one or more modified substrates is at least one substrate selected from the group consisting of N-Propargyl-Lysine and L-α-Amino-ε-guanidinohexanoic acid.

* * * * *

SEQUENCE LISTING

```
<160> NUMBER OF SEQ ID NOS: 13

<210> SEQ ID NO 1
<211> LENGTH: 7
<212> TYPE: PRT
<213> ORGANISM: Microcystis aeruginosa
<220> FEATURE:
<221> NAME/KEY: MOD_RES
<222> LOCATION: (1)..(1)
<223> OTHER INFORMATION: D-Ala, D-Ser, D-Leu, Azido-L-Ala, Azido-Lys,
      Azido-Norval, Prg-Tyr, Nitro-Arg, Furyl-Ala, Lys(Poc), Azido-L-Phe
      or H-homo-Arg-OH
<220> FEATURE:
<221> NAME/KEY: MOD_RES
<222> LOCATION: (2)..(2)
<223> OTHER INFORMATION: L-Leu, L-Ala, L-Tyr, L-Glu, L-Val, L-Glu(OMe),
```

-continued

```
      L-Arg, L-Phe, L-Met(O), L-H-Phe, L-H-Tyr, L-Trp, L-H-Arg, L-H-Ile,
      L-H4Tyr, Azido-L-Ala, Azido-Lys, Azido-Norval, Prg-Tyr, Nitro-Arg,
      Furyl-Ala, Lys(Poc), Azido-L-Phe or H-homo-Arg-OH
<220> FEATURE:
<221> NAME/KEY: MOD_RES
<222> LOCATION: (3)..(3)
<223> OTHER INFORMATION: D-Asp, D-MeAsp, Azido-L-Ala, Azido-Lys, Azido-
      Norval, Prg-Tyr, Nitro-Arg, Furyl-Ala, Lys(Poc), Azido-L-Phe or H-
      homo-Arg-OH
<220> FEATURE:
<221> NAME/KEY: MOD_RES
<222> LOCATION: (4)..(4)
<223> OTHER INFORMATION: L-Ala, Aba, L-Leu, L-Arg, L-Glu, L-Glu(OMe),
      L-Phe, L-Tyr, L-LHar, L-Trp, L-Met(O), L-H-Arg, Azido-L-Ala,
      Azido-Lys, Azido-Norval, Prg-Tyr, Nitro-Arg, Furyl-Ala, Lys(Poc),
      Azido-L-Phe or H-homo-Arg-OH
<220> FEATURE:
<221> NAME/KEY: VARIANT
<222> LOCATION: (5)..(5)
<223> OTHER INFORMATION: Adda, DM-Adda, (6Z)Adda or ADM-Adda
<220> FEATURE:
<221> NAME/KEY: VARIANT
<222> LOCATION: (6)..(6)
<223> OTHER INFORMATION: D-Glu or D-Glu(OCH3)
<220> FEATURE:
<221> NAME/KEY: MOD_RES
<222> LOCATION: (7)..(7)
<223> OTHER INFORMATION: Mdha, Dha, L-Ser, L-MeSer, Dhb, MeLan, Azido-L-
      Ala, Azido-Lys, Azido-Norval, Prg-Tyr, Nitro-Arg, Furyl-Ala,
      Lys(Poc), Azido-L-Phe or H-homo-Arg-OH

<400> SEQUENCE: 1

Xaa Xaa Xaa Xaa Xaa Glu Xaa
1               5


<210> SEQ ID NO 2
<211> LENGTH: 5
<212> TYPE: PRT
<213> ORGANISM: Nodularia sp.
<220> FEATURE:
<221> NAME/KEY: MOD_RES
<222> LOCATION: (1)..(1)
<223> OTHER INFORMATION: MeAsp, D-MeAsp, D-Asp, Azido-L-Ala, Azido-Lys,
      Azido-Norval, Prg-Tyr, Nitro-Arg, Furyl-Ala, Lys(Poc), Azido-L-Phe
      or H-homo-Arg-OH
<220> FEATURE:
<221> NAME/KEY: MOD_RES
<222> LOCATION: (2)..(2)
<223> OTHER INFORMATION: Arg, Homo-Arg, Azido-L-Ala, Azido-Lys, Azido-
      Norval, Prg-Tyr, Nitro-Arg, Furyl-Ala, Lys(Poc), Azido-L-Phe or H-
      homo-Arg-OH
<220> FEATURE:
<221> NAME/KEY: VARIANT
<222> LOCATION: (3)..(3)
<223> OTHER INFORMATION: Adda, DM-Adda, (6Z)Adda or MeAdda
<220> FEATURE:
<221> NAME/KEY: VARIANT
<222> LOCATION: (4)..(4)
<223> OTHER INFORMATION: D-Glu or D-Glu(OCH3)
<220> FEATURE:
<221> NAME/KEY: MOD_RES
<222> LOCATION: (5)..(5)
<223> OTHER INFORMATION: Mdhb, Dhb, Azido-L-Ala, Azido-Lys, Azido-
      Norval, Prg-Tyr, Nitro-Arg, Furyl-Ala, Lys(Poc), Azido-L-Phe or H-
      homo-Arg-OH

<400> SEQUENCE: 2

Xaa Xaa Xaa Glu Xaa
1               5


<210> SEQ ID NO 3
<211> LENGTH: 6
<212> TYPE: PRT
<213> ORGANISM: Microcystis aeruginosa
<220> FEATURE:
```

<221> NAME/KEY: MOD_RES
<222> LOCATION: (1)..(1)
<223> OTHER INFORMATION: Tyr, Arg, Lys, Phe, Ile, HArg, Azido-L-Ala, Azido-Lys, Azido-Norval, Prg-Tyr, Nitro-Arg, Furyl-Ala, Lys(Poc), Prg-Lys, Azido-L-Phe or H-homo-Arg-OH
<220> FEATURE:
<221> NAME/KEY: VARIANT
<222> LOCATION: (3)..(3)
<223> OTHER INFORMATION: Val or Ile
<220> FEATURE:
<221> NAME/KEY: VARIANT
<222> LOCATION: (4)..(4)
<223> OTHER INFORMATION: HTyr, MeHTyr or HPhe
<220> FEATURE:
<221> NAME/KEY: VARIANT
<222> LOCATION: (5)..(5)
<223> OTHER INFORMATION: MeAla, MeLeu, MeHTyr or MeTyr
<220> FEATURE:
<221> NAME/KEY: MOD_RES
<222> LOCATION: (6)..(6)
<223> OTHER INFORMATION: Phe, Tyr, Ile, Leu, Azido-L-Ala, Azido-Lys, Azido-Norval, Prg-Tyr, Nitro-Arg, Furyl-Ala, Lys(Poc), Prg-Lys, Azido-L-Phe or H-homo-Arg-OH

<400> SEQUENCE: 3

Xaa Lys Xaa Xaa Xaa Xaa
1               5

<210> SEQ ID NO 4
<211> LENGTH: 6
<212> TYPE: PRT
<213> ORGANISM: Microcystis aeruginosa
<220> FEATURE:
<221> NAME/KEY: MOD_RES
<222> LOCATION: (1)..(1)
<223> OTHER INFORMATION: Tyr, Arg, Azido-L-Ala, Azido-Lys, Azido-Norval, Prg-Tyr, Nitro-Arg, Furyl-Ala, Lys(Poc), Prg-Lys, Azido-L-Phe or H-homo-Arg-OH
<220> FEATURE:
<221> NAME/KEY: VARIANT
<222> LOCATION: (3)..(3)
<223> OTHER INFORMATION: Met or Ile
<220> FEATURE:
<221> NAME/KEY: MOD_RES
<222> LOCATION: (4)..(4)
<223> OTHER INFORMATION: HTyr, Azido-L-Ala, Azido-Lys, Azido-Norval, Prg-Tyr, Nitro-Arg, Furyl-Ala, Lys(Poc), Prg-Lys, Azido-L-Phe or H-homo-Arg-OH
<220> FEATURE:
<221> NAME/KEY: VARIANT
<222> LOCATION: (5)..(5)
<223> OTHER INFORMATION: MeAla or MeHTyr

<400> SEQUENCE: 4

Xaa Lys Xaa Xaa Xaa Phe
1               5

<210> SEQ ID NO 5
<211> LENGTH: 4
<212> TYPE: PRT
<213> ORGANISM: Nostoc sp.
<220> FEATURE:
<221> NAME/KEY: MOD_RES
<222> LOCATION: (2)..(2)
<223> OTHER INFORMATION: O-methyl-L-tyrosine, N, O-dimethyl chloro-L-tyrosine, Azido-L-Ala, Azido-Lys, Azido-Norval, Prg-Tyr, Nitro-Arg, Furyl-Ala, Lys(Poc), Prg-Lys, Azido-L-Phe, H-homo-Arg-OH
<220> FEATURE:
<221> NAME/KEY: VARIANT
<222> LOCATION: (3)..(3)
<223> OTHER INFORMATION: Methyl-beta-alanine
<220> FEATURE:
<221> NAME/KEY: VARIANT
<222> LOCATION: (4)..(4)
<223> OTHER INFORMATION: Alfa-ketoisocaproic acid

<400> SEQUENCE: 5

Phe Xaa Xaa Xaa
1

<210> SEQ ID NO 6
<211> LENGTH: 7
<212> TYPE: PRT
<213> ORGANISM: Planktothrix rubescence
<220> FEATURE:
<221> NAME/KEY: MOD_RES
<222> LOCATION: (1)..(1)
<223> OTHER INFORMATION: D-Ala, D-Ser, D-Leu, Azido-L-Ala, Azido-Lys, Azido-Norval, Prg-Tyr, Nitro-Arg, Furyl-Ala, Lys(Poc), Azido-L-Phe or H-homo-Arg-OH
<220> FEATURE:
<221> NAME/KEY: MOD_RES
<222> LOCATION: (2)..(2)
<223> OTHER INFORMATION: L-Leu, L-Ala, L-Tyr, L-Glu, L-Val, L-Glu(OMe), L-Arg, L-Phe, L-Met(O), L-H-Phe, L-H-Tyr, L-Trp, L-H-Arg, L-H-Ile, L-H4Tyr, Azido-L-Ala, Azido-Lys, Azido-Norval, Prg-Tyr, Nitro-Arg, Furyl-Ala, Lys(Poc), Azido-L-Phe or H-homo-Arg-OH
<220> FEATURE:
<221> NAME/KEY: MOD_RES
<222> LOCATION: (3)..(3)
<223> OTHER INFORMATION: D-Asp, D-MeAsp, Azido-L-Ala, Azido-Lys, Azido-Norval, Prg-Tyr, Nitro-Arg, Furyl-Ala, Lys(Poc), Azido-L-Phe or H-homo-Arg-OH
<220> FEATURE:
<221> NAME/KEY: MOD_RES
<222> LOCATION: (4)..(4)
<223> OTHER INFORMATION: L-Ala, Aba, L-Leu, L-Arg, L-Glu, L-Glu(OMe), L-Phe, L-Tyr, L-LHar, L-Trp, L-Met(O), L-H-Arg, Azido-L-Ala, Azido-Lys, Azido-Norval, Prg-Tyr, Nitro-Arg, Furyl-Ala, Lys(Poc), Azido-L-Phe or H-homo-Arg-OH
<220> FEATURE:
<221> NAME/KEY: VARIANT
<222> LOCATION: (5)..(5)
<223> OTHER INFORMATION: Adda, DM-Adda, (6Z)Adda or ADM-Adda
<220> FEATURE:
<221> NAME/KEY: VARIANT
<222> LOCATION: (6)..(6)
<223> OTHER INFORMATION: D-Glu or D-Glu(OCH3)
<220> FEATURE:
<221> NAME/KEY: MOD_RES
<222> LOCATION: (7)..(7)
<223> OTHER INFORMATION: Mdha, Dha, L-Ser, L-MeSer, Dhb, MeLan, Azido-L-Ala, Azido-Lys, Azido-Norval, Prg-Tyr, Nitro-Arg, Furyl-Ala, Lys(Poc), Azido-L-Phe or H-homo-Arg-OH

<400> SEQUENCE: 6

Xaa Xaa Xaa Xaa Xaa Glu Xaa
1               5

<210> SEQ ID NO 7
<211> LENGTH: 6
<212> TYPE: PRT
<213> ORGANISM: Planktothrix rubescence
<220> FEATURE:
<221> NAME/KEY: MOD_RES
<222> LOCATION: (1)..(1)
<223> OTHER INFORMATION: Tyr, Arg, Lys, Phe, Ile, HArg, Azido-L-Ala, Azido-Lys, Azido-Norval, Prg-Tyr, Nitro-Arg, Furyl-Ala, Lys(Poc), Prg-Lys, Azido-L-Phe or H-homo-Arg-OH
<220> FEATURE:
<221> NAME/KEY: VARIANT
<222> LOCATION: (3)..(3)
<223> OTHER INFORMATION: Val or Ile
<220> FEATURE:
<221> NAME/KEY: VARIANT
<222> LOCATION: (4)..(4)
<223> OTHER INFORMATION: HTyr, MeHTyr or HPhe
<220> FEATURE:
<221> NAME/KEY: VARIANT
<222> LOCATION: (5)..(5)

-continued

```
<223> OTHER INFORMATION: MeAla, MeLeu, MeHTyr or MeTyr
<220> FEATURE:
<221> NAME/KEY: MOD_RES
<222> LOCATION: (6)..(6)
<223> OTHER INFORMATION: Phe, Tyr, Ile, Leu, Azido-L-Ala, Azido-Lys,
      Azido-Norval, Prg-Tyr, Nitro-Arg, Furyl-Ala, Lys(Poc), Prg-Lys,
      Azido-L-Phe or H-homo-Arg-OH

<400> SEQUENCE: 7

Xaa Lys Xaa Xaa Xaa Xaa
1               5


<210> SEQ ID NO 8
<211> LENGTH: 6
<212> TYPE: PRT
<213> ORGANISM: Planktothrix aghardii
<220> FEATURE:
<221> NAME/KEY: MOD_RES
<222> LOCATION: (1)..(1)
<223> OTHER INFORMATION: Tyr, Arg, Lys, Phe, Ile, HArg, Azido-L-Ala,
      Azido-Lys, Azido-Norval, Prg-Tyr, Nitro-Arg, Furyl-Ala, Lys(Poc),
      Prg-Lys, Azido-L-Phe or H-homo-Arg-OH
<220> FEATURE:
<221> NAME/KEY: VARIANT
<222> LOCATION: (3)..(3)
<223> OTHER INFORMATION: Val or Ile
<220> FEATURE:
<221> NAME/KEY: VARIANT
<222> LOCATION: (4)..(4)
<223> OTHER INFORMATION: HTyr, MeHTyr or HPhe
<220> FEATURE:
<221> NAME/KEY: VARIANT
<222> LOCATION: (5)..(5)
<223> OTHER INFORMATION: MeAla, MeLeu, MeHTyr or MeTyr
<220> FEATURE:
<221> NAME/KEY: MOD_RES
<222> LOCATION: (6)..(6)
<223> OTHER INFORMATION: Phe, Tyr, Ile, Leu, Azido-L-Ala, Azido-Lys,
      Azido-Norval, Prg-Tyr, Nitro-Arg, Furyl-Ala, Lys(Poc), Prg-Lys,
      Azido-L-Phe or H-homo-Arg-OH

<400> SEQUENCE: 8

Xaa Lys Xaa Xaa Xaa Xaa
1               5


<210> SEQ ID NO 9
<211> LENGTH: 6
<212> TYPE: PRT
<213> ORGANISM: Planktothrix rubescence
<220> FEATURE:
<221> NAME/KEY: MOD_RES
<222> LOCATION: (1)..(1)
<223> OTHER INFORMATION: Tyr, Arg, Azido-L-Ala, Azido-Lys, Azido-Norval,
      Prg-Tyr, Nitro-Arg, Furyl-Ala, Lys(Poc), Prg-Lys, Azido-L-Phe or
      H-homo-Arg-OH
<220> FEATURE:
<221> NAME/KEY: VARIANT
<222> LOCATION: (3)..(3)
<223> OTHER INFORMATION: Met or Ile
<220> FEATURE:
<221> NAME/KEY: MOD_RES
<222> LOCATION: (4)..(4)
<223> OTHER INFORMATION: HTyr, Azido-L-Ala, Azido-Lys, Azido-Norval,
      Prg-Tyr, Nitro-Arg, Furyl-Ala, Lys(Poc), Prg-Lys, Azido-L-Phe or
      H-homo-Arg-OH
<220> FEATURE:
<221> NAME/KEY: VARIANT
<222> LOCATION: (5)..(5)
<223> OTHER INFORMATION: MeAla or MeHTyr

<400> SEQUENCE: 9

Xaa Lys Xaa Xaa Xaa Phe
1               5
```

-continued

```
<210> SEQ ID NO 10
<211> LENGTH: 6
<212> TYPE: PRT
<213> ORGANISM: Planktothrix aghardii
<220> FEATURE:
<221> NAME/KEY: MOD_RES
<222> LOCATION: (1)..(1)
<223> OTHER INFORMATION: Tyr, Arg, Azido-L-Ala, Azido-Lys, Azido-Norval,
      Prg-Tyr, Nitro-Arg, Furyl-Ala, Lys(Poc), Prg-Lys, Azido-L-Phe or
      H-homo-Arg-OH
<220> FEATURE:
<221> NAME/KEY: VARIANT
<222> LOCATION: (3)..(3)
<223> OTHER INFORMATION: Met or Ile
<220> FEATURE:
<221> NAME/KEY: MOD_RES
<222> LOCATION: (4)..(4)
<223> OTHER INFORMATION: HTyr, Azido-L-Ala, Azido-Lys, Azido-Norval,
      Prg-Tyr, Nitro-Arg, Furyl-Ala, Lys(Poc), Prg-Lys, Azido-L-Phe or
      H-homo-Arg-OH
<220> FEATURE:
<221> NAME/KEY: VARIANT
<222> LOCATION: (5)..(5)
<223> OTHER INFORMATION: MeAla or MeHTyr

<400> SEQUENCE: 10

Xaa Lys Xaa Xaa Xaa Phe
1               5


<210> SEQ ID NO 11
<211> LENGTH: 300
<212> TYPE: PRT
<213> ORGANISM: Microcystis aeruginosa
<220> FEATURE:
<221> NAME/KEY: MISC_FEATURE
<222> LOCATION: (1)..(300)
<223> OTHER INFORMATION: Query Sequence: McyBI of the Microcystis
      aeruginosa strain CBT480

<400> SEQUENCE: 11

Gly Ile Leu Lys Ala Gly Gly Ala Tyr Val Pro Leu Asp Pro Asp Tyr
1               5                   10                  15

Pro Thr Glu Arg Leu Gly Asp Ile Leu Ser Asp Ser Gly Val Ser Leu
            20                  25                  30

Val Leu Thr Gln Glu Ser Leu Gly Asp Phe Leu Pro Gln Thr Gly Ala
        35                  40                  45

Glu Ser Leu Cys Leu Asp Arg Asp Trp Glu Lys Ile Ala Thr Tyr Ser
    50                  55                  60

Pro Glu Asn Pro Phe Asn Leu Thr Thr Pro Glu Asn Leu Ala Tyr Val
65                  70                  75                  80

Ile Tyr Thr Ser Gly Ser Thr Gly Lys Pro Lys Gly Val Leu Ile Ser
                85                  90                  95

His Arg Gly Leu Met Asn Ser Ile Cys Trp Tyr Gln Asp Ala Phe Glu
            100                 105                 110

Ile Thr Pro Leu Asp Lys Thr Thr Gln Leu Ala Arg Ile Ala Phe Asp
        115                 120                 125

Ala Ala Val Leu Glu Leu Trp Pro Cys Leu Thr Ala Gly Ala Ser Leu
    130                 135                 140

Val Leu Val Lys Pro Glu Ile Met Gln Ser Pro Pro Asp Leu Arg Asp
145                 150                 155                 160

Trp Leu Ile Ala Gln Glu Ile Thr Val Ser Phe Leu Pro Thr Pro Leu
                165                 170                 175

Val Glu Lys Ile Leu Ser Leu Glu Trp Asp Glu Asn Ile Ala Leu Arg
            180                 185                 190
```

```
Ile Ile Leu Thr Gly Gly Asp Lys Leu His His Tyr Pro Ser Gly Leu
        195                 200                 205

Met Pro Phe Lys Leu Ile Asn Asn Tyr Gly Pro Thr Glu Asn Ser Val
    210                 215                 220

Val Thr Thr Ser Gly Leu Val Pro Asp Tyr Glu Glu Gly Asn Pro Pro
225                 230                 235                 240

Ser Pro Ser Ile Gly Lys Pro Val Tyr Asn Thr Lys Ile Tyr Ile Leu
                245                 250                 255

Asp Gln Asn Leu Gln Pro Leu Pro Ile Gly Val Pro Gly Glu Leu His
            260                 265                 270

Ile Ser Ser Val Gly Leu Ala Arg Gly Tyr Leu Asn Arg Leu Glu Leu
        275                 280                 285

Thr Gln Glu Lys Phe Ile Ser Asn Pro Phe Asn Ser
    290                 295                 300


<210> SEQ ID NO 12
<211> LENGTH: 300
<212> TYPE: PRT
<213> ORGANISM: Microcystis aeruginosa
<220> FEATURE:
<221> NAME/KEY: MISC_FEATURE
<222> LOCATION: (1)..(300)
<223> OTHER INFORMATION: Subject Sequence: McyBI of the Microcystis
      aeruginosa strain PCC7806

<400> SEQUENCE: 12

Gly Ile Leu Lys Ala Gly Gly Ala Tyr Val Pro Leu Asp Pro Asp Tyr
1               5                   10                  15

Pro Thr Glu Arg Leu Gly Asp Ile Leu Ser Asp Ser Gly Val Ser Leu
            20                  25                  30

Val Leu Thr Gln Glu Ser Leu Gly Asp Phe Leu Pro Gln Thr Gly Ala
        35                  40                  45

Glu Ser Leu Cys Leu Asp Arg Asp Trp Glu Lys Ile Ala Thr Tyr Ser
    50                  55                  60

Pro Glu Asn His Phe Asn Leu Thr Thr Pro Glu Asn Leu Ala Tyr Val
65                  70                  75                  80

Ile Tyr Thr Ser Gly Ser Thr Gly Lys Pro Lys Gly Val Leu Ile Ser
                85                  90                  95

His Arg Gly Leu Met Asn Leu Ile Cys Trp His Gln Asp Ala Phe Glu
            100                 105                 110

Ile Thr Pro Leu Asp Lys Ile Thr Gln Leu Ala Arg Ile Ala Phe Asp
        115                 120                 125

Ala Ala Val Trp Glu Leu Trp Pro Cys Leu Thr Ala Gly Ala Ser Leu
    130                 135                 140

Val Leu Val Lys Pro Glu Ile Met Gln Ser Pro Pro Asp Leu Arg Asp
145                 150                 155                 160

Trp Leu Ile Ala Gln Glu Ile Thr Val Ser Phe Leu Pro Thr Pro Leu
                165                 170                 175

Val Glu Lys Ile Leu Ser Leu Glu Trp Asp Glu Asn Ile Ala Leu Arg
            180                 185                 190

Ile Ile Leu Thr Gly Gly Asp Lys Leu His His Tyr Pro Ser Gly Leu
        195                 200                 205

Met Pro Phe Lys Leu Ile Asn Asn Tyr Gly Pro Thr Glu Asn Ser Val
    210                 215                 220

Val Thr Thr Ser Gly Leu Val Arg Asp Tyr Glu Glu Gly Asn Pro Pro
225                 230                 235                 240
```

```
Ser Pro Ser Ile Gly Lys Pro Val Tyr Asn Thr Lys Ile Tyr Ile Leu
                245                 250                 255

Asp Gln Asn Leu Gln Pro Leu Pro Ile Gly Val Pro Gly Glu Leu His
            260                 265                 270

Ile Ser Ser Val Gly Leu Ala Arg Gly Tyr Leu Asn Arg Leu Glu Leu
        275                 280                 285

Thr Gln Glu Lys Phe Ile Ser Asn Pro Phe Asn Ser
    290                 295                 300


<210> SEQ ID NO 13
<211> LENGTH: 300
<212> TYPE: PRT
<213> ORGANISM: Artificial Sequence
<220> FEATURE:
<223> OTHER INFORMATION: Consenus sequence of SEQ ID NO: 11 and SEQ ID
      NO: 12
<220> FEATURE:
<221> NAME/KEY: VARIANT
<222> LOCATION: (68)..(68)
<223> OTHER INFORMATION: Residue can be proline or histidine
<220> FEATURE:
<221> NAME/KEY: VARIANT
<222> LOCATION: (103)..(103)
<223> OTHER INFORMATION: Residue can be serine or leucine
<220> FEATURE:
<221> NAME/KEY: VARIANT
<222> LOCATION: (107)..(107)
<223> OTHER INFORMATION: Residue can be tyrosine or histidine. The "+"
      symbol shown in position 107 in Fig. 3 indicates a conservative
      substitution.
<220> FEATURE:
<221> NAME/KEY: VARIANT
<222> LOCATION: (119)..(119)
<223> OTHER INFORMATION: Residue can be tyrosine or isoleucine
<220> FEATURE:
<221> NAME/KEY: VARIANT
<222> LOCATION: (132)..(132)
<223> OTHER INFORMATION: Residue can be leucine or tryptophan
<220> FEATURE:
<221> NAME/KEY: VARIANT
<222> LOCATION: (232)..(232)
<223> OTHER INFORMATION: Residue can be proline or arginine

<400> SEQUENCE: 13

Gly Ile Leu Lys Ala Gly Gly Ala Tyr Val Pro Leu Asp Pro Asp Tyr
1               5                   10                  15

Pro Thr Glu Arg Leu Gly Asp Ile Leu Ser Asp Ser Gly Val Ser Leu
            20                  25                  30

Val Leu Thr Gln Glu Ser Leu Gly Asp Phe Leu Pro Gln Thr Gly Ala
        35                  40                  45

Glu Ser Leu Cys Leu Asp Arg Asp Trp Glu Lys Ile Ala Thr Tyr Ser
    50                  55                  60

Pro Glu Asn Xaa Phe Asn Leu Thr Thr Pro Glu Asn Leu Ala Tyr Val
65                  70                  75                  80

Ile Tyr Thr Ser Gly Ser Thr Gly Lys Pro Lys Gly Val Leu Ile Ser
                85                  90                  95

His Arg Gly Leu Met Asn Xaa Ile Cys Trp Xaa Gln Asp Ala Phe Glu
            100                 105                 110

Ile Thr Pro Leu Asp Lys Xaa Thr Gln Leu Ala Arg Ile Ala Phe Asp
        115                 120                 125

Ala Ala Val Xaa Glu Leu Trp Pro Cys Leu Thr Ala Gly Ala Ser Leu
    130                 135                 140

Val Leu Val Lys Pro Glu Ile Met Gln Ser Pro Pro Asp Leu Arg Asp
145                 150                 155                 160
```

-continued

```
Trp Leu Ile Ala Gln Glu Ile Thr Val Ser Phe Leu Pro Thr Pro Leu
                165                 170                 175

Val Glu Lys Ile Leu Ser Leu Glu Trp Asp Glu Asn Ile Ala Leu Arg
            180                 185                 190

Ile Ile Leu Thr Gly Gly Asp Lys Leu His His Tyr Pro Ser Gly Leu
        195                 200                 205

Met Pro Phe Lys Leu Ile Asn Asn Tyr Gly Pro Thr Glu Asn Ser Val
    210                 215                 220

Val Thr Thr Ser Gly Leu Val Xaa Asp Tyr Glu Glu Gly Asn Pro Pro
225                 230                 235                 240

Ser Pro Ser Ile Gly Lys Pro Val Tyr Asn Thr Lys Ile Tyr Ile Leu
                245                 250                 255

Asp Gln Asn Leu Gln Pro Leu Pro Ile Gly Val Pro Gly Glu Leu His
            260                 265                 270

Ile Ser Ser Val Gly Leu Ala Arg Gly Tyr Leu Asn Arg Leu Glu Leu
        275                 280                 285

Thr Gln Glu Lys Phe Ile Ser Asn Pro Phe Asn Ser
    290                 295                 300
```